(12) United States Patent
Yuan

(10) Patent No.: US 11,730,621 B2
(45) Date of Patent: Aug. 22, 2023

(54) EXOSKELETON

(71) Applicant: Bo Yuan, Chongqing (CN)

(72) Inventor: Bo Yuan, Chongqing (CN)

( * ) Notice: Subject to any disclaimer, the term of this patent is extended or adjusted under 35 U.S.C. 154(b) by 394 days.

(21) Appl. No.: 16/643,329

(22) PCT Filed: Sep. 6, 2018

(86) PCT No.: PCT/CN2018/104410
§ 371 (c)(1),
(2) Date: Feb. 28, 2020

(87) PCT Pub. No.: WO2019/047898
PCT Pub. Date: Mar. 14, 2019

(65) Prior Publication Data
US 2021/0078161 A1 Mar. 18, 2021

(30) Foreign Application Priority Data

Sep. 7, 2017 (CN) .......................... 201710804135.7

(51) Int. Cl.
*A61F 5/01* (2006.01)
*A61F 5/02* (2006.01)

(52) U.S. Cl.
CPC ............ *A61F 5/013* (2013.01); *A61F 5/0127* (2013.01); *A61F 5/026* (2013.01); *A61F 2005/0158* (2013.01); *A61F 2005/0172* (2013.01)

(58) Field of Classification Search
CPC ........ A45F 3/06; A61F 1/0229; A61H 1/0229
See application file for complete search history.

(56) References Cited

U.S. PATENT DOCUMENTS 6,311,708 B1 * 11/2001 Howie ...................... A61H 3/04
482/68
7,628,766 B1 * 12/2009 Kazerooni ................ A61F 5/00
601/5

(Continued)

FOREIGN PATENT DOCUMENTS

CN 101786478 A 7/2010
CN 102256580 A 11/2011

(Continued)

OTHER PUBLICATIONS

Written Opinion of International Searching Authority and International Search Report for International Application No. PCT/CN2018/104410.

*Primary Examiner* — Jacqueline Wozznicki
(74) *Attorney, Agent, or Firm* — JCIP; Joseph G. Chu; Jeremy I. Maynard

(57) ABSTRACT

The present invention discloses an exoskeleton which comprises a force balance back-carrying unit composed of a back-carrying assisting unit and a front-carrying assisting unit, a hip unit and a lower limb supporting unit, wherein the force balance back-carrying unit transfer the weight of a back-carrying load and/or a front-carrying load to the lower limb supporting unit through the hip unit to achieve the effort of assisting for the back-carrying load and/or the front-carrying load, wherein the length of the hip unit can be adjusted on the left-right plane and the upper-lower plane to adapt to wearers with different body types. On the other hand, the exoskeleton of the present invention is also provided with a buffer device to reduce the impact of the loads on the exoskeleton. The exoskeleton of the present invention also adopts quick-release joints, so as to modularize each part and standardize a docking interface of each module. The present invention can adapt to wearers with different hip shapes, and can transfer the weight of the back-carrying load (Continued)

and the front-carrying load to the lower limb supporting unit separately and simultaneously, so as to increase the weight-bearing efficiency and reduce the injuries to the back, the hands and the ankle joint.

11 Claims, 51 Drawing Sheets

(56) References Cited

U.S. PATENT DOCUMENTS

| | | | | |
|---|---|---|---|---|
| 8,474,672 | B1* | 7/2013 | Keith | B25J 9/0006 224/576 |
| 8,968,222 | B2* | 3/2015 | Kazerooni | B25J 9/0006 224/265 |
| 9,266,233 | B2* | 2/2016 | Kornbluh | B25J 9/0006 |
| 10,231,859 | B1* | 3/2019 | Thorne | A61H 1/024 |
| 10,327,536 | B2* | 6/2019 | Pruess | A45F 3/08 |
| 10,870,198 | B1* | 12/2020 | Asbeck | A61H 1/02 |
| 11,000,945 | B2* | 5/2021 | Asada | B25J 9/0006 |
| 2011/0114684 | A1* | 5/2011 | Ya'akobovich | F41H 1/02 224/259 |
| 2011/0120295 | A1* | 5/2011 | Carter | A45F 3/10 224/259 |
| 2011/0264014 | A1* | 10/2011 | Angold | B66D 3/18 212/255 |
| 2012/0192335 | A1* | 8/2012 | Crye | A45F 3/14 2/102 |
| 2013/0232742 | A1* | 9/2013 | Burnett | A45F 3/14 24/606 |
| 2013/0240588 | A1* | 9/2013 | Milligan | A45F 3/06 224/580 |
| 2013/0312150 | A1* | 11/2013 | Klein | A45F 3/08 2/2.5 |
| 2014/0212243 | A1* | 7/2014 | Yagi | B25J 9/0006 414/2 |
| 2014/0224849 | A1* | 8/2014 | Hiemenz | A41D 13/0531 224/271 |
| 2014/0305982 | A1* | 10/2014 | Pelland | A41D 13/0518 224/576 |
| 2015/0366694 | A1* | 12/2015 | Bujold | A61F 5/028 602/19 |
| 2016/0033235 | A1* | 2/2016 | Kinnings | A45F 3/12 2/102 |
| 2017/0035187 | A1 | 2/2017 | Chapman | |
| 2017/0191614 | A1* | 7/2017 | Swan | F16M 13/04 |
| 2018/0056104 | A1* | 3/2018 | Cromie | A63B 21/00181 |
| 2018/0092792 | A1* | 4/2018 | Ohta | B25J 9/0006 |
| 2018/0093374 | A1* | 4/2018 | Holgate | A61H 3/00 |
| 2018/0272524 | A1* | 9/2018 | Ohtsubo | G06F 1/163 |
| 2018/0272525 | A1* | 9/2018 | Kumeno | B25J 9/1638 |
| 2018/0303699 | A1* | 10/2018 | Romo | A61F 5/013 |
| 2018/0338880 | A1* | 11/2018 | Ohta | A61H 1/0262 |
| 2018/0338881 | A1* | 11/2018 | Ohtsubo | A61H 1/0262 |
| 2019/0030708 | A1* | 1/2019 | Holgate | B25J 9/0006 |
| 2019/0041167 | A1* | 2/2019 | Swan | A41D 1/04 |
| 2019/0160652 | A1* | 5/2019 | Mahoney | B25J 9/0006 |
| 2019/0247697 | A1* | 8/2019 | Park | A63B 21/4011 |
| 2019/0358807 | A1* | 11/2019 | Ohta | B25J 9/0006 |
| 2019/0358808 | A1* | 11/2019 | Yoshimi | B25J 9/0006 |
| 2019/0374161 | A1* | 12/2019 | Ly | A61F 2/68 |
| 2020/0000377 | A1* | 1/2020 | Ly | A61B 5/4561 |
| 2020/0030177 | A1* | 1/2020 | Zentgraf | A61H 1/0274 |
| 2020/0069441 | A1* | 3/2020 | Larose | A61F 5/0102 |
| 2020/0069502 | A1* | 3/2020 | Johnson | A61H 1/00 |
| 2020/0093679 | A1* | 3/2020 | Sonar | G06F 3/014 |
| 2020/0198121 | A1* | 6/2020 | Kobayashi | B25J 11/00 |
| 2020/0237600 | A1* | 7/2020 | Arai | A61H 1/00 |
| 2020/0289357 | A1* | 9/2020 | Sato | A61H 1/0281 |
| 2021/0045954 | A1* | 2/2021 | Jang | B25J 9/0006 |
| 2021/0077335 | A1* | 3/2021 | Yoshimi | A61H 1/0237 |
| 2021/0077839 | A1* | 3/2021 | Arai | A61H 1/0262 |
| 2021/0078161 | A1* | 3/2021 | Yuan | A61F 5/013 |
| 2021/0078162 | A1* | 3/2021 | Yoshimi | B25J 9/12 |
| 2021/0078163 | A1* | 3/2021 | Ohtsubo | A61H 1/0244 |
| 2021/0113412 | A1* | 4/2021 | Holgate | A61H 1/00 |
| 2021/0128389 | A1* | 5/2021 | Ohta | A61H 1/0292 |
| 2021/0137720 | A1* | 5/2021 | Tüttemann | A61F 5/028 |
| 2021/0137721 | A1* | 5/2021 | Tütteman | A61F 5/3715 |
| 2021/0275380 | A1* | 9/2021 | Finke | B25J 9/0006 |
| 2021/0291354 | A1* | 9/2021 | Kobayashi | A61H 3/00 |
| 2021/0298985 | A1* | 9/2021 | Asbeck | B25J 9/0006 |
| 2021/0353493 | A1* | 11/2021 | Xue | B25J 9/0006 |
| 2021/0353494 | A1* | 11/2021 | Yoshimi | A61H 1/0292 |
| 2021/0361516 | A1* | 11/2021 | Ohta | A61H 1/00 |
| 2021/0369534 | A1* | 12/2021 | Kobayashi | B25J 9/0006 |
| 2022/0000700 | A1* | 1/2022 | Yoshimi | A61H 3/00 |
| 2022/0000701 | A1* | 1/2022 | Yoshimi | B25J 9/0006 |
| 2022/0008280 | A1* | 1/2022 | Tsuchida | A61H 1/024 |
| 2022/0040025 | A1* | 2/2022 | Yoshimi | A61H 1/0244 |
| 2022/0088767 | A1* | 3/2022 | Holgate | B25J 9/104 |

FOREIGN PATENT DOCUMENTS

| | | | |
|---|---|---|---|
| CN | 102811938 A | 12/2012 | |
| CN | 102973337 A | 3/2013 | |
| CN | 103038152 A | 4/2013 | |
| CN | 203379328 U | 1/2014 | |
| CN | 105856190 A | 8/2016 | |
| CN | 105904440 A | 8/2016 | |
| CN | 106112989 A | 11/2016 | |
| CN | 205766110 U | 12/2016 | |
| CN | 107009349 A | 8/2017 | |
| FR | 3046744 A1 | 7/2017 | |
| WO | WO-2015192240 A1 * | 12/2015 | A61F 5/0102 |

* cited by examiner

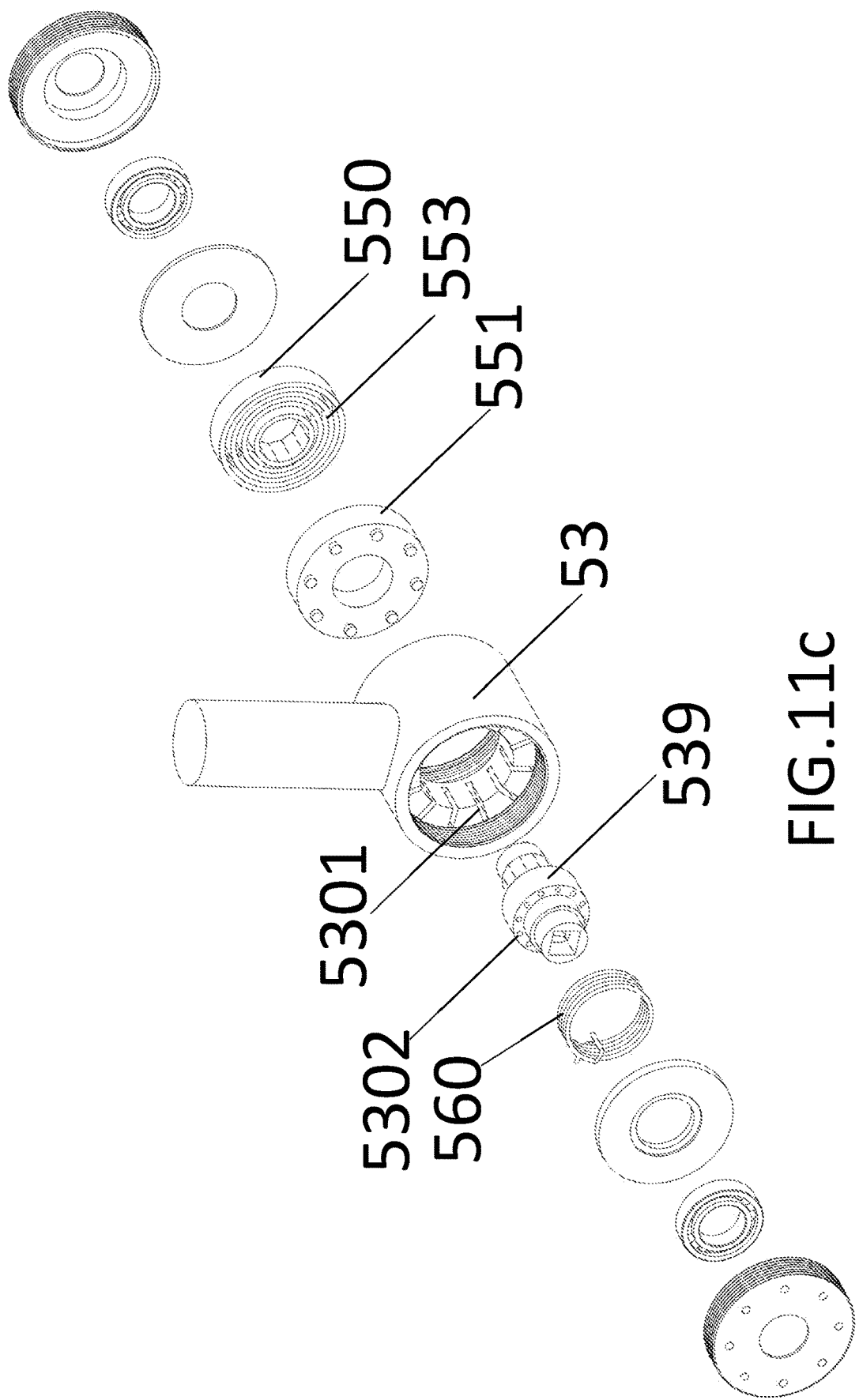

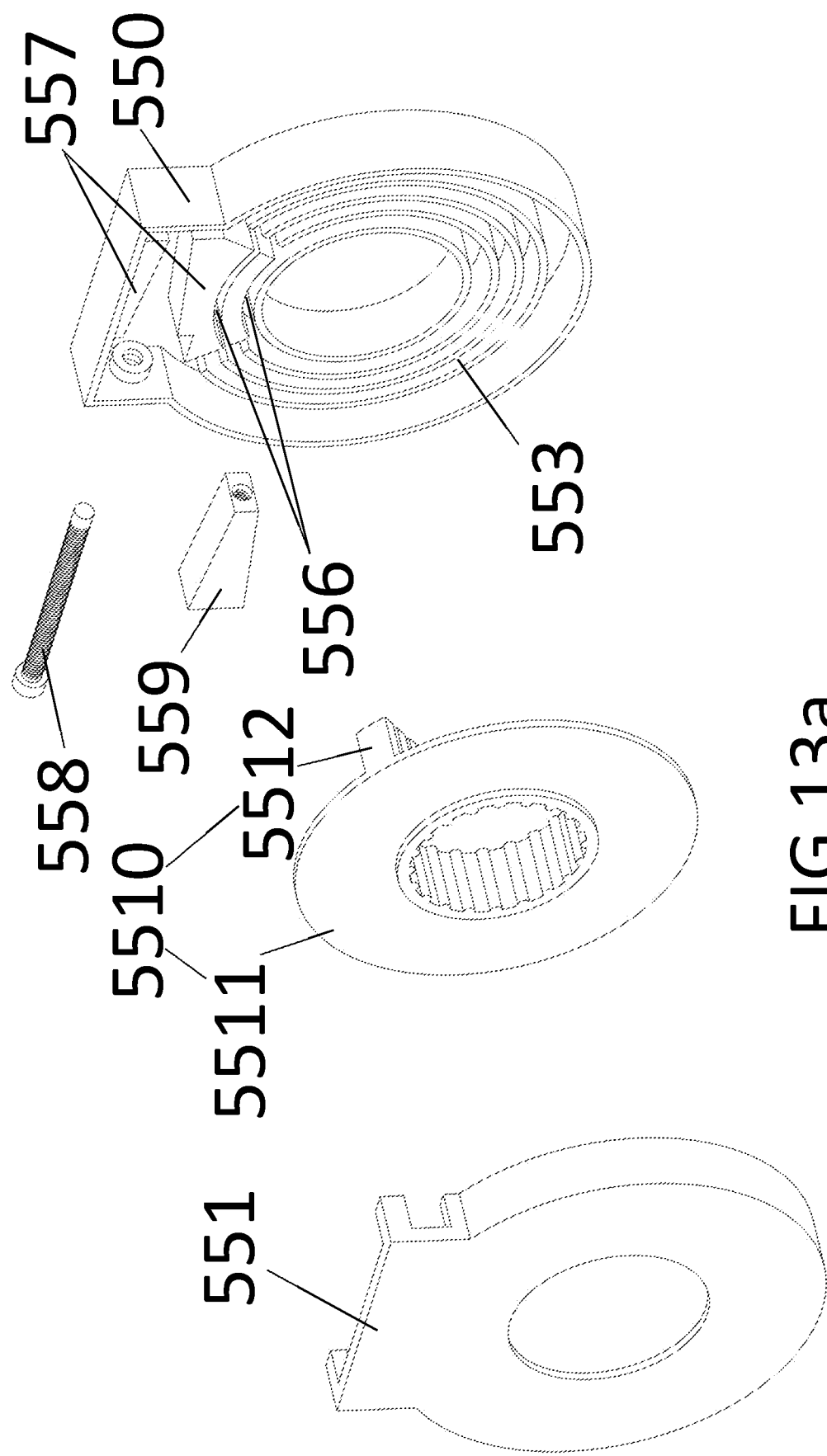

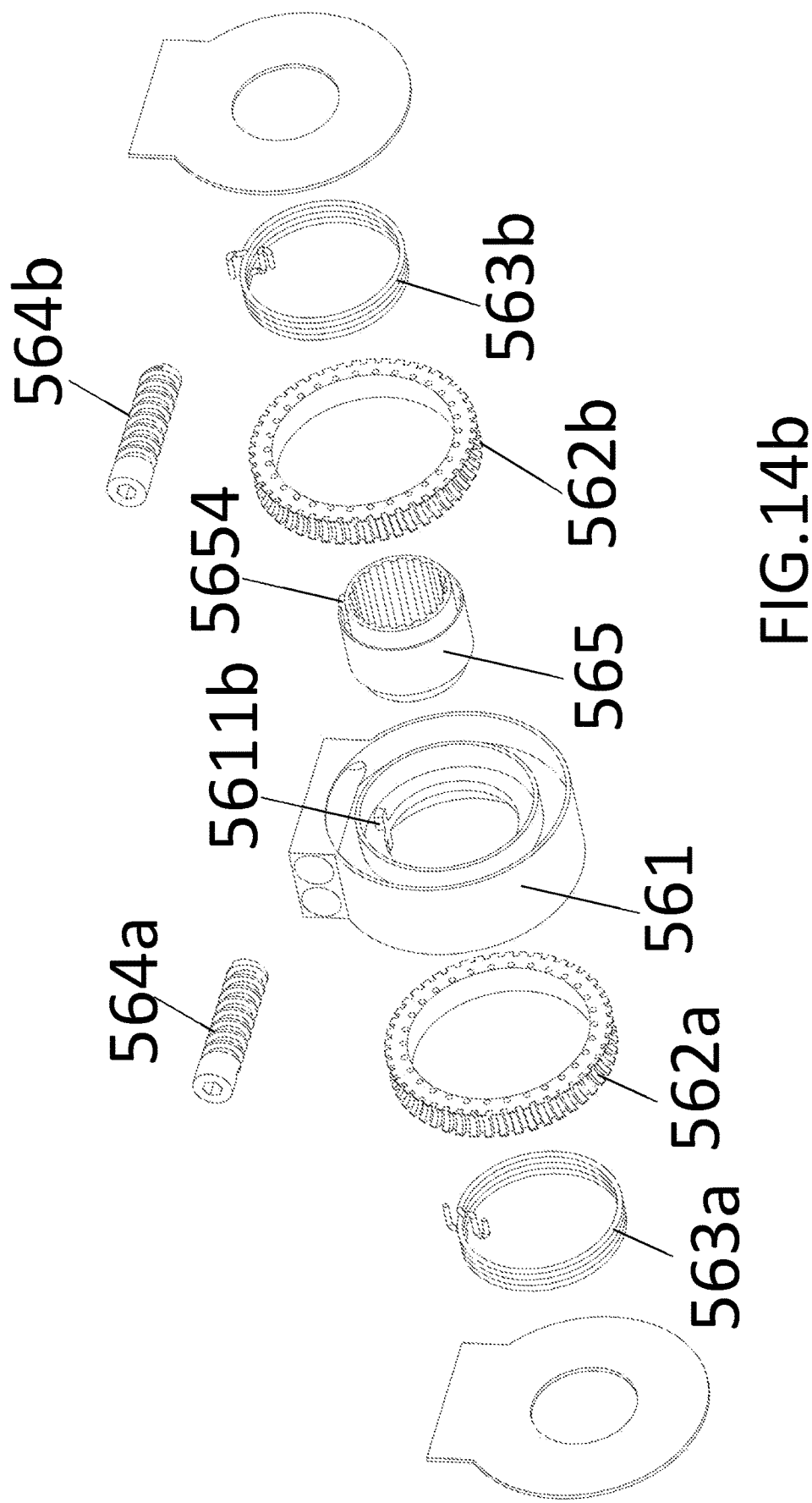

EXOSKELETON

TECHNICAL FIELD

The present invention relates to an exoskeleton load assisting system, and particularly relates to a wearable exoskeleton that can be used for auxiliary handling.

BACKGROUND

Although today's logistics transportation, material handling, etc. can be conducted by land, sea and air, manpower handling is always an important and irreplaceable handling manner. For example, in rescue under geologic disaster, when material handling is needed most urgently, the materials can only be handled by manpower because of roads damages.

Limited by the own physiological structure, the human body is often difficult to handle the materials which are greater than 20 kg for a long time. If a weight-bearing device, such as a backpack or a back rack, is used, the long-time loading capability can be increased to 30 to 50 kg. However, because the backpack and the back rack still rely on the shoulder and the back of the human body to bear the load gravity, and are supported by the skeletal muscle of human lower limb, hence the auxiliary weight-bearing capability of the backpack and the back rack is limited.

In addition, the human body often handles cargoes through holding by the chest, carrying by the shoulder, and lifting by hands. When heavy objects are handled in these modes, handling fatigue is generally not caused by excessive motion; but due to the long-time local pressure on the shoulder, arms, fingers and the like, the local limbs feel severely uncomfortable and the handling fatigue limit is achieved. For example, if a 10 kg plastic bag is lifted by hands, after the plastic bag is carried for just a few minutes, the fingers of lifting the bag are severely pulled to cause ischemia, as a result, the handling can only be continued after change of the hands or rest. In addition, because the articles are not suitable for holding by the chest, lifting, taking by hands, etc., the upper limbs of the human body need to make an additional large sustained force to lift the articles off the ground for handling the articles, which also an important reason for low handling efficiency. For example, when the human body holds a heavy box body by the chest to handle it, the fingers will suffer local pressure and show obvious ischemia. At the same time, since the fingers are always in a bent state to prevent the box body from sliding down, forearm muscles continue to apply a force to keep the fingers in a bent state, which causes the human body to feel pain in the forearms immediately after the heavy box body is handled.

An exoskeleton device is a mechanical device that is worn outside the human body. The device can adapt to the limb motion of the human body, assist the human body to bear the load or the body weight of the human body, efficiently transfer the load or the gravity of the human body to the ground through a mechanical structure, and even assist the limb motion of the human body. Therefore, the device has good application prospects in the fields of disaster rescue, individual weight bearing, fire emergency rescue, outdoor hiking and logistics transportation. Nowadays, there are a variety of exoskeletons for assisting the human body to bear the weight, but most of them employ a back-carrying manner to handle the materials. Some exoskeletons can employ a front-handling manner, but it is difficult to cooperate with the back-carrying manner. There is no exoskeleton that handles the materials in a manner of shoulder carrying. At the same time, when the materials are handled in the back-carrying manner, a special backpack is generally adopted to load the items. There is no multifunctional carrying platform that can handle various types and sizes of materials (water tanks, rice bags, oil drums, backpacks, etc.) and even handle the wounded persons. Additional assistance from operators is often required during use when the cargoes are loaded and unloaded.

In addition, when the human body walks with load, the exoskeleton is subjected to a large impact load due to the up and down movement of the center of gravity of the wearer and the height fluctuation of the ground. Most of the existing exoskeleton technologies do not consider a buffer function during walking with load. Some exoskeleton technologies add a buffer unit at the foot or ankle, thereby causing that a foot device is too bulky or the buffer degree is very limited. However, the buffer device is not considered in the knee joint, the hip joint and even the waist.

Therefore, it is of great significance to develop a wearable auxiliary handling device that can apply to various occasions, improve the weight-bearing efficiency of the wearer, reduce the impact of heavy objects and adapt to the wearers with different body structures. The closest prior art is an exoskeleton auxiliary supporting device which transfers the pressure of the heavy object to the exoskeleton unit through a weight-bearing platform by means of a connecting assembly, to reduce the bearing capacity of the shoulder and the back of a bearer or assist the wearer to handle the load in front of the chest and improve the weight-bearing efficiency. However, most of the weight-bearing platforms involved in the existing exoskeleton can only carry materials of certain sizes and shapes, and cannot adapt to heavy objects of different lengths and shapes, especially the handling of large cargoes (such as refrigerators, televisions, washing machines, etc.). At the same time, the existing device cannot assist a variety of weight-bearing and handling tasks such as hand carrying and shoulder lifting (e.g., carrying loads, lifting stretchers, moving furniture, etc.), and the application range is limited.

SUMMARY

The purpose of the present invention is to overcome the above defects and to provide an exoskeleton that can adapt to the locomotion of human back.

To achieve the above purpose, the present invention adopts the following technical solution:

An exoskeleton comprises a back-carrying assisting unit. The back-carrying assisting unit comprises a spinal locomotion adaptation unit used to adapt to locomotion of human back when the back-carrying assisting unit carries a load or human spine bends forwards, backwards, leftwards or rightwards.

The spinal locomotion adaptation unit is a flexible body; and a plurality of groups of spinal locomotion adaptation structures are arranged on the flexible body evenly along a lengthwise direction from top to bottom, and are used to provide a deformation space in a corresponding direction for the flexible body when a human body bends forwards, backwards, leftwards or rightwards.

The spinal locomotion adaptation unit is an elastic backplane; a plurality of bulges are arranged at even intervals at one side of the elastic backplane away from the human body; or the spinal locomotion adaptation unit is formed by laminating a plurality of elastic bar-shaped bodies; or the spinal locomotion adaptation unit is a bionic spine.

Each group of spinal locomotion adaptation structure comprises a left-tilting slot, a rear-tilting slot, a right-tilting slot, and a front-tilting slot that are staggered in sequence from top to bottom.

In a second aspect of the present invention, an exoskeleton is also provided that achieves separate or synergistic assistance for the back-carrying load and the front-lifting load, while broadening load types and reducing the impact of gravity on the body.

To achieve the above purpose, the present invention adopts the following technical solution:

An exoskeleton comprises a force balance back-carrying unit used for a back-carrying load and a front-carrying load; the force balance back-carrying unit comprises a back-carrying assisting unit and a front-carrying assisting unit which are connected through a force transmission unit, wherein the front-carrying assisting unit transfers the weight of a front-carrying load to the back-carrying assisting unit through the force transmission unit.

The force transmission unit comprises a left and a right force transmission components and a left and a right contraction devices having self-locking units, wherein one end of each of the left and the right force transmission components is respectively twined into the left and the right contraction devices; and when the self-locking units in the contraction devices are unlocked, the contraction devices release the force transmission components twined into the contraction devices; and when the other end of each of the left and the right force transmission components is respectively fixedly connected with the left side and the right side of the front-carrying assisting unit, the left and the right contraction devices are respectively fixed to the left side and the right side of the back-carrying assisting unit; or when the other end of each of the left and the right force transmission components is respectively fixedly connected with the left side and the right side of the back-carrying assisting unit, the left and the right contraction devices are respectively fixed to the left side and the right side of the front-carrying assisting unit.

In a third aspect of the present invention, an exoskeleton is also provided that can achieve quick release of all components in the exoskeleton, so that the exoskeleton is not only convenient for storage, but also modularizes the exoskeleton, thereby facilitating the wearer in quick wear.

To achieve the above purpose, the present invention adopts the following technical solution:

An exoskeleton comprises quick-release joints that can rotate at single degree of freedom/three degrees of freedom and can bear weight, which can modularize each part of the exoskeleton, thereby facilitating disassembling and assembling, storage and wear.

The quick-release joints are single-axis units.

Further, damping units are arranged in the quick-release joints and are used to absorb vibration during the locomotion of the quick-release joints, thereby avoiding a large impact force during the locomotion of the quick-release joints.

Further, pretightening force regulating units are arranged in the damping units and are used to regulate the pretightening force of the damping units.

Further, resilient units are arranged in the quick-release joints and are used to provide resilience for the quick-release joints.

Further, the resilient units are bidirectional resilient units.

In a fourth aspect of the present invention, an exoskeleton is also provided that can reduce the impact generated by the wearer during locomotion or handling, thereby protecting various joints.

To achieve the above purpose, the present invention adopts the following technical solution:

An exoskeleton comprises a buffer device which is matched with each joint of the exoskeleton to achieve multi-degree of freedom motion of each joint of the exoskeleton and absorb impact/vibration on each joint when the exoskeleton carries a load/move.

The buffer device is a porous elastic linear buffer which can be compressed or rebounded axially.

To sum up, compared with the prior art, the present invention at least has the following beneficial technical effects:

1. The spinal locomotion adaptation unit makes the exoskeleton fitted with the human back and makes the wearing of the exoskeleton more comfortable.

2. The force balance back-carrying unit makes the back-carrying load and the front-lifting load more coordinated and balanced.

3. The quick-release joints are adopted at the connection of the exoskeleton to make it more convenient to wear and remove the exoskeleton.

4. The buffer device at each joint of the exoskeleton are adopted, which can reduce the impact generated by the exoskeleton wearer during locomotion or handling, thereby protecting various joints.

5. Multi-functional handling can be achieved: the wearer can get passive auxiliary supporting of a variety of loads such as back-carrying load, shoulder-carrying load and hand-lifting load, as well as multi-person cooperative handling of large and heavy cargoes, so that the persons carrying the load on back can bear heavier objects and different weight-bearing tasks (such as: individual weight bearing, firefighting, stretchers, back carrying of the wounded, and the like) to make the weight-bearing application wider. Moreover, various components of the exoskeleton are modularized through the quick-release joints so that the weight-bearing tasks of back-carrying load, shoulder-carrying load and hand-lifting load can be conducted simultaneously (for example, many people cooperate to handle long and heavy loads and long and heavy tubes) or separately without mutual interference, thereby increasing weight-bearing efficiency. For example, while rescue equipment is carried on the back, the tasks of hand lifting and shoulder carrying of the stretcher can also be assisted.

DESCRIPTION OF DRAWINGS

FIG. 5b is a schematic diagram that reflects that a shoulder supporting component is hinged on a spinal locomotion adaptation structure in FIG. 5a;

FIG. 11b is a structural schematic diagram of a tenon quick-release joint composed of a tenon quick-release connector and a tenon quick-release end in FIG. 11a;

FIG. 11c and FIG. 11d are exploded drawings of a tenon quick-release joint composed of a tenon quick-release connector and a tenon quick-release end reflected in FIG. 11b;

FIG. 12b is a schematic diagram that reflects an internal structure of FIG. 12a;

FIG. 12c is an exploded drawing of a quick-release joint in FIG. 12a;

FIG. 13a and FIG. 13b are exploded drawings that reflect an embodiment of a damping unit in FIG. 12c;

FIG. 14a and FIG. 14b are exploded drawings that reflect an embodiment of a bidirectional resilient unit in FIG. 12c;

FIG. 17b is an exploded drawing of a buffer device in FIG. 17a;

FIG. 20a and FIG. 20b are a structural schematic diagram and an exploded drawing of an embodiment of a hip unit of an exoskeleton in FIG. 1a.

DETAILED DESCRIPTION

To make the purpose, the technical solution and the advantages of the present invention clearer, the present invention will be further described below in combination with drawings and embodiments. It should be understood that specific embodiments described herein are only used to explain the present invention, not to limit the present invention.

Definition of Term

Quick-release joint: the quick-release joint herein refers to a position that can realize quick release of the joints of the exoskeleton or the connected components in order to achieve the modularization of various parts of the exoskeleton. For example, the hip joint, the knee joint, the ankle joint, or a connection between the spinal locomotion adaptation unit and the hip unit in the back-carrying assisting unit, or a connection between the spinal locomotion adaptation unit and the shoulder supporting unit may be configured for quick release.

Embodiment 1

Figure 1A:
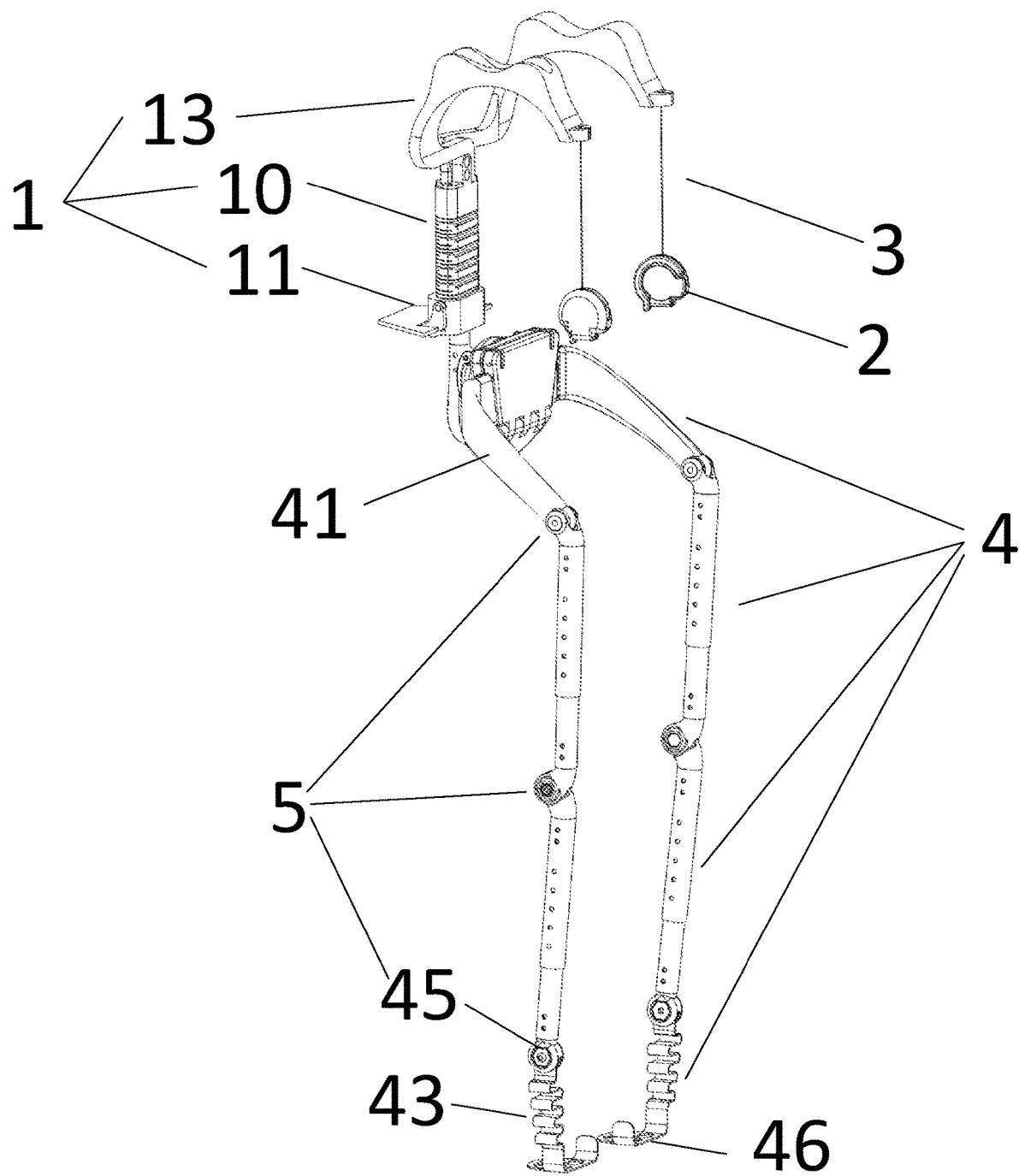
FIG. 1a and FIG. 1b are respectively structural schematic diagrams of two embodiments of an exoskeleton in the present invention.
Figure 1B:
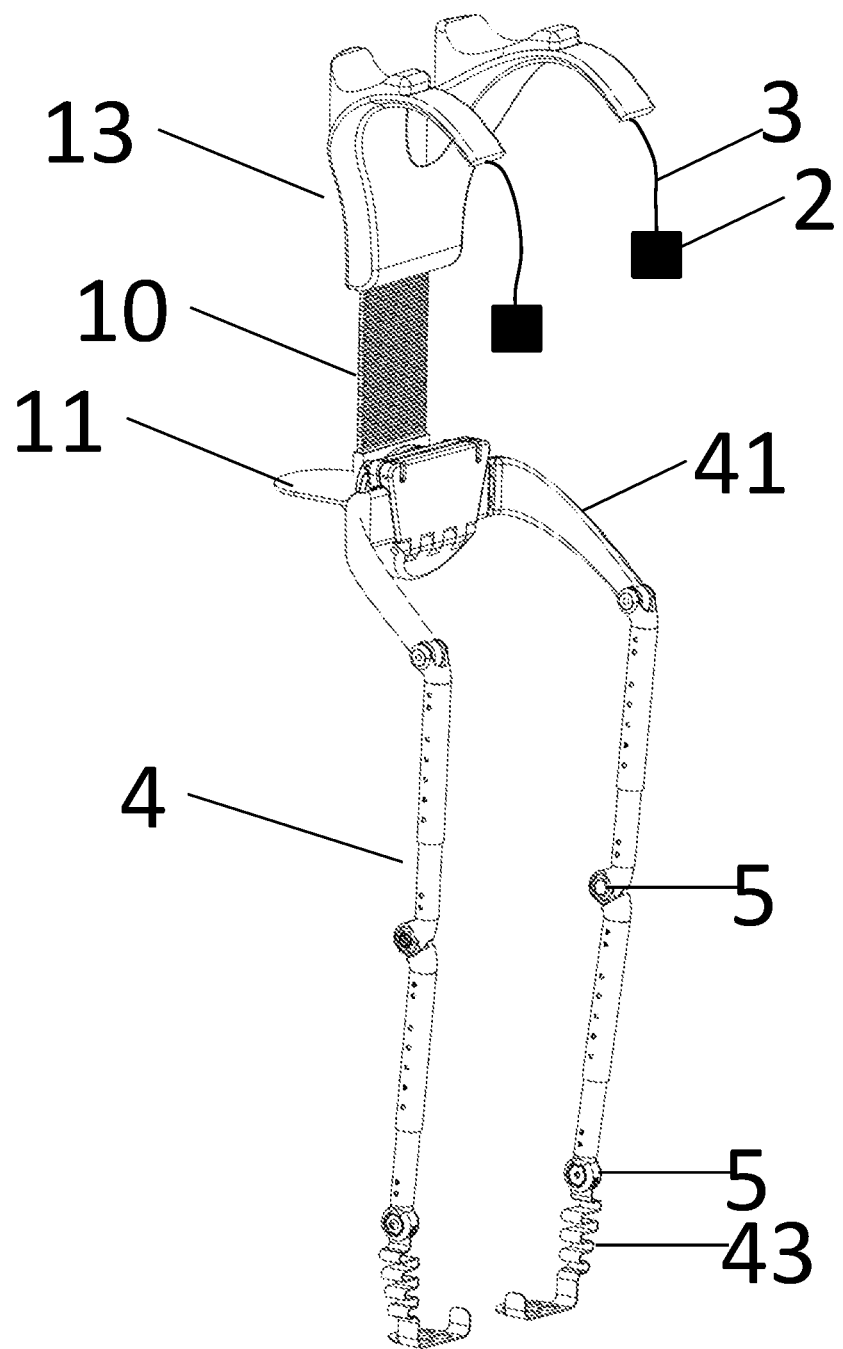

Generally, when the wearer wears the exoskeleton to carry a load or move, the back of the wearer generally bends. For example, when the wearer carries the load on the back or the front, the back generally bends forwards. Therefore, in order to adapt to the curvature of the back of the wearer and improve the comfort of the back of the wearer, the present invention provides an exoskeleton. With reference to FIG. 1a and FIG. 1b, the exoskeleton of the present invention comprises a back-carrying assisting unit 1. The back-carrying assisting unit 1 comprises a spinal locomotion adaptation unit 10 used to adapt to locomotion of the back of the wearer when the back-carrying assisting unit 1 carries a load or the back of the wearer bends forwards, backwards, leftwards or rightwards.

Figure 2A:
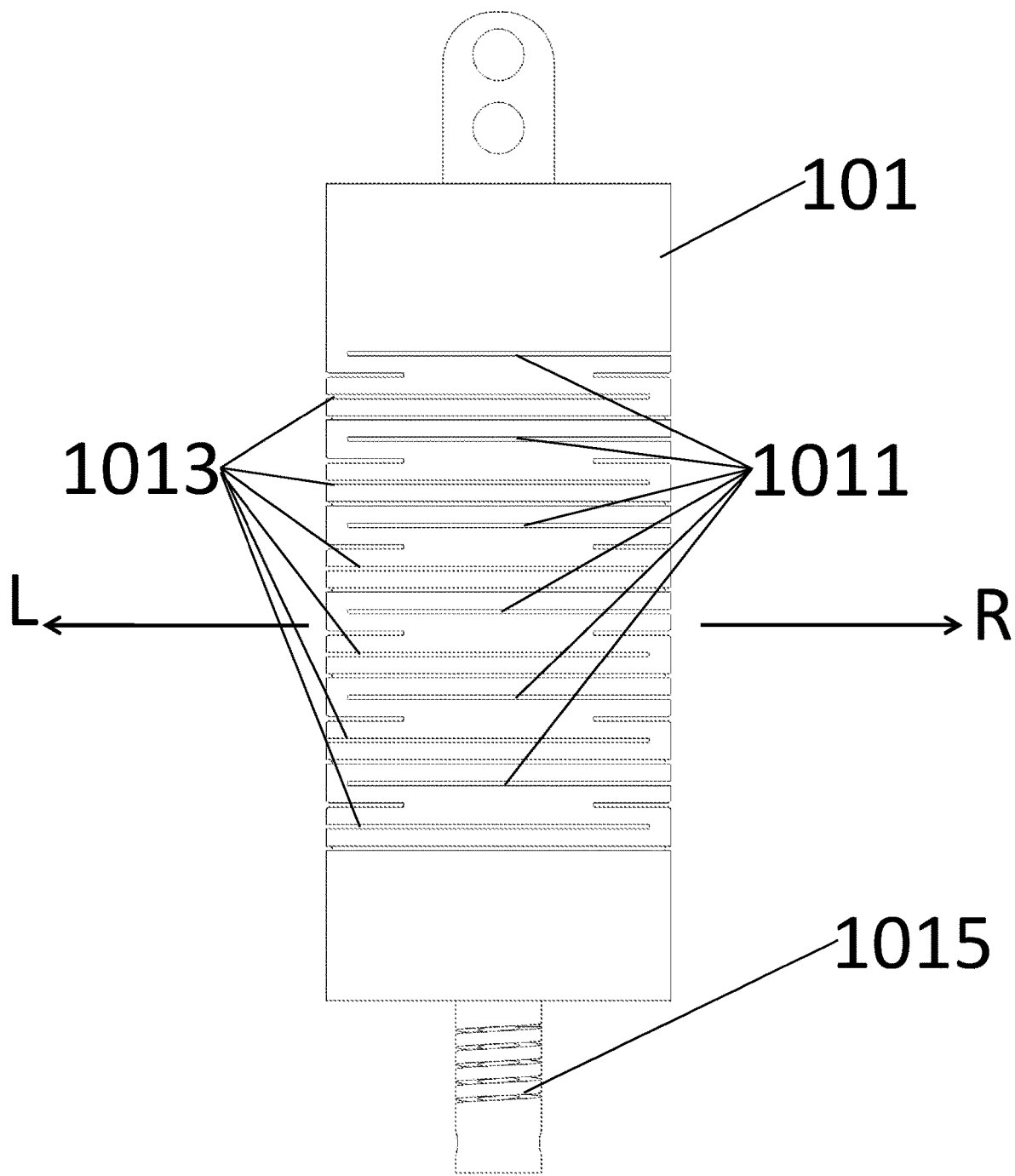
FIG. 2a and FIG. 2b are respectively structural schematic diagrams of two embodiments of a spinal locomotion adaptation unit in a back-carrying assisting unit in an exoskeleton in the present invention.
Figure 2B:
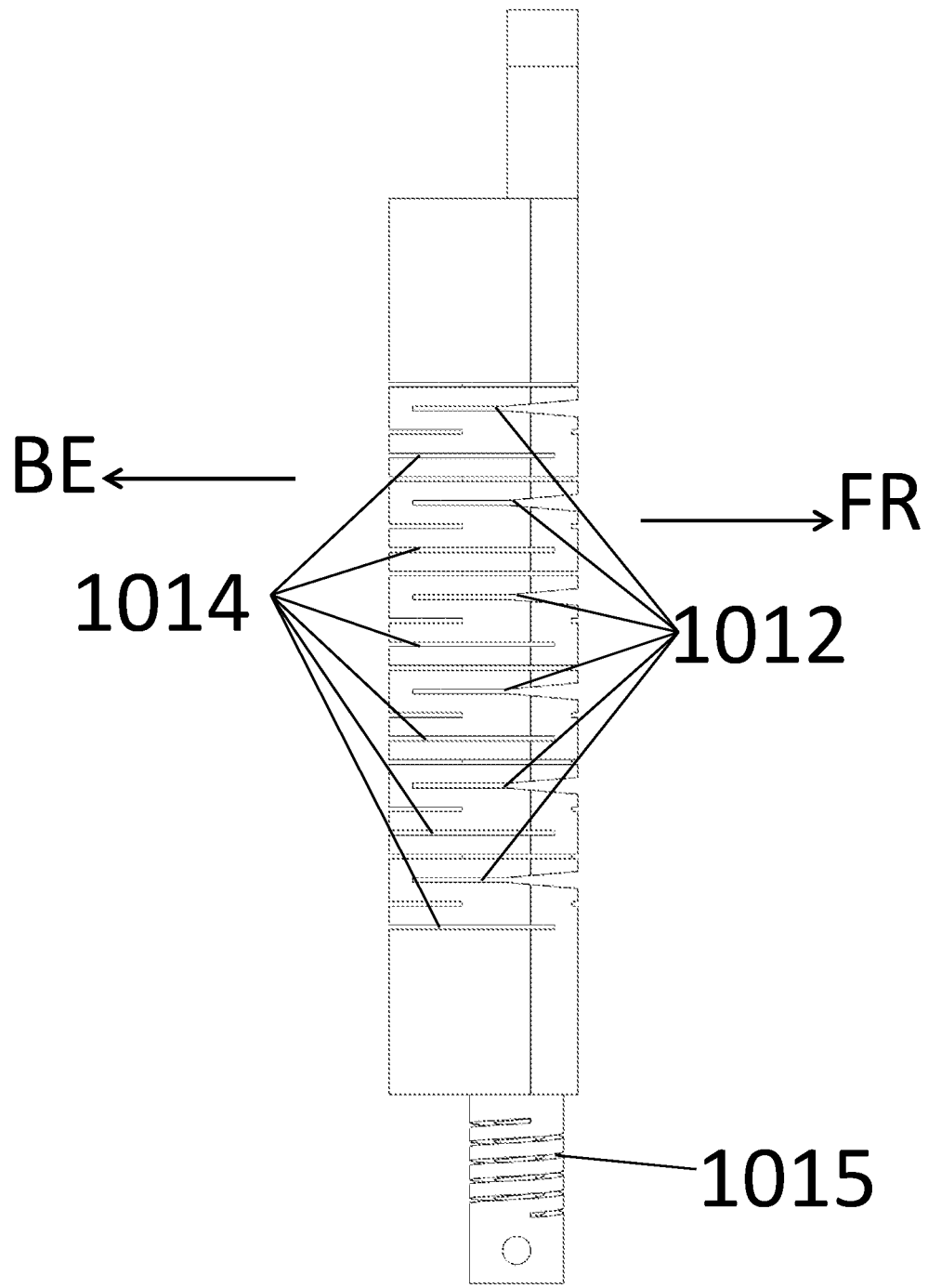

In a specific embodiment, the spinal locomotion adaptation unit 10 of the back-carrying assisting unit 1 is a flexible body 101; and a plurality of groups of spinal locomotion adaptation structures are arranged on the flexible body 101 evenly (or unevenly) along a lengthwise direction from top to bottom, which are used to provide a deformation space in a corresponding direction for the flexible body 101 when the wearer bends forwards, backwards, leftwards or rightwards. Specifically, with reference to FIG. 2a and FIG. 2b (i.e., a back view and a left view of a spinal locomotion adaptation unit 10 in FIG. 1), each group of spinal locomotion adaptation structure comprises a left-tilting slot 1011, a rear-tilting slot 1012, a right-tilting slot 1013, and a front-tilting slot 1014 that are staggered in sequence from top to bottom. Because of the arrangement of the right-tilting slot 1013, when the wearer tilts the back rightwards or bends the back rightwards (i.e., tilts or bends towards R side in FIG. 2a), a slot gap of the right-tilting slot 1013 increases as the right-tilting angle of the back of the wearer increases, thereby enabling the flexible body 101 to tilt/bend rightwards along with the back of the wearer. Similarly, when the wearer tilts the back leftwards or bends the back leftwards (i.e., tilts or bends towards L side in FIG. 2a), a slot gap of the left-tilting slot 1011 increases as the left-tilting angle of the back of the wearer increases, thereby enabling the flexible body 101 to tilt/bend leftwards along with the back of the wearer. Similarly, when the wearer tilts the back forwards or bends the back forwards (i.e., tilts or bends towards FR side in FIG. 2b), a slot gap of the front-tilting slot 1014 increases as the front-tilting angle of the back of the wearer increases, thereby enabling the flexible body 101 to tilt/bend forwards along with the back of the wearer. Similarly, when the wearer tilts the back backwards or bends the back backwards (i.e., tilts or bends towards BE side in FIG. 2b), a slot gap of the back-tilting slot 1012 increases as the back-tilting angle of the back of the wearer increases, thereby enabling the flexible body 101 to tilt/bend backwards along with the back of the wearer. That is, in the present embodiment, a corresponding deformation space is provided for the flexible body 101 by arranging the left-tilting slot 1011, the rear-tilting slot 1012, the right-tilting slot 1013, and the front-tilting slot 1014, so that the flexible body 101 can bend as the back of the wearer bends and the comfort and the fit of the back of the wearer are improved.

Further, the back of the wearer may be rotated in the horizontal plane except for the forward, backward, leftward or rightward bending motion. For example, the back of the wearer is rotated counterclockwise or clockwise, so that the face of the wearer rotates to the back. Therefore, to adapt to the rotation motion of the back of the wearer, the bottom of the flexible body 101 is also provided with a rotating adaptation structure in the present embodiment so that the flexible body 101 can rotate and deform in the horizontal plane along with the rotation of the back of the wearer. In a specific embodiment, with reference to FIG. 2a and FIG. 2b, the rotating adaptation structure is a rotating slot 1015, which is arranged in the bottom of the flexible body 101. In addition, the rotating adaptation structure may also employ a torsion spring, that is, a shape of the torsion spring is set at the bottom of the flexible body 101, or a torsion spring is directly connected to the bottom.

However, when the back-carrying assisting unit carries a large load, the soft and flexible spine is likely to have a deviation from the vertical direction of the flexible spine due to the gravity of the load, causing a bending moment on the flexible spine. At this moment, the spinal locomotion adaptation unit in the back-carrying assisting unit should just allow the wearer to straighten the back instead of bending or arching the back, thereby avoiding the damage to the spine of the wearer caused by the heavy load.

In view of this, further, in the present embodiment, the flexible body 101 is also provided with a rigidity regulating unit used for regulating the rigidity of the flexible body, thereby avoiding the damage to the spine of the wearer caused by the heavy load. In a specific embodiment, with reference to FIG. 3a and FIG. 3b, the rigidity regulating unit comprises a left and a right pull lines 1031 arranged in the flexible body 101. Accordingly, the left and right sides of the flexible body 101 are provided with a first pull line passage 1016 and a second pull line passage 1017 side by side along the lengthwise direction, wherein the fixed end of the right pull line 1031 is fixed to the bottom of the right first pull line passage 1016, and the free end of the right pull line 1031 penetrates into the right first pull line passage 1016 and penetrates out of the top of the right first pull line passage 1016, and then bypasses a pulley 1018 arranged between the right first pull line passage and the top of the second pull line passage, penetrates from the top of the right second pull line passage 1017 and finally penetrates out of the bottom of the right second pull line passage 1017. Similarly, the fixed end of the left pull line 1031 is fixed to the bottom of the left first pull line passage 1016, and the free end of the left pull line 1031 penetrates into the left first pull line passage 1016 and penetrates out of the top of the left first pull line passage 1016, and then bypasses a pulley 1018 arranged between the left first pull line passage 1016 and the top of the second pull line passage 1017, penetrates from the top of the left second pull line passage 1017 and finally penetrates out of the bottom of the left second pull line passage 1017. That is, the left and the right pull lines 1031 respectively penetrate through the first pull line passage 1016 and the second pull line passage 1017 on the corresponding side in sequence, and penetrate out of the bottom of the second pull line passage 1017 on the corresponding side, so that the pulling force generated by the two pull lines 1031 compresses each group of spinal locomotion adaptation structure when the free ends of the left and the right pull lines 1031 are simultaneously pulled down, thereby improving the rigidity of the flexible body 101.

Further, to perform a buffering role, an elastic component 1032 is also fixed to the fixed end of the pull line 1031 in the present embodiment (specifically, the elastic component 1032 is a spring; accordingly, a head cover 1033 is connected to the fixed end of the pull line 1031 to fix the head cover 1033 to one end of the spring, and the free end of the pull line 1031 penetrates through the spring and enters the first pull line passage 1016). Thus, when the pull line 1031 is pulled down, the pull line 1031 first compresses the elastic component 1032, and the elastic component 1032 reacts on the flexible body 101 to compress each group of spinal locomotion adaptation structure until the reaction force of the elastic component and the pulling force of the pull line 1031 achieve the force balance.

Figure 4A:
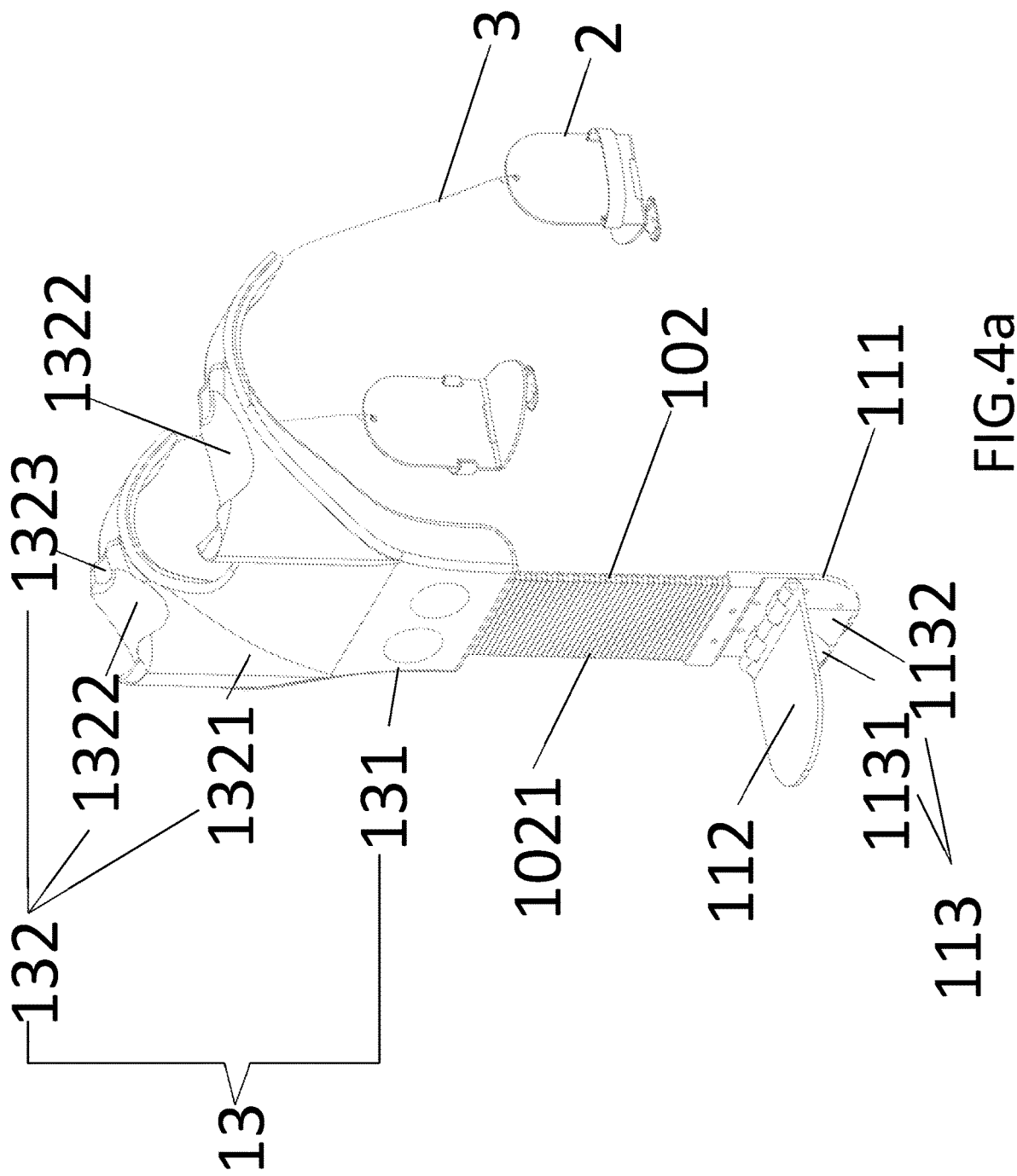
FIG. 4a and FIG. 4b are respectively structural schematic diagrams that reflect two embodiments of a supporting unit in an exoskeleton in the present invention.

In addition, in the present embodiment, the spinal locomotion adaptation unit 10 may also not employ the flexible body, but adopts an elastic backplane 102 made of curved elastic material. With reference to FIG. 1b and FIG. 4a, the elastic backplane 102 can bend as the back of the wearer bends, and can give a reacting force for the back of the wearer (of course, the elastic backplane does not need the rigidity regulating unit). Further, when the wearer carries a heavy object on the back, to prevent the elastic backplane 102 from being bent away from the back of the wearer (i.e., preventing the back of the wearer from bending toward the back), a plurality of lug bosses 1021 are arranged at even intervals at one side of the elastic backplane 102 away from the back of the wearer (specifically, the lug bosses may be in the shape of horizontal bars), and there is a gap with slight width between adjacent lug bosses, so that the elastic backplane 102 is easily bent toward the back of the human body (i.e., the human body arches the back).

Embodiment 2

Generally, when the wearer carries a heavy object on the back, it is not ideal for the wearer to manually pull down the pull line to regulate the rigidity of the flexible body 101. Therefore, the present invention proposes another exoskeleton, which comprises the components in the above embodiment 1, and the same reference numerals indicate the same components, which are not described herein. However, the difference is that, in the present embodiment, the back-carrying weight-bearing unit 11 in the back-carrying assisting unit 1 of the exoskeleton is associated with the rigidity regulating unit in the embodiment 1, thereby transfering the weight of the load on the back-carrying weight-bearing unit 11 to the rigidity regulating unit. Then, the weight of the load is used to compress the spinal locomotion adaptation structure to achieve the purpose of regulating the rigidity of the flexible body 101 to a desired state and also give a supporting force for the back-carrying weight-bearing unit 11.

Figure 3A:
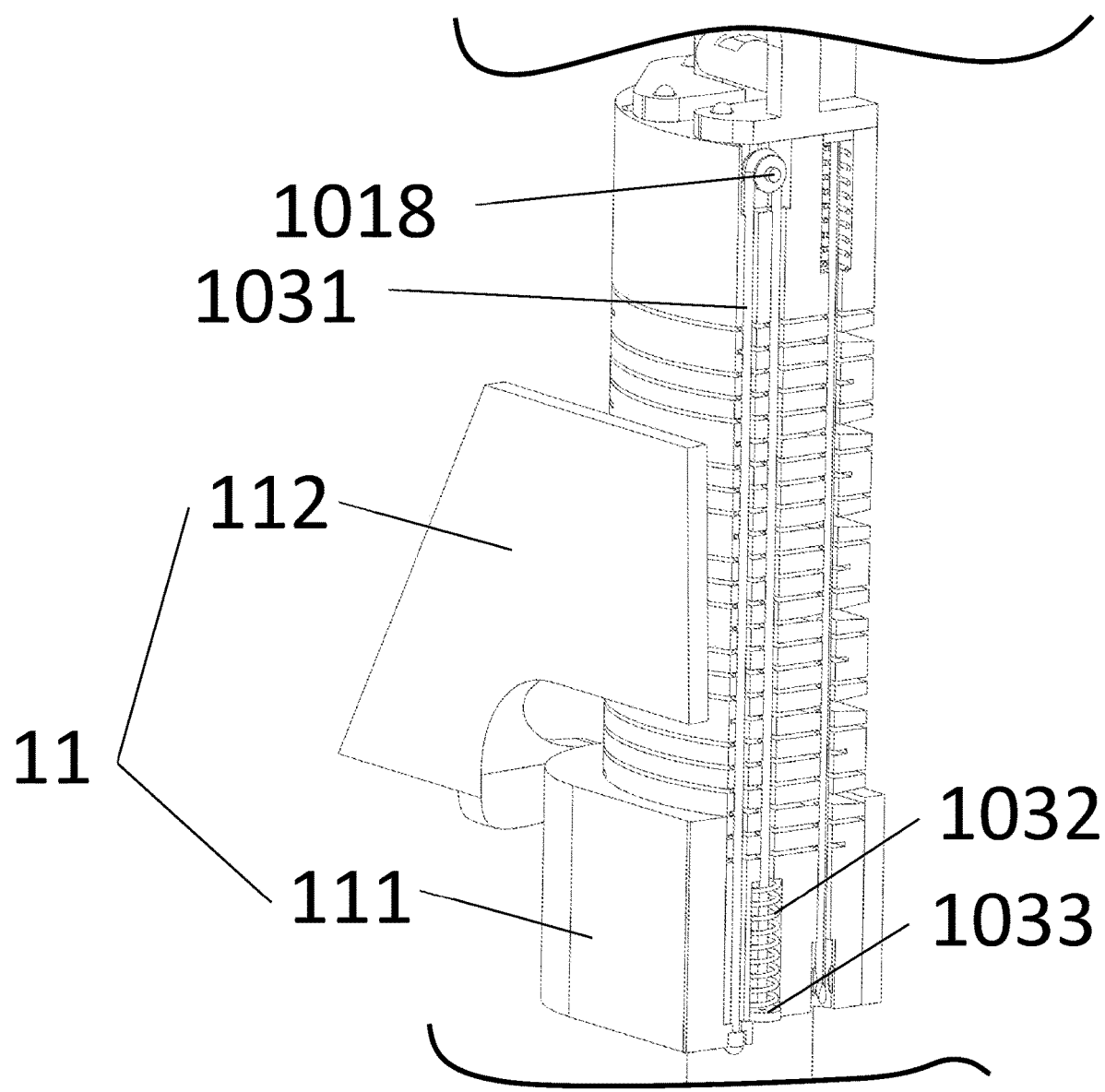
FIG. 3a and FIG. 3b are respectively structural schematic diagrams that reflect a flexible body of an exoskeleton in the present invention.
Figure 3B:
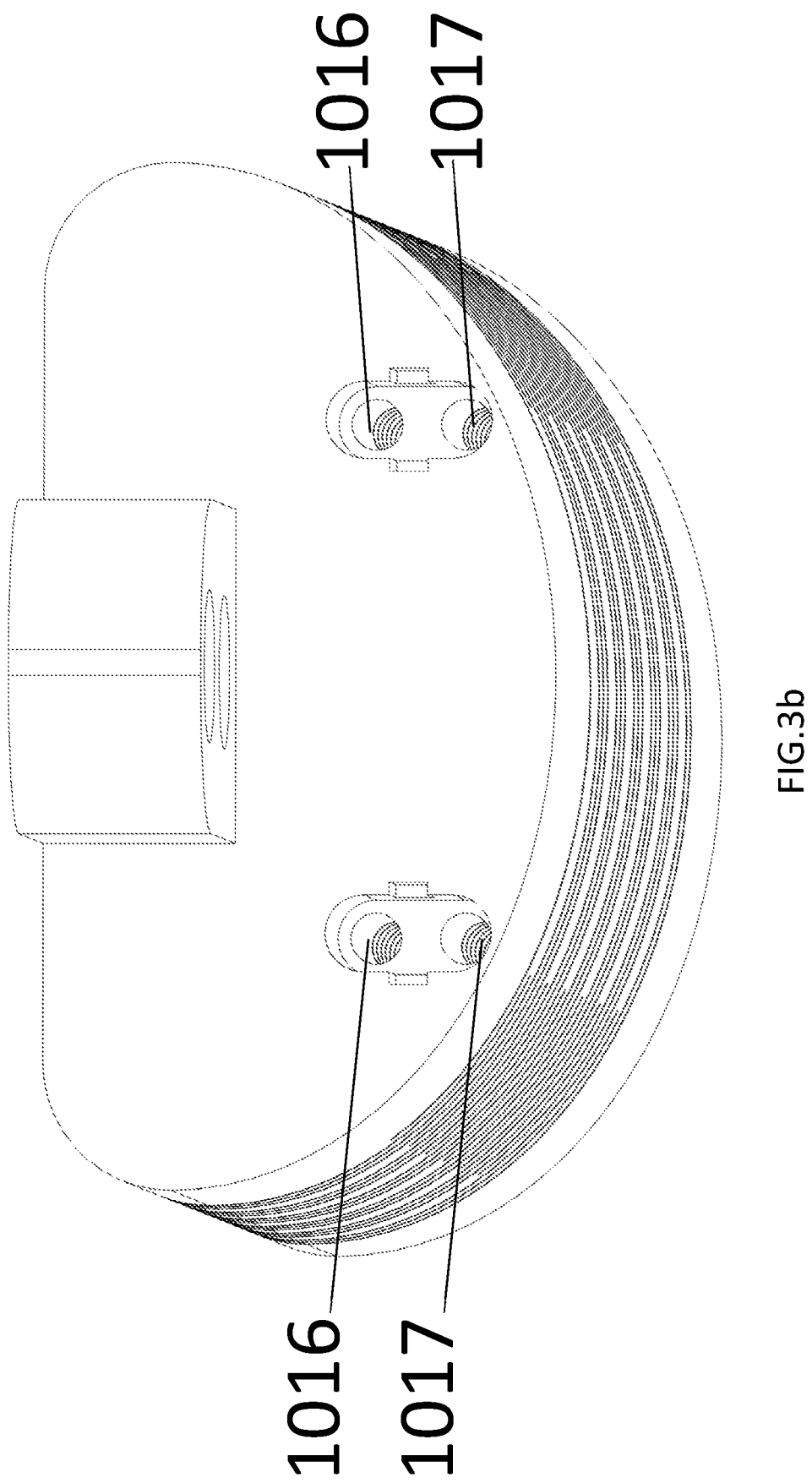

In a specific embodiment, with reference to FIG. 3a, the back-carrying weight-bearing unit 11 comprises a fixed seat 111 and a weight-bearing platform 112 hinged on a fixed platform 111, wherein the fixed seat 111 is arranged at the bottom of the flexible body 101 by sliding up and down relative to the flexible body 101 (for example, the fixed seat 111 is directly sleeved to the bottom of the flexible body 101, as shown in FIG. 3a), and the left side and the right side of the fixed seat 111 are fixedly connected with the free ends of the left and the right pull lines 1031 in a detachable manner. Specifically, a ball is arranged through the free end, and a groove for accommodating the ball is disposed at a position corresponding to the bottom of the second pull line passage of the fixed seat, so that the free end of the pull line is positioned by the cooperation between the ball and the groove.

Figure 3C:
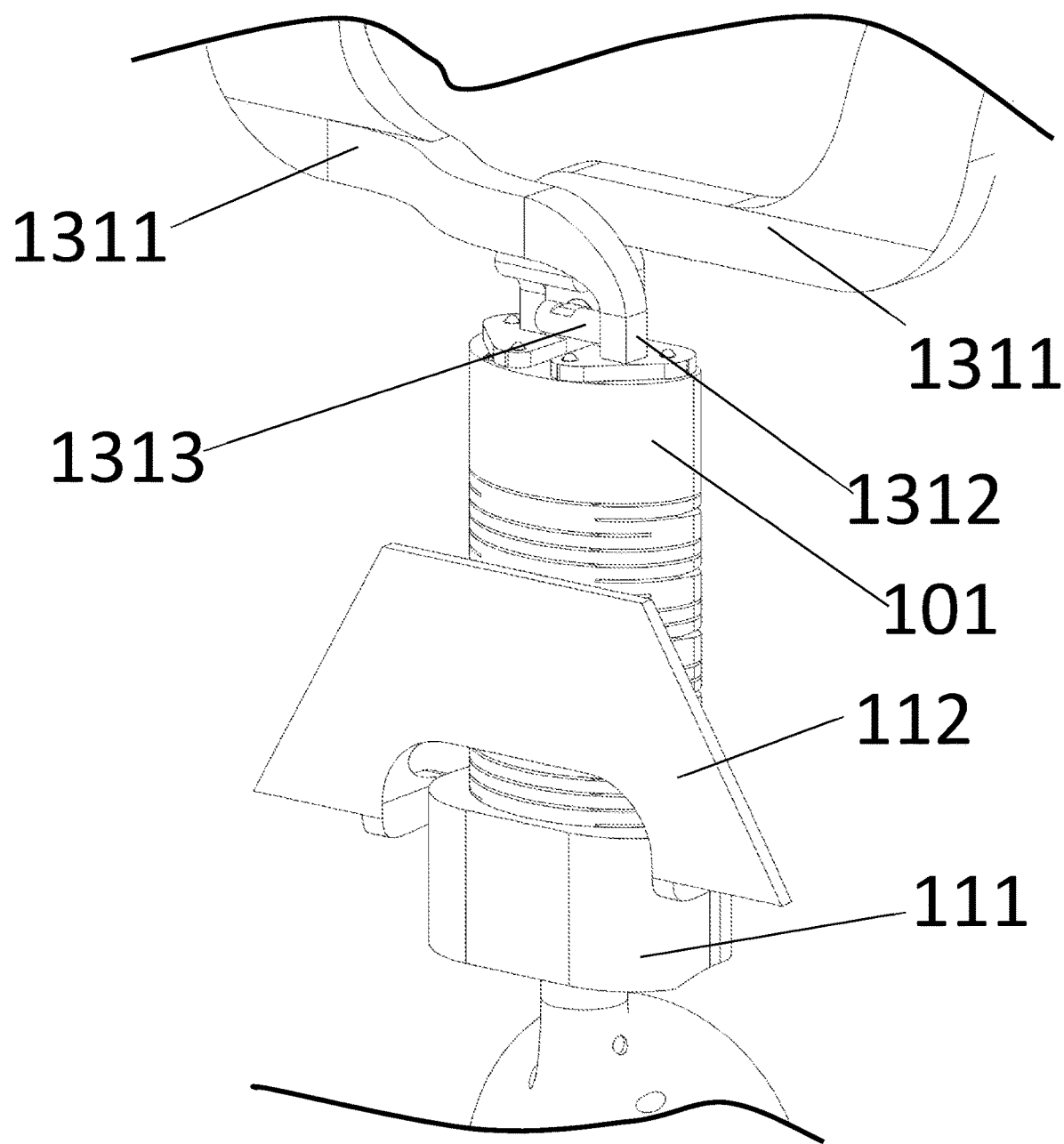
FIG. 3c and FIG. 3d are respectively schematic diagrams that reflect a state that a weight-bearing platform of an exoskeleton is attached to a flexible body and is perpendicular to the vertical plane in the present invention.
Figure 3D:
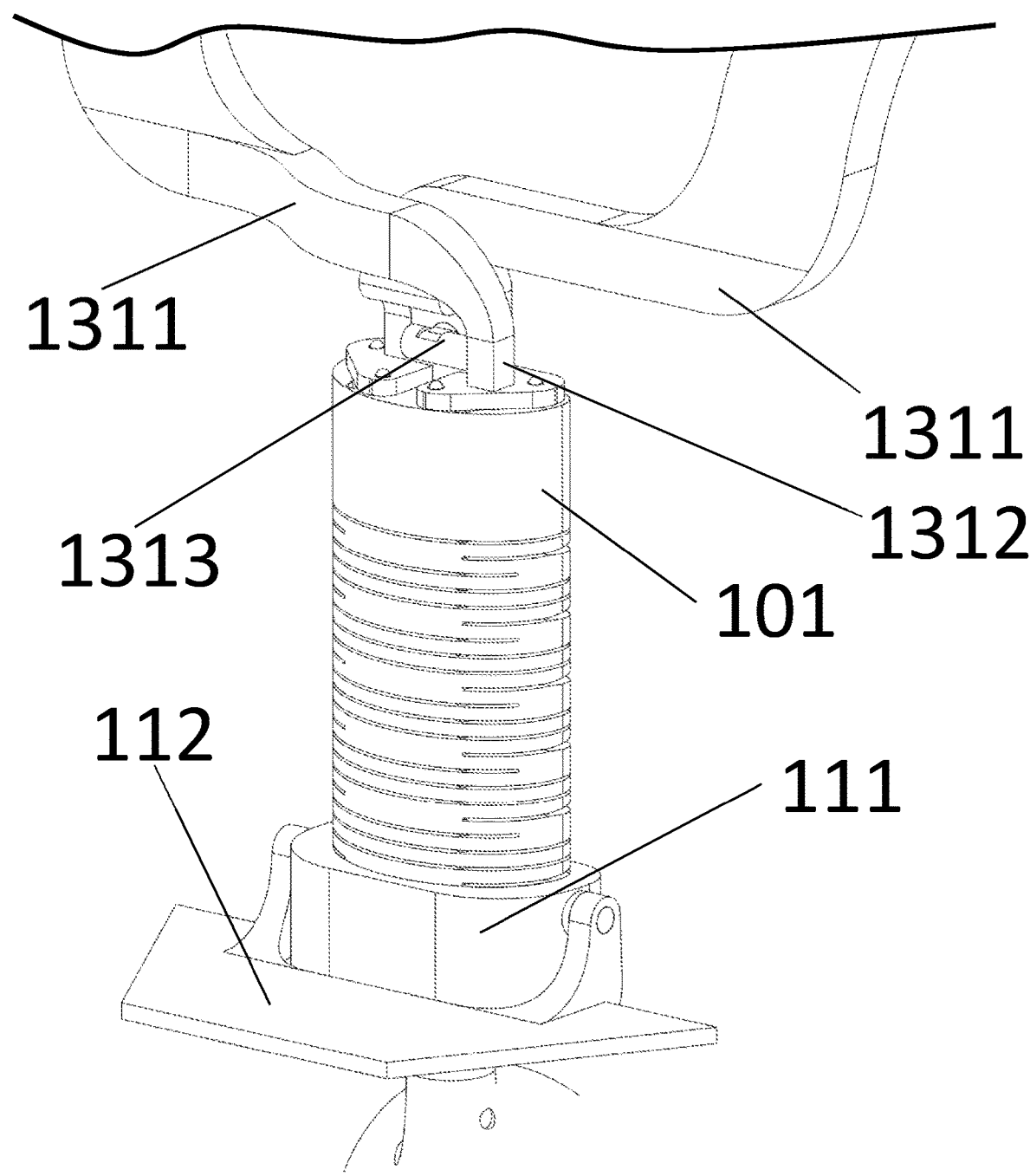

In the initial state, the weight-bearing platform 112 is attached to the fixed seat 111. That is, when there is no need to place a heavy object on the weight-bearing platform 112, since the weight-bearing platform 112 is hinged on the fixed seat 111, the weight-bearing platform 112 can be turned upward to attach to the fixed seat 111, as shown in FIG. 3c, thereby realizing the folding and retracting of the weight-bearing platform 112 and reducing the volume of the back device. Similarly, with reference to FIG. 3d, when the weight-bearing platform 112 rotates to form an angle of 45° to 90° with one side of the fixed seat 111 away from the back/hip, the weight-bearing platform 112 and one side of the fixed seat 111 away from the back/hip form a weight-bearing space for accommodating the loads; and when the loads are put into the weight-bearing space, the fixed seat 111 slides downwards along the bottom of the flexible body 101 under the action of the weight of the loads and drives the free ends of the left and the right pull lines 1031 to move downwards (specifically, the ball is driven by the bottom groove, and the ball drives the free ends of the left and the right pull lines 1031 to move downwards). Thus, the weight of the back load is transmitted to the flexible body 101 through the weight-bearing platform 112, the fixed seat 111 and the left and the right pull lines 1031, and the plurality of groups of spinal locomotion adaptation structures on the flexible body 101 are compressed to finally achieve the force balance. At the same time, the rigidity of the flexible body 101 also achieves the best state.

Figure 4B:
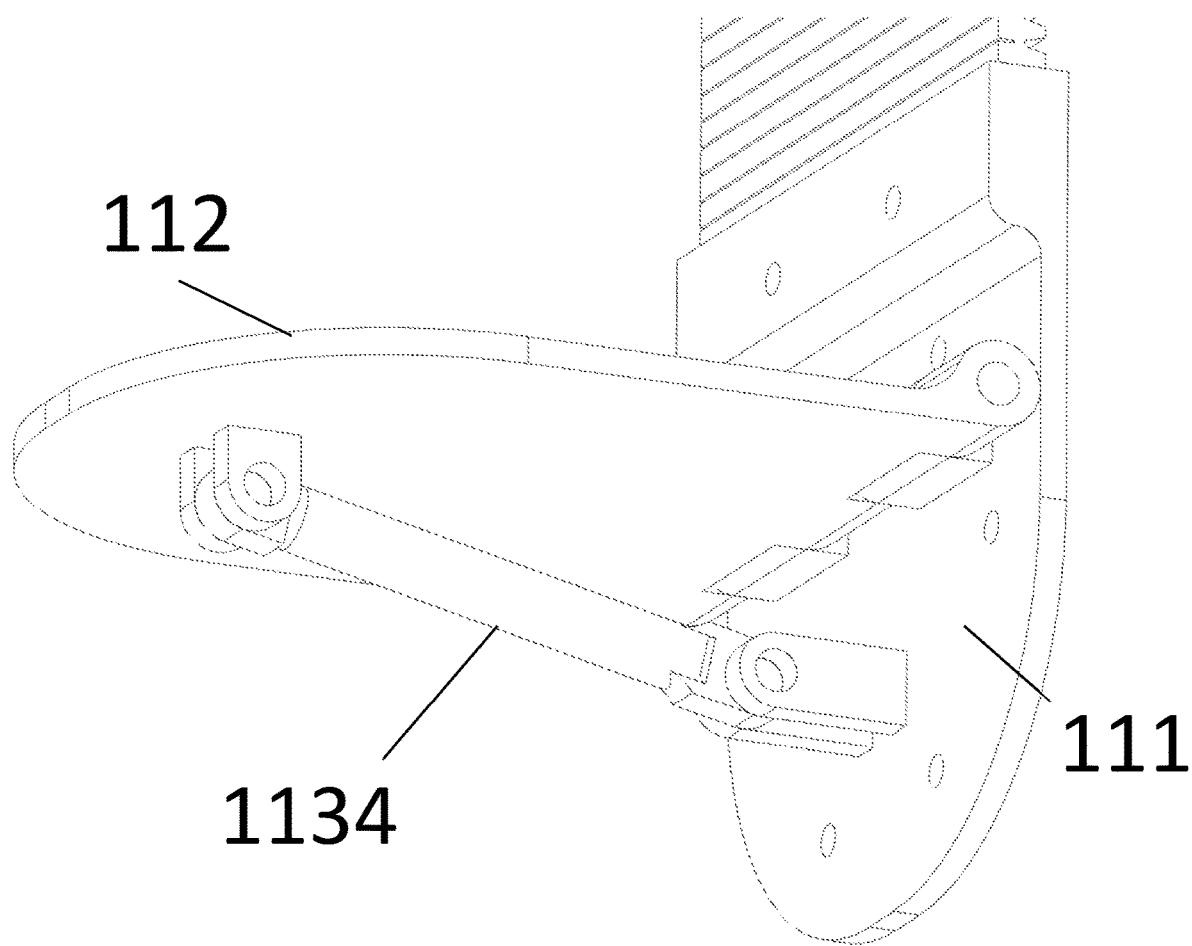

Further, the back-carrying weight-bearing unit 11 also comprises a supporting unit 113 arranged below the weight-bearing platform 112 and used to support the weight-bearing platform 112 when the weight-bearing platform carries the load. In a specific embodiment, with reference to FIG. 4a, the supporting unit 113 comprises a first collision angle 1131 fixed to the back surface of the weight-bearing platform 112 and a second collision angle 1132 fixed to the outer surface of the fixed seat 111 (i.e., the side surface away from the hip/waist of the wearer), and when the weight-bearing platform 112 and the outer surface of the fixed seat 111 form 90°, the first collision angle 1131 comes into contact with the second collision angle 1132, thereby supporting the weight-bearing platform 112. In addition, in the present embodiment, instead of arranging two collision angles, only one supporting angle may be arranged, and the supporting angle is fixed to the outer surface of the fixed seat 112, so that when the weight-bearing platform 112 and the outer surface of the fixed seat 111 form 90°, the supporting angle is abutted against the back surface of the weight-bearing platform 112 (of course, the supporting angle may also be directly fixed to the back surface of the weight-bearing platform 112; therefore, when the weight-bearing platform 112 and the outer surface of the fixed seat 111 form 90°, the supporting angle is abutted against the outer surface of the fixed seat 111), thereby providing a supporting force for the weight-bearing platform 112. In another specific embodiment, the supporting unit 113 is a gas-propelled rod 1134, and both ends of the gas-propelled rod 1134 are respectively connected with the back surface of the weight-bearing platform 112 and the outer surface of the fixed seat 111, as shown in FIG. 4b.

In addition, in the present embodiment, when the spinal locomotion adaptation unit 10 does not employ the flexible body 101, but employs the elastic backplane 102, the rigidity regulating unit is not required and the fixed seat 111 in the weight-bearing unit 11 is directly arranged on the bottom end of the elastic backplane 102. Specifically, as shown in FIG. 4a, a wedge groove is set at the upper side of the fixed seat 111, and the lower side of the elastic backplane 102 can be inserted into and fixed to the wedge groove at the upper side of the fixed seat 111. Then, a sliding rail and a locking unit are arranged in the wedge groove at the upper sideof the fixed seat 111, and the lower side of the elastic backplane 102 can slide along the sliding rail in the wedge groove at the upper side of the fixed seat 111 and is locked by the locking unit. That is, the distance that the elastic backplane 102 slides in the rail can be regulated. When the elastic backplane slides to a required distance, the elastic backplane is locked by the locking unit. That is to say, by arranging the sliding rail in the wedge groove at the upper side of the fixed seat 111, the vertical attaching length of the back-carrying assisting unit and the back of the wearer can be regulated to meet the wear requirements of the wearers of different heights.

Embodiment 3

Generally, most of the heavy objects can be directly fixed to the back-carrying assisting unit of the exoskeleton. However, there are some heavy objects that may be more suitable for shoulder loading, such as carrying loads or heavy rods or heavy pipes. Based on this, the present invention also provides an exoskeleton, which comprises the components in the above embodiment 1 or embodiment 2, and the same reference numerals indicate the same components, which are not described herein. However, the difference is that, the back-carrying assisting unit of the exoskeleton comprises a shoulder supporting piece 13 for assisting the wearer in shoulder loading.

Figure 5A:
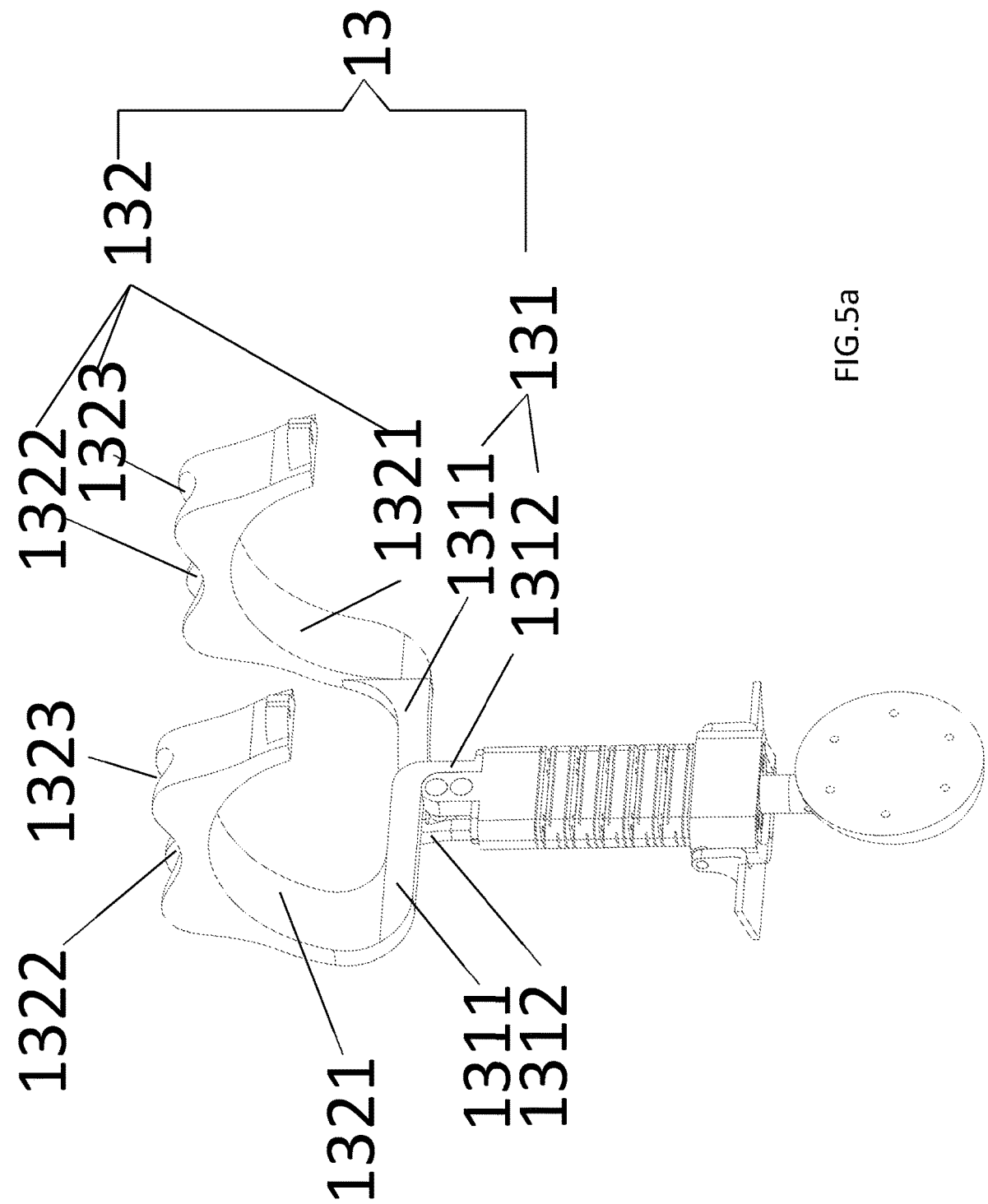
FIG. 5a is a structural schematic diagram that reflects an embodiment of a shoulder supporting component of an exoskeleton in the present invention.

Specifically, with reference to FIG. 4a and FIG. 5a, the shoulder supporting piece 13 comprises a shoulder base 131 connected with the spinal locomotion adaptation unit 10 (such as the flexible body or the elastic backplane), and two shoulder weight-bearing platforms 132. The two shoulder weight-bearing platforms 132 are respectively arranged on the left side and the right side of the shoulder base 131, wherein the shoulder weight-bearing platforms 132 comprise shoulder adaptation bodies 1321 adapted with the shoulder structure of a wearer, wherein the shoulder adaptation bodies 1321 are connected with the shoulder base 131, and are provided with transverse weight-bearing grooves 1322 and longitudinal weight-bearing grooves 1323, wherein the transverse weight-bearing grooves 1322 are used for transversely putting weight-bearing burdens (or heavy rods and heavy pies) to transmit the gravity to the spinal locomotion adaptation unit 10 through the shoulder adaptation bodies 1321 and the shoulder base 131 (of course, the spinal locomotion adaptation unit 10 can also further transmit the gravity to the lower limb supporting unit of the exoskeleton), thereby realizing auxiliary assisting transportation of single-person transverse carrying of the burdens (or heavy rods and heavy pies) or multi-person transverse (left-right) cooperation of carrying the burdens (or heavy rods and heavy pies). Similarly, the longitudinal weight-bearing grooves 1323 are used for longitudinally putting weight-bearing burdens (or heavy rods and heavy pies) to transmit the gravity to the spinal locomotion adaptation unit 10 through the shoulder adaptation bodies 1321 and the shoulder base 131 (of course, the spinal locomotion adaptation unit 10 can also further transmit the gravity to the lower limb supporting unit of the exoskeleton), thereby realizing auxiliary assisting transportation of single-person longitudinal carrying of the burdens (or heavy rods and heavy pies) or multi-person longitudinal (front-rear) cooperation of carrying the burdens (or heavy rods and heavy pies). In addition, the longitudinal grooves 1323 on the left and the right sides can also be used together to realize such a transportation manner that two persons cooperate to carry the burdens, or more wearers cooperate to carry a variety of heavy materials. That is, the design of the shoulder supporting piece 13 in the present embodiment allows the user to realize a variety of transportation manners (such as, transverse and longitudinal carrying or bearing of the burdens), thereby alleviating the problem of the prior art passive exoskeleton device that can only be utilized for a single application. Of course, the shoulder weight-bearing platforms 132 in the present embodiment may also not employ such a manner that transverse/longitudinal grooves are formed on the shoulder adaptation bodies 1321, or groove brackets may be arranged on the shoulder adaptation bodies 1321 in a detachable manner or a rotatable manner around a fixed axis. Thus, one groove bracket can realize transverse, longitudinal or oblique transportation of tubular objects. Or, supporting brackets that can rotate around two axes are put on equipment or instruments to be carried on the shoulder and regulated at a pointing angle. The brackets can also be further designed to have a stabilizing platform driven and controlled by a motor for controlling and stabilizing the direction of the equipment.

In a specific embodiment, with reference to FIG. 4a, the shoulder base 131 of the shoulder supporting piece 13 and the two shoulder weight-bearing platforms are integrated in one piece and are connected in such a manner that the shoulder base 131 can move up and down relative to the spinal locomotion adaptation unit 10, so as to regulate the height of the shoulder supporting piece 13 to adapt to human bodies with different back lengths. Specifically, a wedge groove is arranged at the bottom of the shoulder base 131. The top of the spinal locomotion adaptation unit 10, such as the top of the flexible body 101 or the top of the elastic backplane 102, can be inserted into the wedge groove, and fixing holes with different heights are arranged in the wedge groove to regulate the height of the shoulder platforms to adapt to human bodies with different back lengths (in some embodiments, the fixing holes can also be arranged on the elastic backplane or flexible body). Further, a sliding rail and a locking unit are arranged in the wedge groove at the lower end of the shoulder base 131, and the upper end of the elastic backplane 102/flexible body 101 can slide along the sliding rail in the wedge groove at the lower end of the shoulder base 131 and is locked by the locking unit. That is, the distance that the elastic backplane 102/flexible body 101 slides in the rail can be regulated. When the elastic backplane 102/flexible body 101 slides to a required distance, the elastic backplane 102/flexible body 101 is locked by the locking unit. That is to say, by arranging the sliding rail in the wedge groove at the lower end of the shoulder base 131, the vertical attaching length of the back-carrying assisting unit and the back of the wearer can be regulated to meet the wear requirements of the wearers of different heights.

Figure 5B:
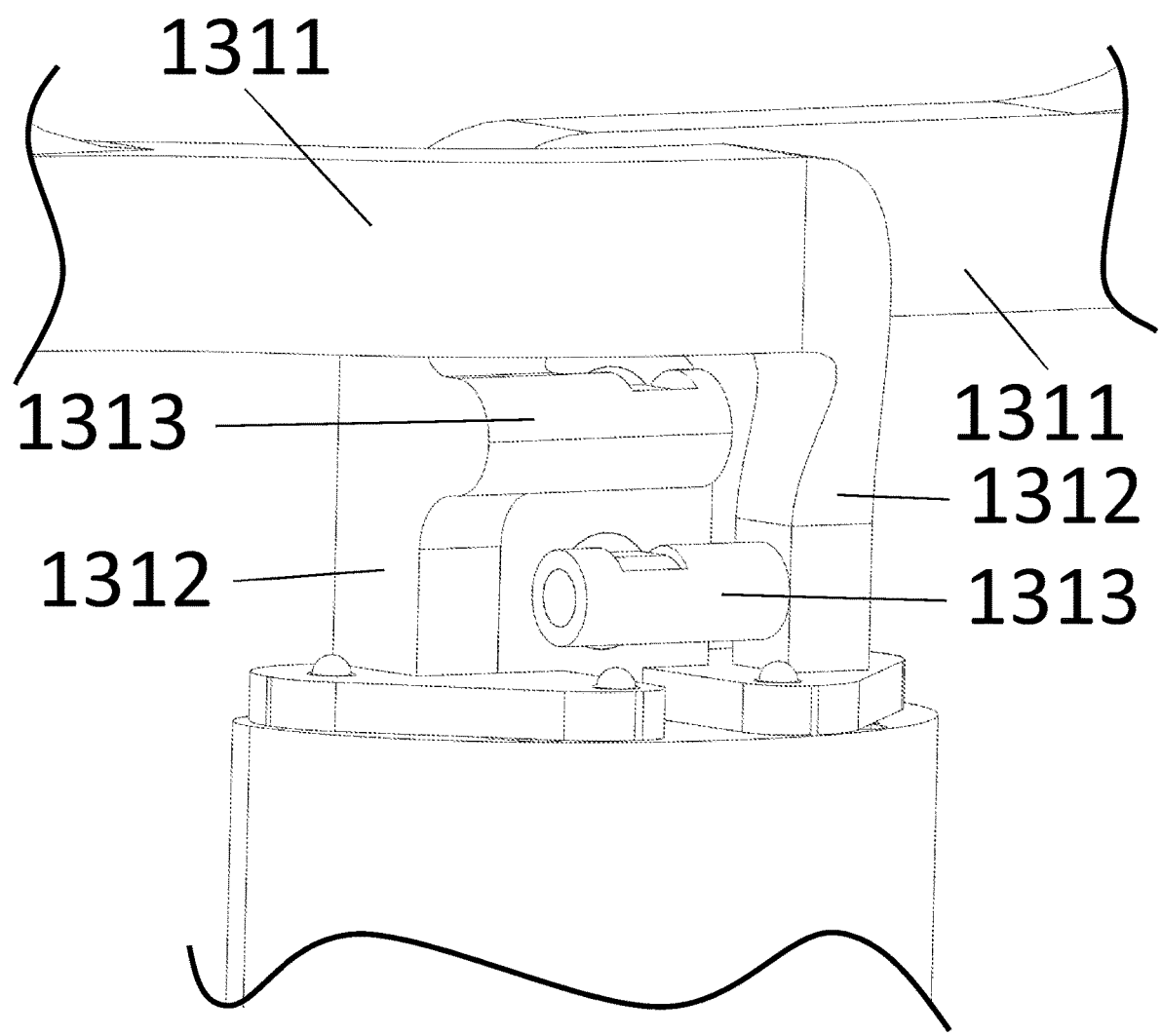

In another specific embodiment, with reference to FIG. 5a, the shoulder base 131 comprises two first connecting arms 1311 respectively connected with the left and the right shoulder weight-bearing platforms, and two second connecting arms 1312 respectively connected with the spinal locomotion adaptation unit 10; and the first connecting arms 1311 and the second connecting arms 1312 are connected (there is circular arc transition at the connection, or the first connecting arms and the second connecting arms are integrated in one piece), so that the second connecting arms 1312, the first connecting arms 1311 and the shoulder weight-bearing platforms 132 are connected in sequence to form cantilever units which are located above the spinal locomotion adaptation unit 10. Specifically, each of the left and the right second connecting arms 1312 is provided with a hinging seat 1313. The top of the flexible body 101 (or the elastic backplane 102) is provided with two hinging seats 1313 in parallel along the vertical direction. When the left and the right cantilever units are arranged on the spinal locomotion adaptation unit 10, the hinging seats 1313 on the two second connecting arms 1312 are staggered up and down, as shown in FIG. 5b. Therefore, when two "T"-shaped hinging heads are used for hinging, one end of each hinging head is hinged to the hinging seats on the flexible body 101 (or the elastic backplane), and the other end is connected to the hinging seats on the second connecting arms, so that two cantilevers are hinged to the spinal locomotion adaptation unit 10.

Embodiment 4

As mentioned above, most of the existing exoskeletons employ the back-carrying manner to handle the materials. Some exoskeletons can employ a front-handling manner, but it is difficult to cooperate with the back-carrying manner. In view of this, the present invention provides an exoskeleton which comprises a front-carrying assisting unit 2, a force transmission unit 3 and a back-carrying assisting unit 1. The front-carrying assisting unit 2 is connected with back-carrying assisting unit 1 through the force transmission unit 3 to form a force balance back-carrying unit. Thus, the weight of a front-carrying load is transmitted to the back-carrying assisting unit 1 through the front-carrying assisting unit 2 and the force transmission unit 3 to cooperate with the back-carrying assisting unit 1.

The front-carrying assisting unit 2 comprises a left and a right contactors 21.

Figure 6A:
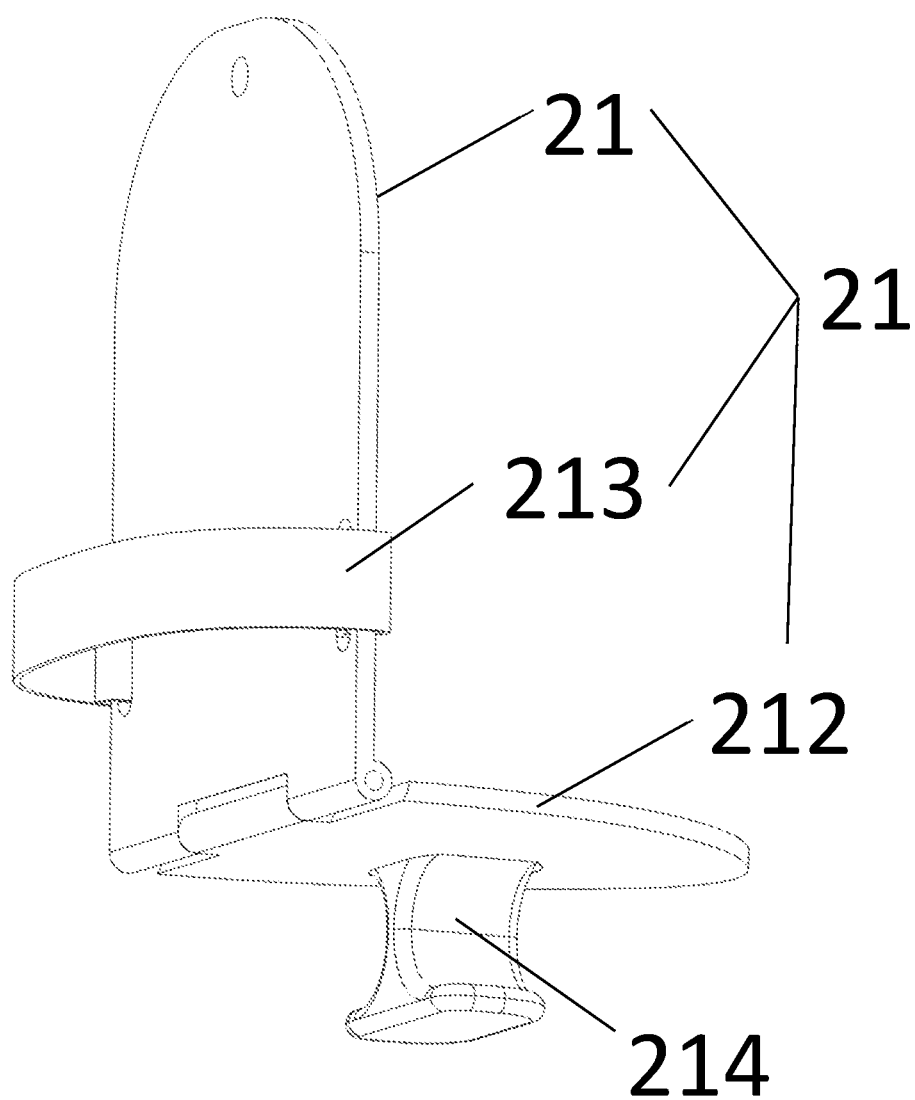
FIG. 6a, FIG. 6b and FIG. 6c are respectively structural schematic diagrams that reflect three embodiments of a contactor in a front-carrying assisting unit in an exoskeleton in the present invention.

In a specific embodiment, with reference to FIG. 6a, the contactor 21 comprises a palm supporting cushion 211, a finger supporting cushion 212 and a wearable component 213, wherein one end of the palm supporting cushion 211 is connected with the fixed end of the force transmission component 31, and the other end is hinged with the finger supporting cushion 212; and the wearable component 213 is arranged on the palm supporting cushion 212. Further, the back surface of the finger supporting cushion 212 is also provided with a clamping part 214 used for clamping between two fingers.

Figure 6B:
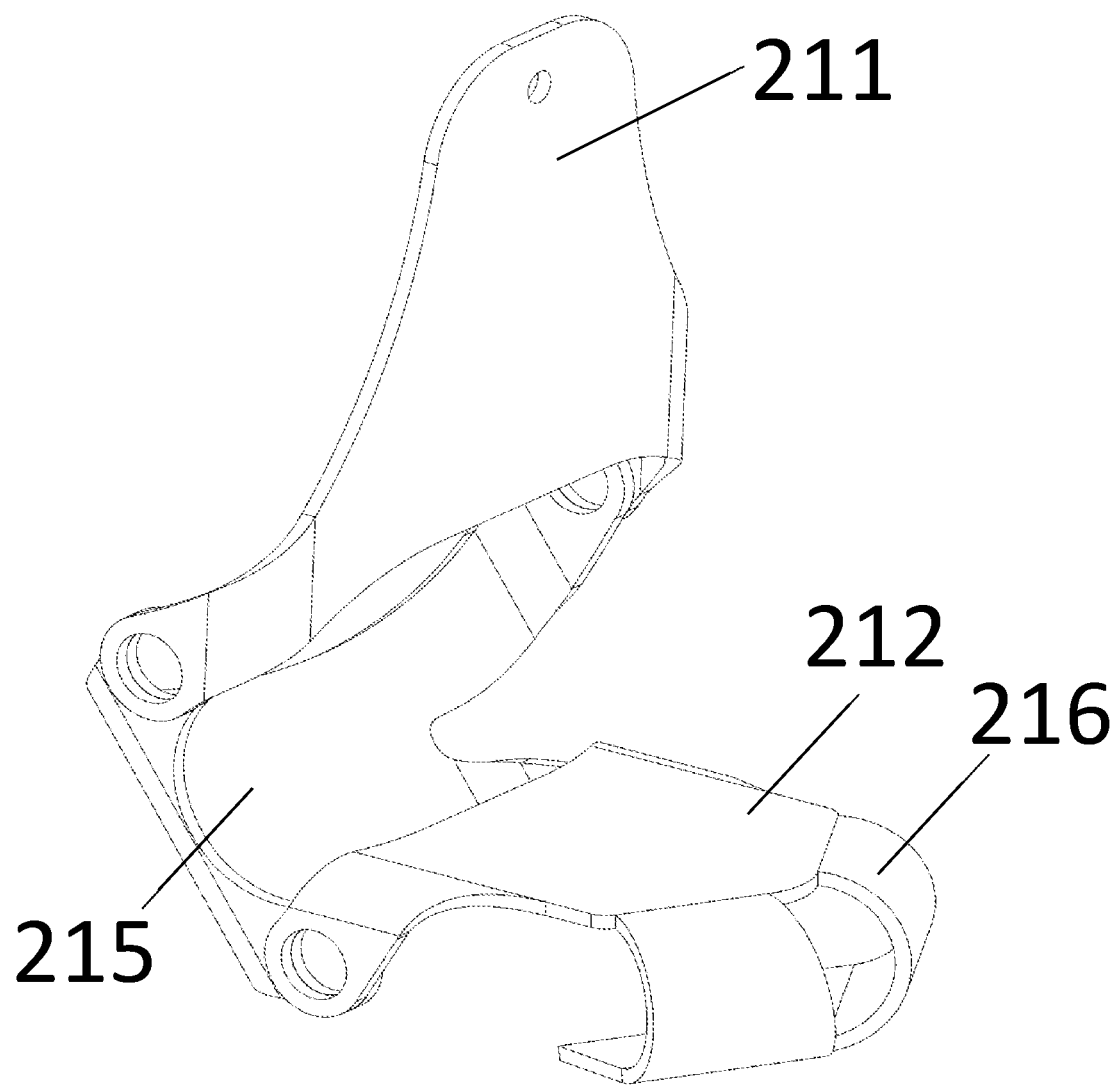

In another specific embodiment, with reference to FIG. 6b, in addition to the palm supporting cushion 211 and the finger supporting cushion 212, the contactor 21 comprises a finger connecting piece 215, and the palm supporting cushion 211 and the finger supporting cushion 212 are respectively hinged with both ends of the finger connecting piece 215, and the palm supporting cushion 211 is also connected with the fixed end of the force transmission component 31. Further, each of the contactors 21 also comprises a fingertip protecting cover 216 arranged at the end of the finger supporting cushion 212.

Figure 6C:
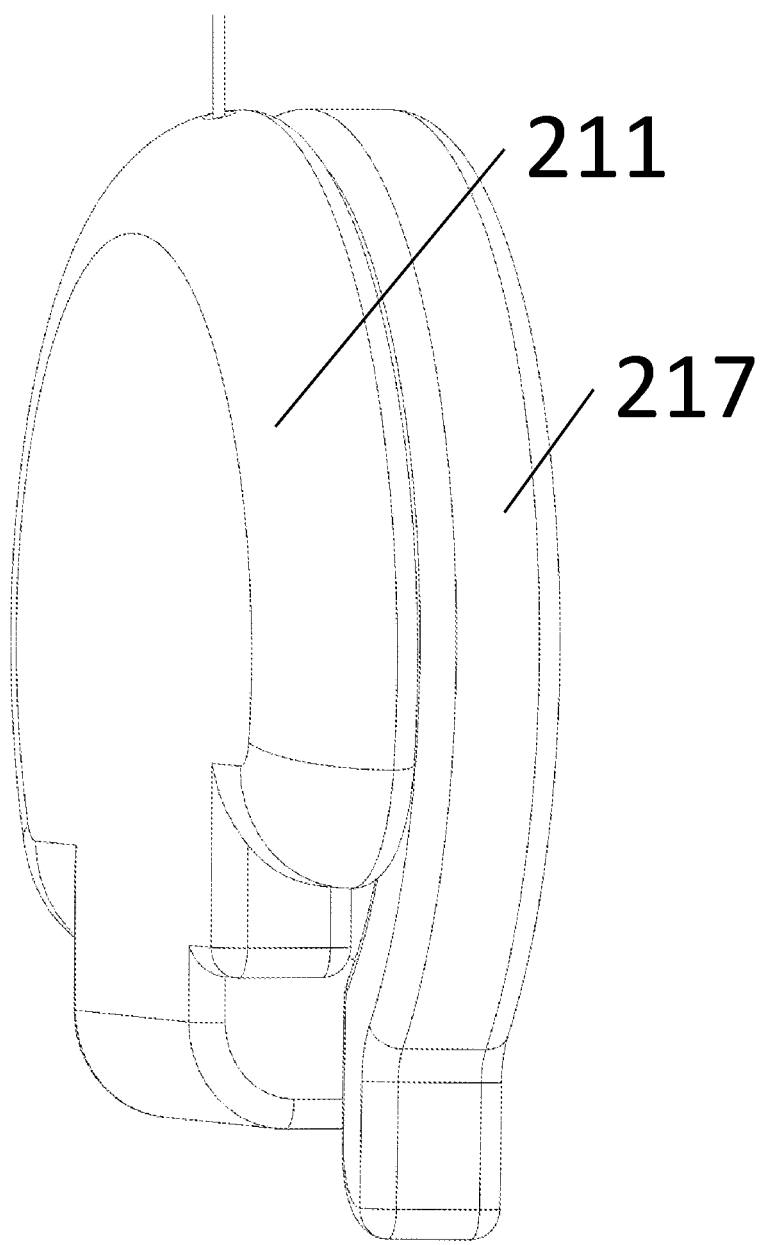
Figure 6D:
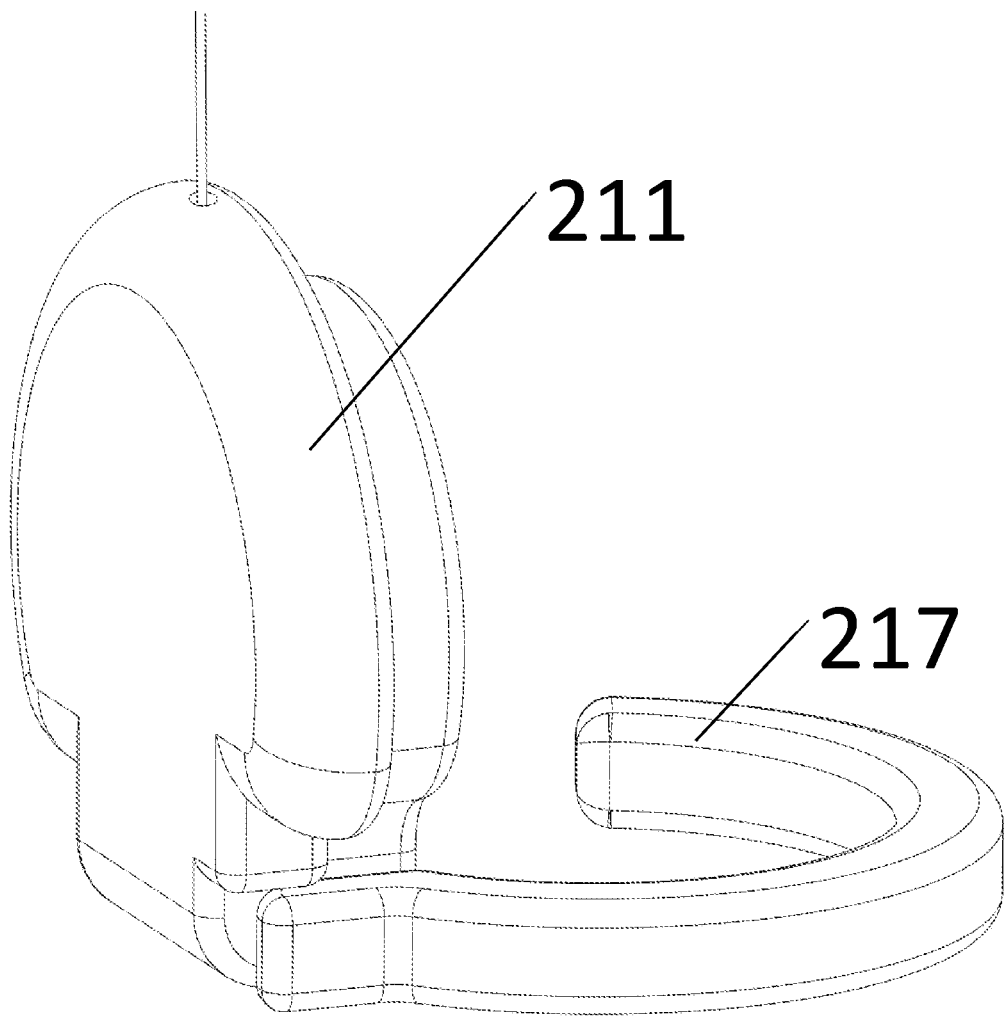
FIG. 6d and FIG. 6e are respectively structural schematic diagrams that reflect different states of a contactor in FIG. 6c.
Figure 6E:
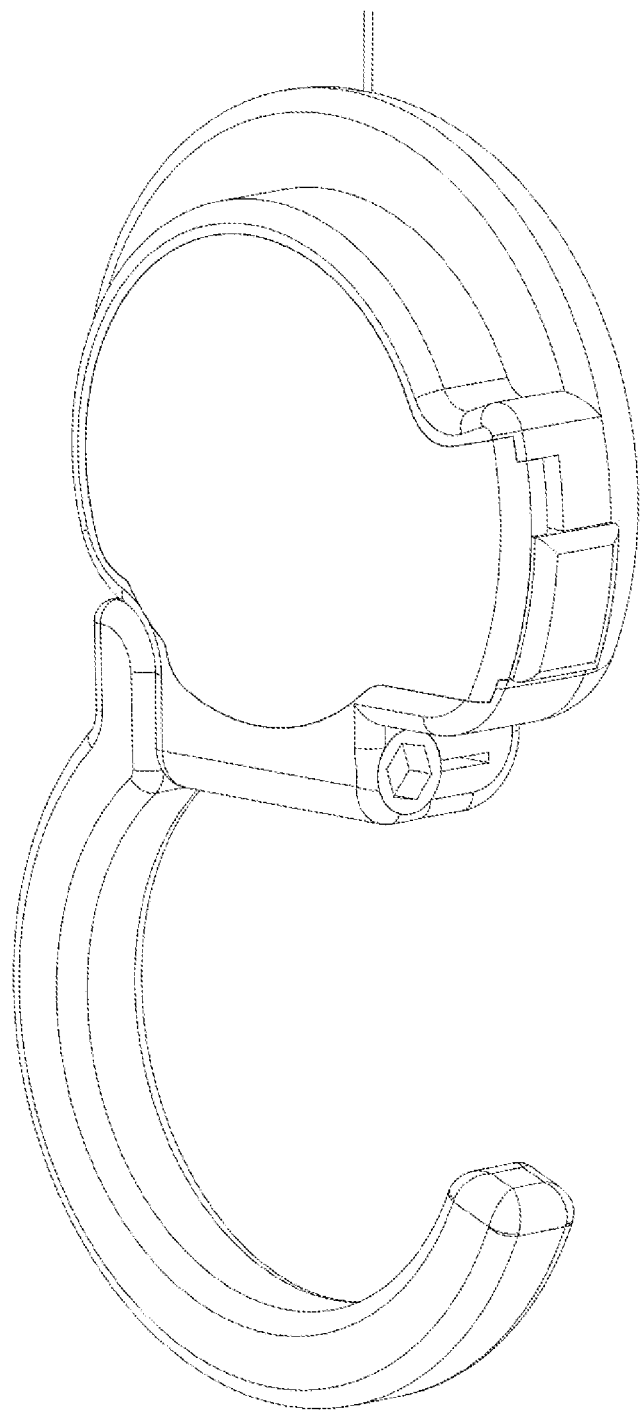

In another specific embodiment, with reference to FIG. 6c, each contactor 21 comprises a palm supporting cushion 211 and a hooked weight-bearing part 217; one end of the hooked weight-bearing part 217 is rotatably connected with the palm supporting cushion 211; and the palm supporting cushion 211 is provided with an accommodating groove with an L-shaped cross section, as shown in FIG. 6d. In an initial state, the hooked weight-bearing part 217 is located on the accommodating groove to form, with the palm supporting cushion 211, a surface contactor that can be attached to the side surface of the front-carrying load, as shown in FIG. 6c. Or, when the hooked weight-bearing part 217 rotates to be perpendicular to the vertical plane, the hooked weight-bearing part 217 and the palm supporting cushion 211 form a weight-bearing unit with an L-shaped cross section used for the front lifting of the load, as shown in FIG. 6d. Or, when the hooked weight-bearing part 217 rotates to be parallel to the vertical plane, the hooked weight-bearing part 217 is used to lift the load, as shown in FIG. 6e.

The force transmission unit 3 comprises a left and a right force transmission components 31 and a left and a right contraction devices 32 having self-locking units. One end of each of the left and the right force transmission components 31 is respectively twined into the left and the right contraction devices 32; and when the self-locking units in the contraction devices 32 are unlocked, the contraction devices 32 release the force transmission components 31 twined into the contraction devices 32; and when the other end of each of the left and the right force transmission components 31 is respectively fixedly connected with the left side and the right side of the shoulder supporting piece of the back-carrying assisting unit 1 (e.g., respectively fixed to the front ends of the left and the right shoulder weight-bearing platforms), the left and the right contraction devices 32 are accordingly fixed to the left side and the right side of the front-carrying assisting unit respectively, e.g., respectively fixed to the left and the right contactors. In addition, in the present embodiment, the other end of each of the left and the right force transmission components 31 can also be respectively fixed to the left side and the right side of the front-carrying assisting unit 2, and the left and the right contraction devices 32 are respectively fixed to the left side and the right side of the back-carrying assisting unit 1 (e.g., embedded into the left and the right shoulder weight-bearing platforms).

Figure 7A:
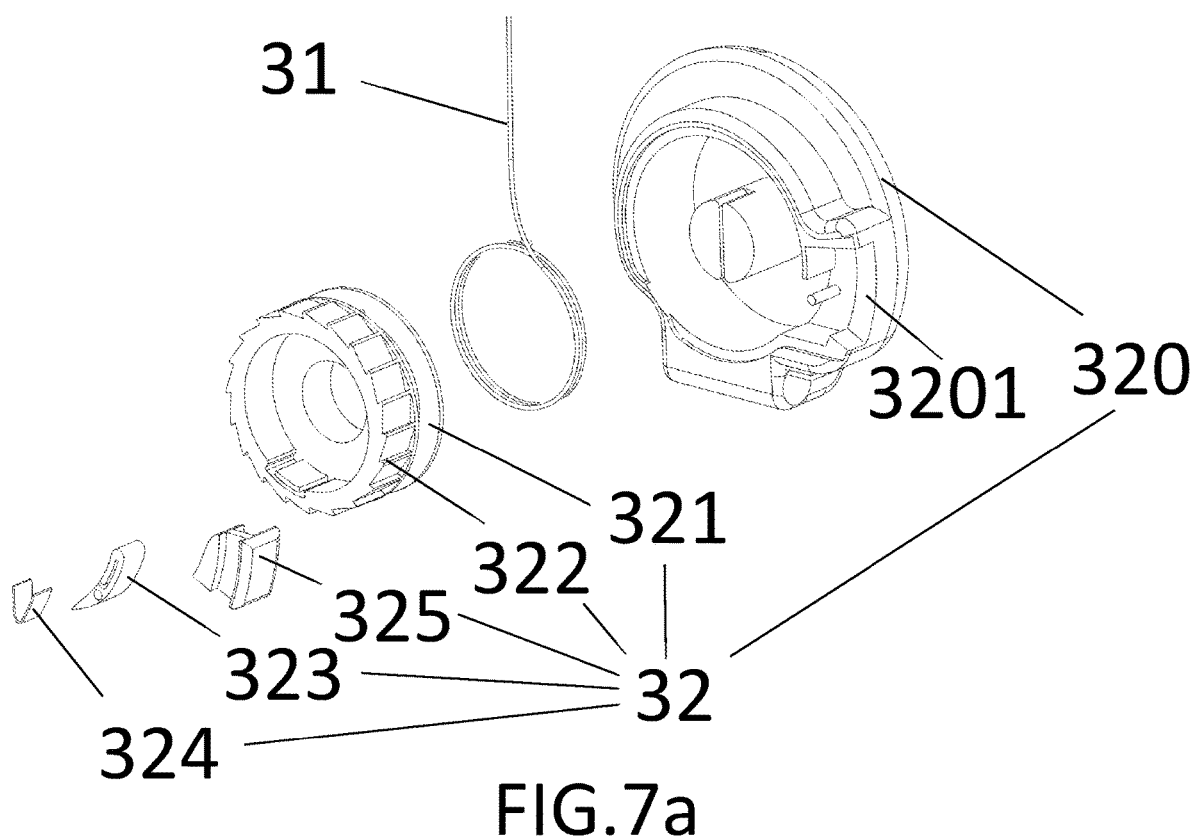
FIG. 7a is an exploded drawing that reflects a contraction device of an exoskeleton in the present invention.
Figure 7B:
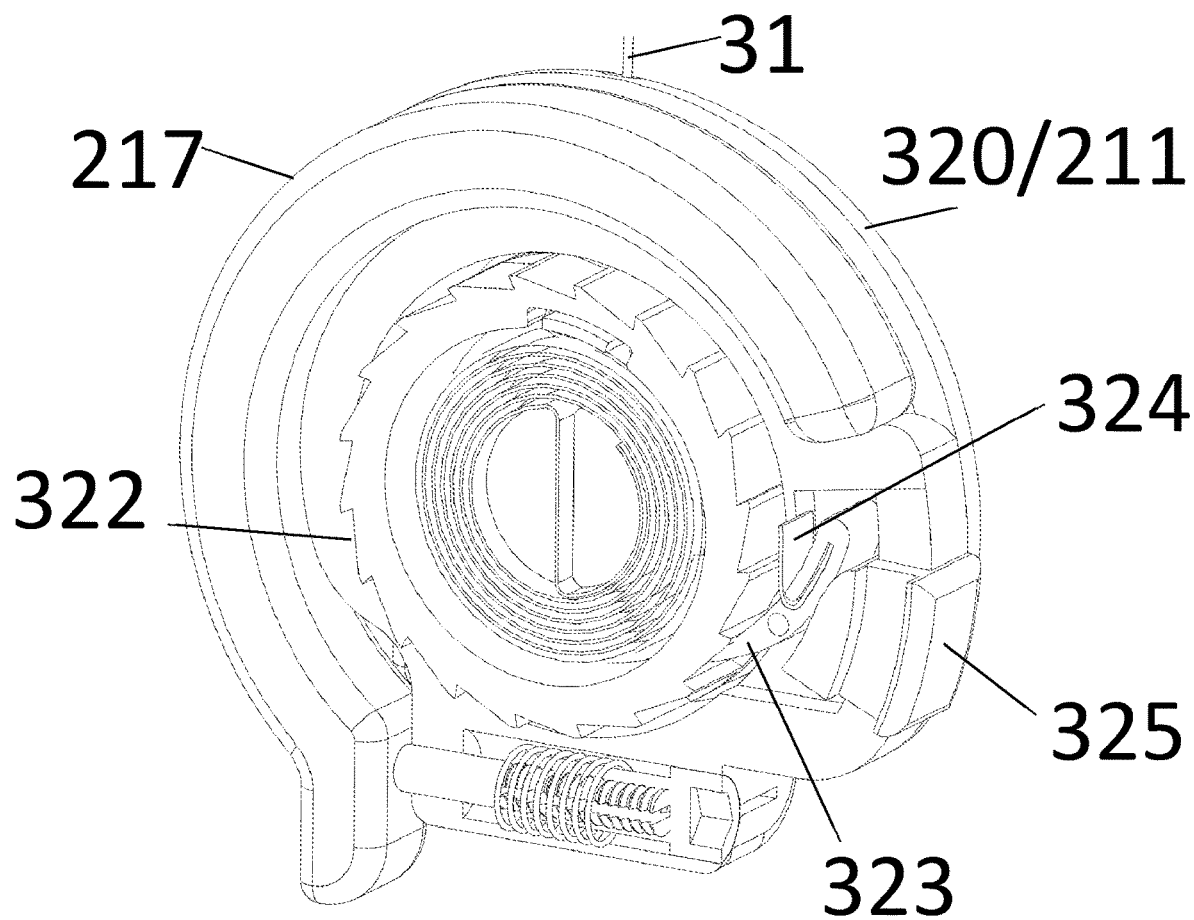
FIG. 7b and FIG. 7c are respectively a schematic diagram and an exploded drawing that reflect that a contraction device of an exoskeleton in the present invention is used as a contactor.
Figure 7C:
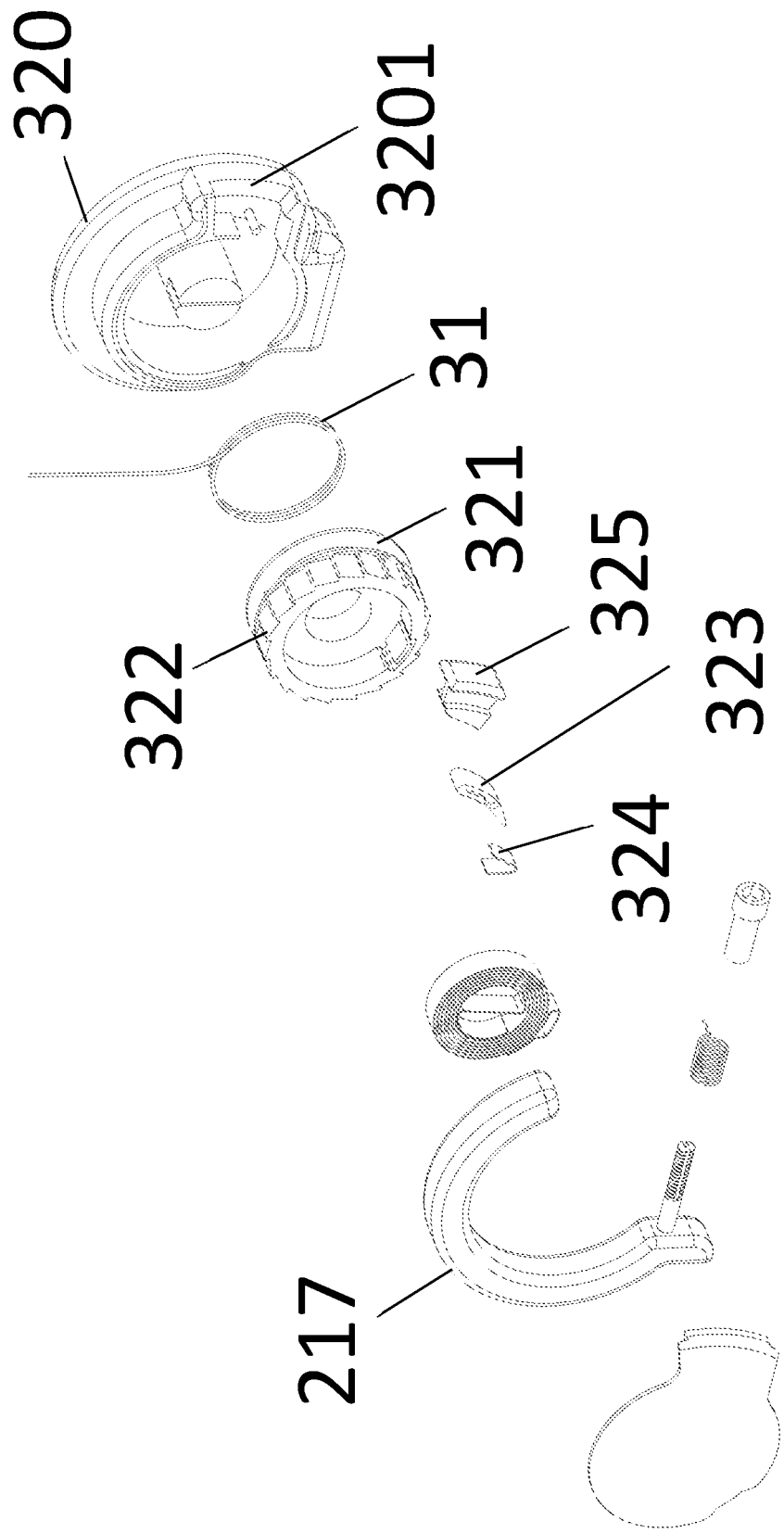
Figure 8A:
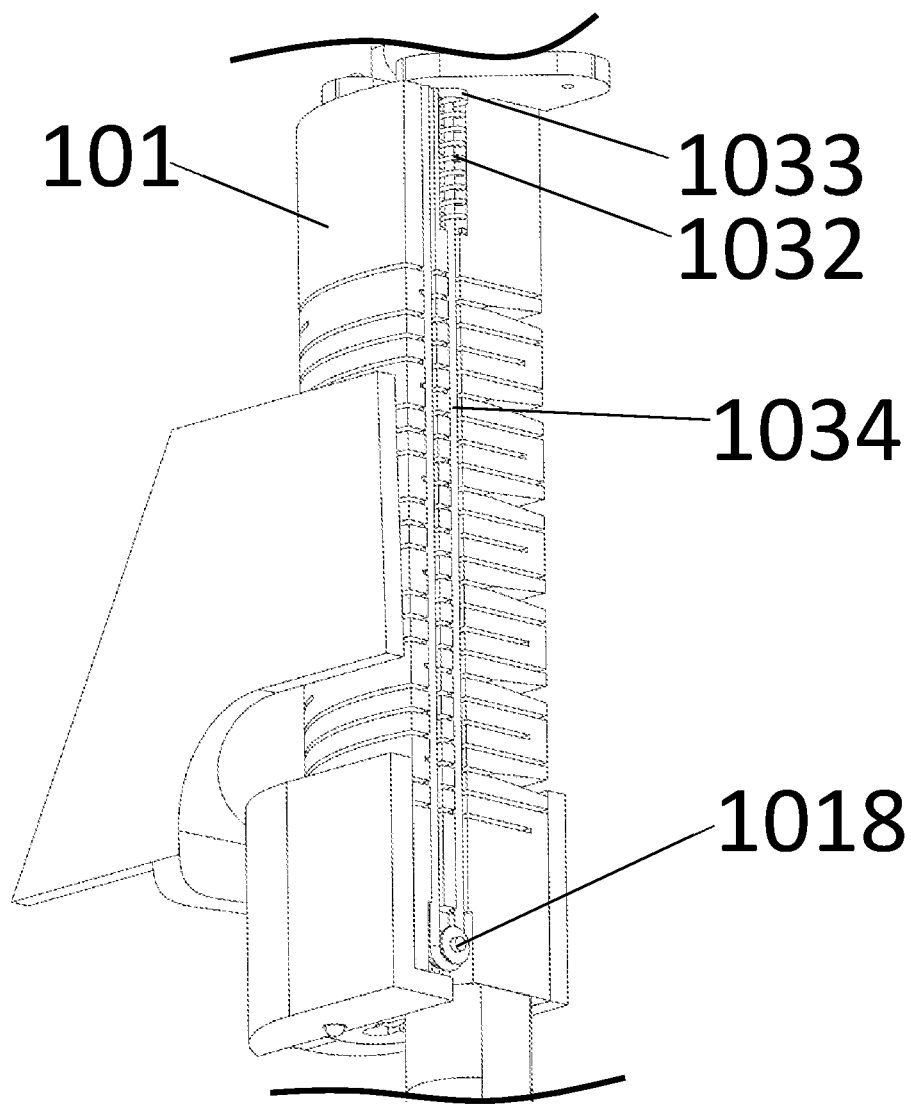
FIG. 8a, FIG. 8b, FIG. 8c and FIG. 8d are respectively schematic diagrams of a rigidity regulating unit in an exoskeleton in the present invention.
Figure 8B:
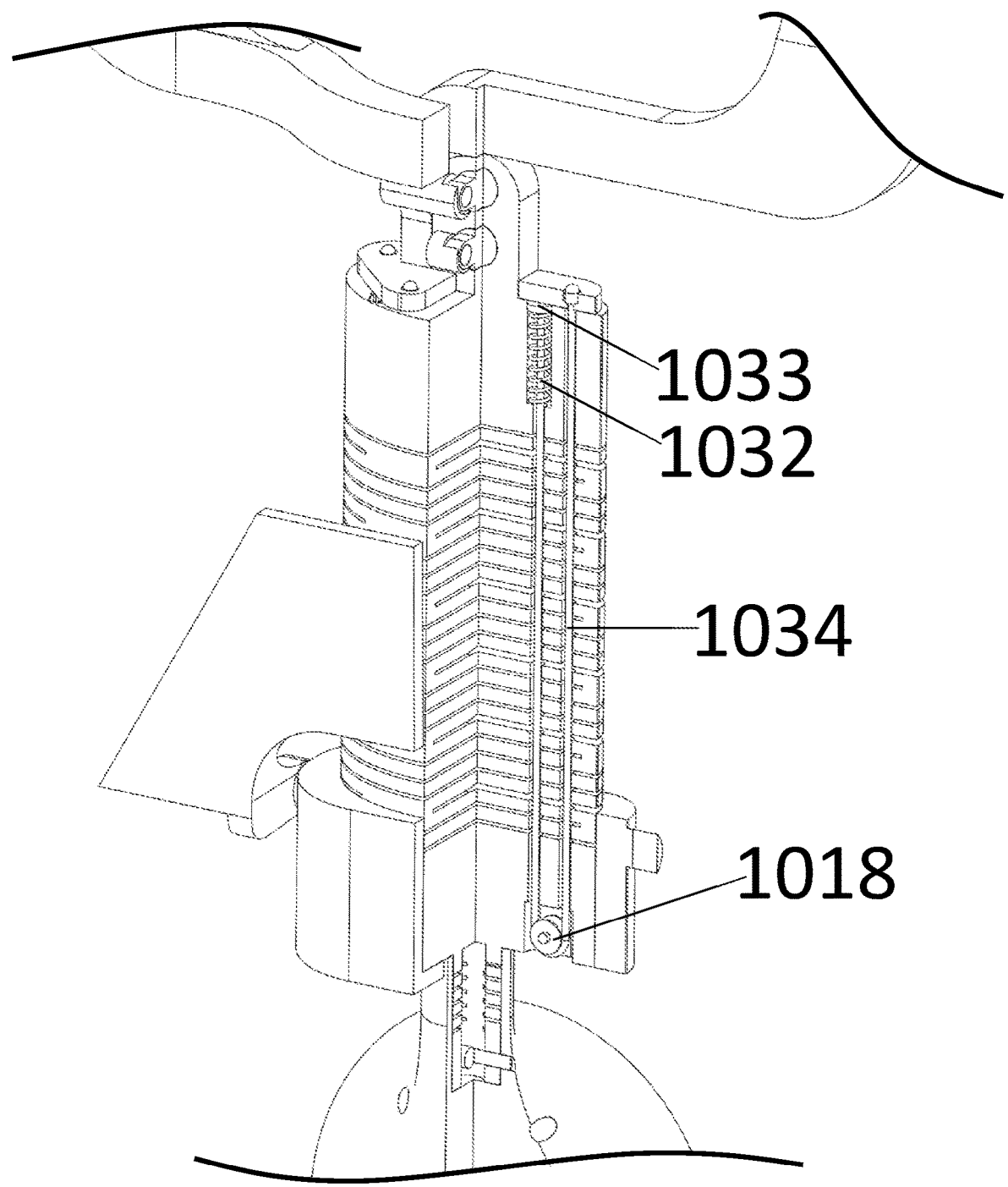
Figure 8C:
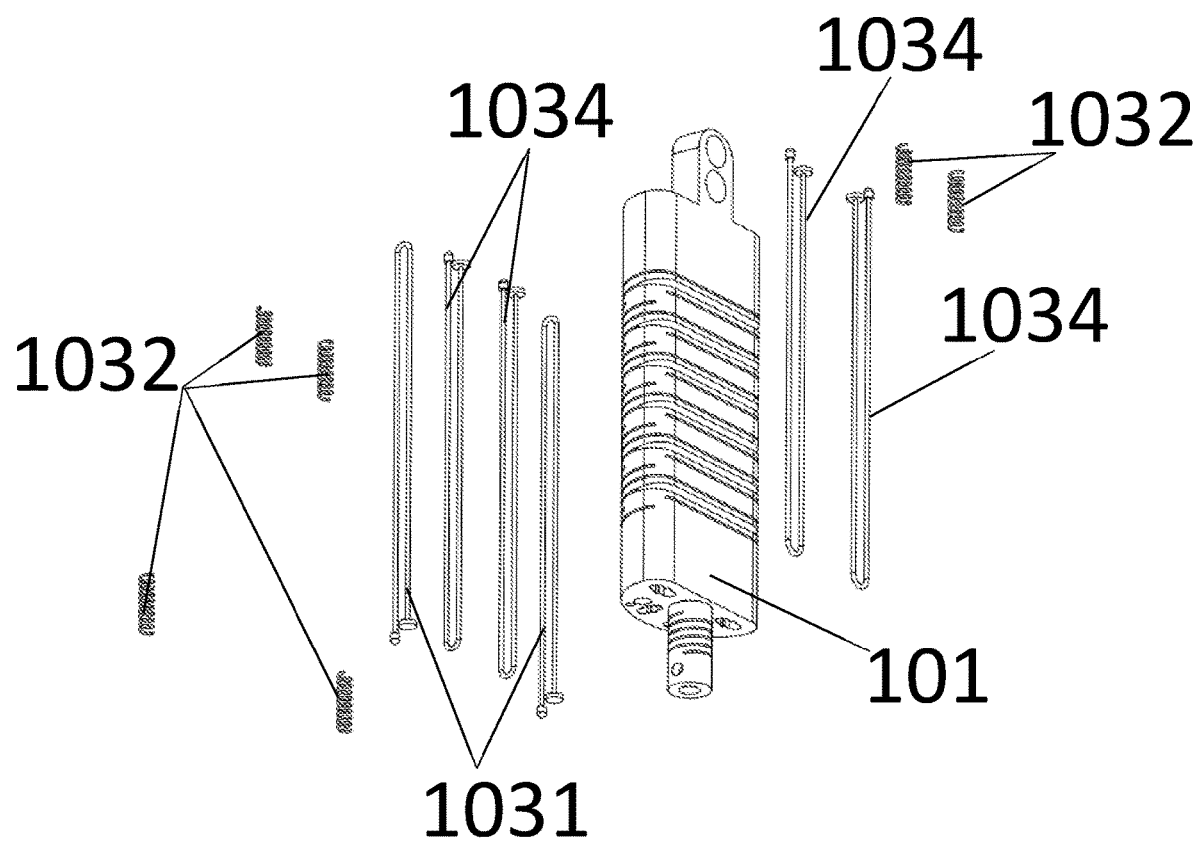

In a specific embodiment, with reference to FIG. 7a, each contraction device comprises a housing 320, a winding reel 321 arranged in the housing 320 through a rotating shaft (one end of the force transmission component, such as the pull line, is twined around the winding reel 321), and a ratchet wheel 322 disposed coaxially with the winding reel 321. The housing 320 is provided with a pawl 323 matched with the ratchet wheel 322, and an elastic member 324 and an unlocking slider block 325 which are respectively located on two opposite sides of the pawl 323. In the initial state, when the unlocking slider block 325 is located at the top end (i.e., a self-locking region) in an unlocking slider block groove 3201 on the housing 320, the unlocking slider block 325 abuts against the pawl 323, so that the pawl 323 compresses the elastic member 324 and tightly abuts between the gears of the ratchet wheel 322, thereby achieving self-locking. When the unlocking slider block 325 slides to the bottom end (i.e., an unlocking region) in the unlocking slider block groove 3201, the unlocking slider block 325 does not abut against the pawl 323, so that the pawl 323 bears the acting force of the elastic member 324 and keeps away from the gears of the ratchet wheel 322, thereby achieving unlocking. In addition, in the present embodiment, the housing 320 of the contraction device 32 can also be directly used as the palm supporting cushion 211, and an accommodating groove for storing the hooked weight-bearing part 217 is arranged on the housing 320, as shown in FIG. 7b and FIG. 7c. The working principle is the same as that of the above contactor, and is not described herein. The back-carrying assisting unit 1 can adopt the back-carrying assisting unit 1 of any exoskeleton in the above embodiment 1, 2 or 3 (the same reference numerals indicate the same components, which will not be described herein). When the spinal locomotion adaptation unit 10 in the exoskeleton adopts the flexible body (a plurality of groups of spinal locomotion adaptation structures are arranged evenly on the flexible body from top to bottom along the lengthwise direction, and a rotation slot is arranged on the bottom), in addition to the two pull lines 1031 arranged in the flexible body 101, the first pull line passage 1016, the second pull line passage 1017, the pulley 1018, the elastic component 1032 and the head cover 1033 as recorded in embodiment 1 or 2 and as shown in FIG. 8a, FIG. 8b and FIG. 8c, the rigidity regulating unit on the flexible body 101 also comprises two force transmission lines 1034 used to transmit the front load. Accordingly, the left side and the right side in the flexible body 101 are provided with two third and fourth pull line passages 1019 and 1020 in parallel along the lengthwise direction (located between the above first group of pull line passages, i.e., the first and second left pull line passages 1016, 1017, and the second group of pull line passages, i.e., the first and second right pull line passages 1016, 1017). The fixed end of the force transmission line 1034 on the right is fixed to the top of the third pull line passage 1019 on the right, and the movable end of the force transmission line 1034 on the right penetrates into the third pull line passage 1019 on the right, penetrates out of the bottom of the third pull line passage 1019 on the right, then bypasses the pulley arranged between the right third pull line passage 1019 and the bottom of the fourth pull line passage 1020, penetrates from the bottom of the right fourth pull line passage 1020 and finally penetrates out of the top of the right fourth pull line passage 1020 to connect to the left side of the shoulder supporting piece 13 (e.g., connect to the bottom of the second connecting arm of the left cantilever). Similarly, the fixed end of the left force transmission line 1034 is fixed to the top of the left third pull line passage 1019, and the free end of the left force transmission line 1034 penetrates into the left third pull line passage 1019 and penetrates out of the bottom of the left third pull line passage 1019, and then bypasses a pulley 1018 arranged between the left third pull line passage 1019 and the bottom of the fourth pull line passage 1020, penetrates from the bottom of the left fourth pull line passage 1020 and finally penetrates out of the top of the left fourth pull line passage 1020 to connect to the right side of the shoulder supporting piece 13 (e.g., connect to the bottom of the second connecting arm of the right cantilever). That is, the left and the right force transmission lines 1034 respectively penetrate through the third pull line passage 1019 and the fourth pull line passage 1020 on the corresponding side in sequence, and penetrate out of the top of the fourth pull line passage 1020 on the corresponding side to respectively crosswise connect to the left side and the right side of the shoulder supporting piece 13 (i.e., the left force transmission line 1034 is connected with the right side of the shoulder supporting piece 13, and the right force transmission line 1034 is connected with the left side of the shoulder supporting piece 13). Thus, when the front-carrying assisting unit 2 carries a load, since the front-carrying assisting unit 2 transmits the gravity of the load to the shoulder supporting piece 13 through the force transmission unit 3, the two force transmission lines 1034 provide, for the shoulder supporting piece 13, an acting force against the gravity of the front-carrying load, thereby achieving the force balance. Moreover, because the force transmission lines 1034 pass through the flexible body 101 twice and apply the force to the flexible body at both ends by a pull line pulley and a pull line spring, when the front of the cantilever of the shoulder supporting piece 13 is pressed by the front load, the tensioning force of the force transmission line simultaneously tightens the rear portion of the flexible spine, thereby preventing the flexible body from being bent due to the presence of the arm of force when the cantilever is pressed by the front load.

Figure 8D:
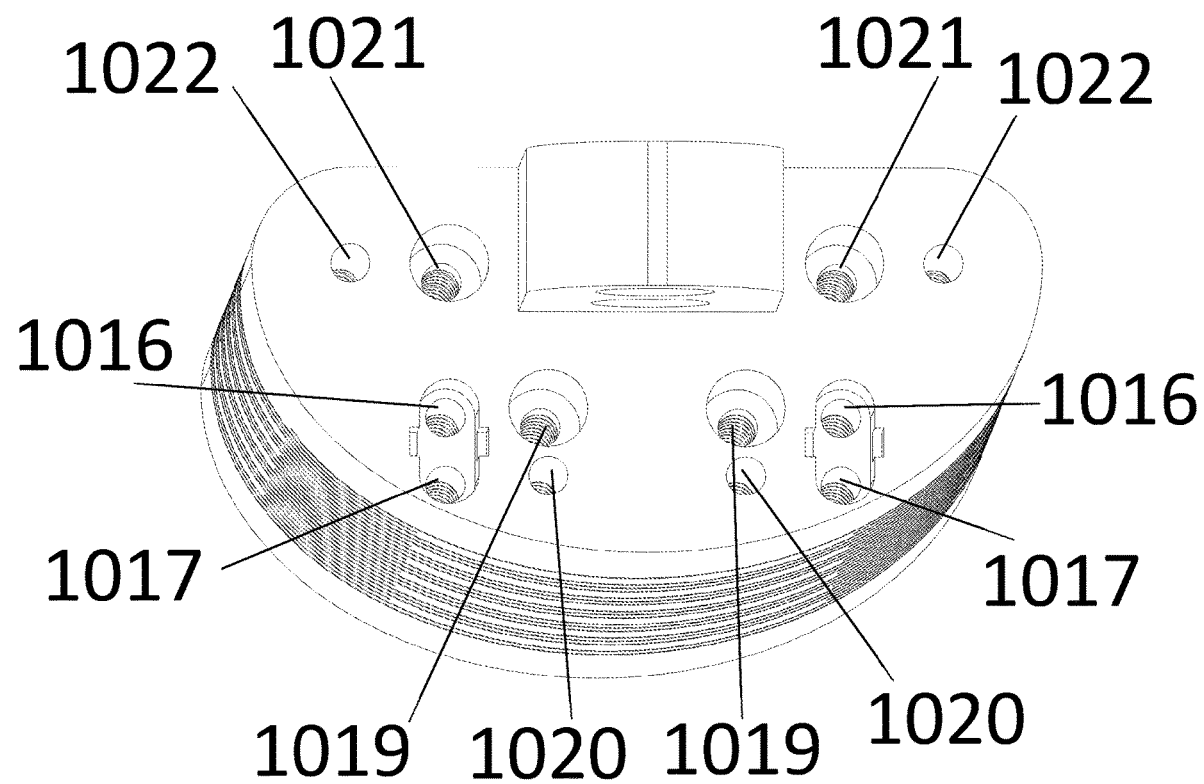

Further, in the present embodiment, the rigidity regulating unit also comprises two force transmission lines 1034. Accordingly, the internal part of the flexible body 101 is also provided with a fifth pull line passage 1021 and a sixth pull line passage 1022 side by side along the lengthwise direction at the left side and the right side of one side close to the back of the human body, and have the same connection manner and the same working principle as those of the above two force transmission lines 1034 and the third and the fourth pull line passages, which will not be described herein. That is to say, in the present embodiment, not only the left and the right force transmission lines 1034 and the corresponding third and fourth pull line passages are arranged on one side of the flexible body 101 away from the back of the human body, but also the left and the right force transmission lines and the corresponding fifth and sixth pull line passages are arranged on one side of the flexible body 101 near the back of the human body, as shown in FIG. 8*b*, FIG. 8*c* and FIG. 8*d*. Thus, a rear force transmission line and a side force transmission line are respectively arranged on the left side and the right side of the shoulder supporting piece 13 (such as the left cantilever and the right cantilever), thereby providing, for the shoulder supporting piece 13, a reaction force against the gravity of the load carried by the front-carrying assisting unit and also applying a force to the spine. In addition, in the present embodiment, a force transmission line and a corresponding pull line passage can also be added to the rigidity regulating unit. That is, at least two force transmission lines and at least two corresponding pull line passages may be arranged in the rigidity regulating unit.

As mentioned above, to perform a buffering role, with reference to FIG. 8*a* and FIG. 8*b*, an elastic component 1032 is also fixed to the fixed end of the force transmission line 1034 in the present embodiment (specifically, the elastic component 1032 is a spring; accordingly, a head cover 1033 is connected to the fixed end of the force transmission line 1034 to fix the head cover 1033 to one end of the spring, and the free end of the force transmission line 1034 penetrates through the spring and enters the corresponding pull line passage). Thus, when the force transmission line 1034 is pulled, the force transmission line 1034 first compresses the elastic component 1032, and the elastic component 1032 reacts on the flexible body 101 to compress each group of spinal locomotion adaptation structure until the reaction force of the elastic component and the pulling force of the force transmission line 1034 achieve the force balance.

Of course, in another specific embodiment, it can be understood that, the free ends of the two force transmission lines 1034 may also not be connected with the shoulder supporting piece 13, and the free ends of the two force transmission lines 1034 are directly pulled manually by the wearer, thereby compressing the groups of spinal locomotion adaptation structures and improving the rigidity of the flexible body.

Embodiment 5

Most of the existing exoskeletons are assembled as a whole, and are difficult to quickly disassemble and assemble during storage into a plurality of independent modules for separate storage, which takes up a lot of space. In wearing, various parts of the entire exoskeleton are worn in sequence, which is tedious. If one part is wrong, other parts cannot be correctly worn or even cannot be worn. When a part is damaged, it is usually returned to the factory for repair, instead of returning a separate module to the factory for repair or directly replacing this part. This part cannot be used by the user continuously during the repair, which not only increases the maintenance cost of the user or the manufacturer, but also reduces the user experience. Therefore, the present invention also provides an exoskeleton which comprises quick-release joints 5 that can rotate at single degree of freedom/three degrees of freedom, can bear weight and have the functions of damping and resilience for modularizing each part of the exoskeleton and standardizing the interface, thereby facilitating disassembling and assembling, storage and wear on the basis of ensuring that various joints of the exoskeleton have the functions of rotation, weight bearing, damping and resilience. Specifically, in the present embodiment, the quick-release joints are single-axis units to realize rotation at single degree of freedom, or three single-axis units are combined to realize rotation at three degrees of freedom.

Figure 9:
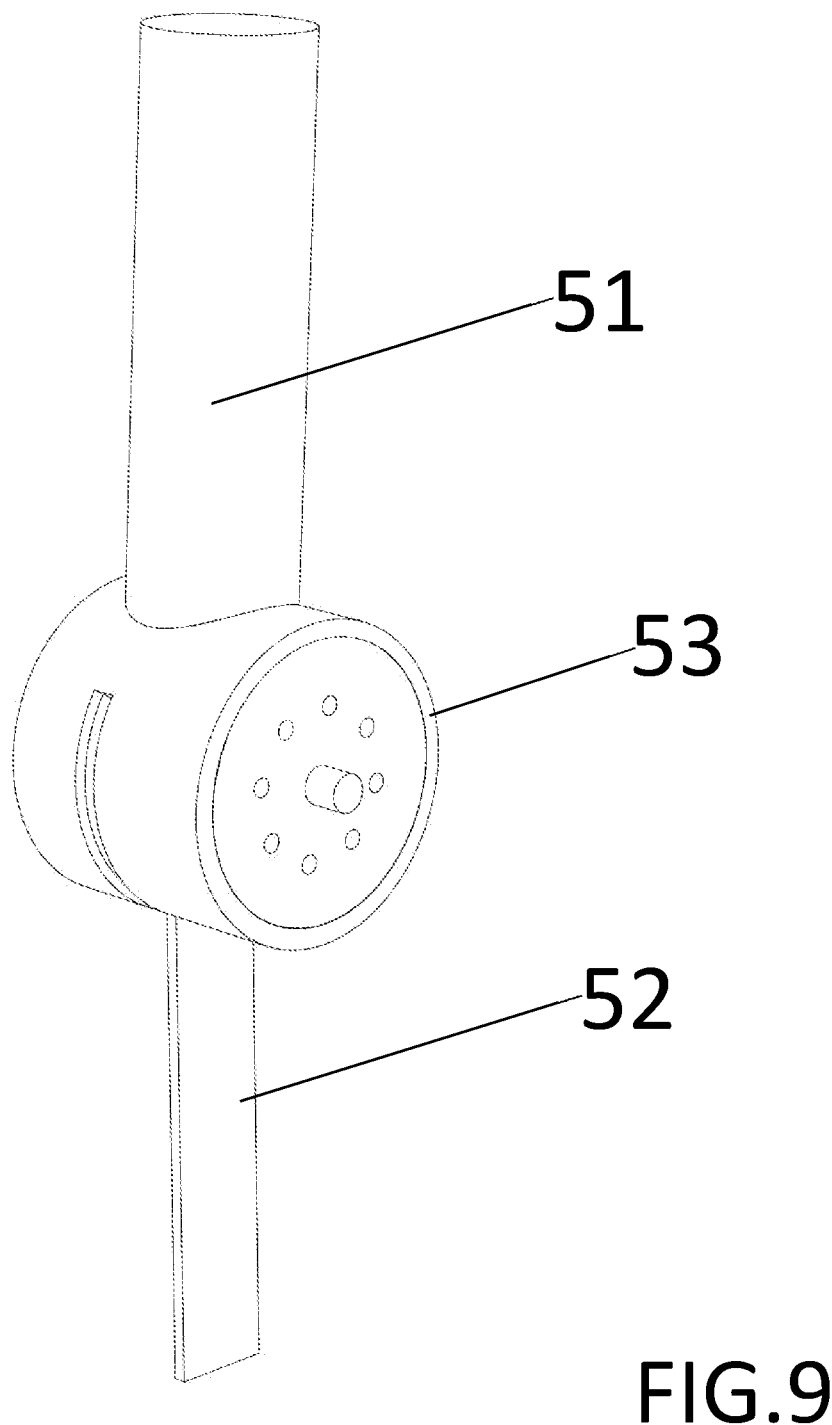
FIG. 9 is a structural schematic diagram of an embodiment of a quick-release joint of an exoskeleton in the present invention.

When the quick-release joints are the single-axis units, with reference to FIG. 9, the quick-release joints 5 comprise a first connecting rod 51 and a second connecting rod 52. One end of the first connecting rod 51 is provided with a quick-release end 53, and one end of the second connecting rod 52 is provided with a quick-release connector 54; and the quick-release connector 54 is rotatably connected with the quick-release end 53.

Figure 10A:
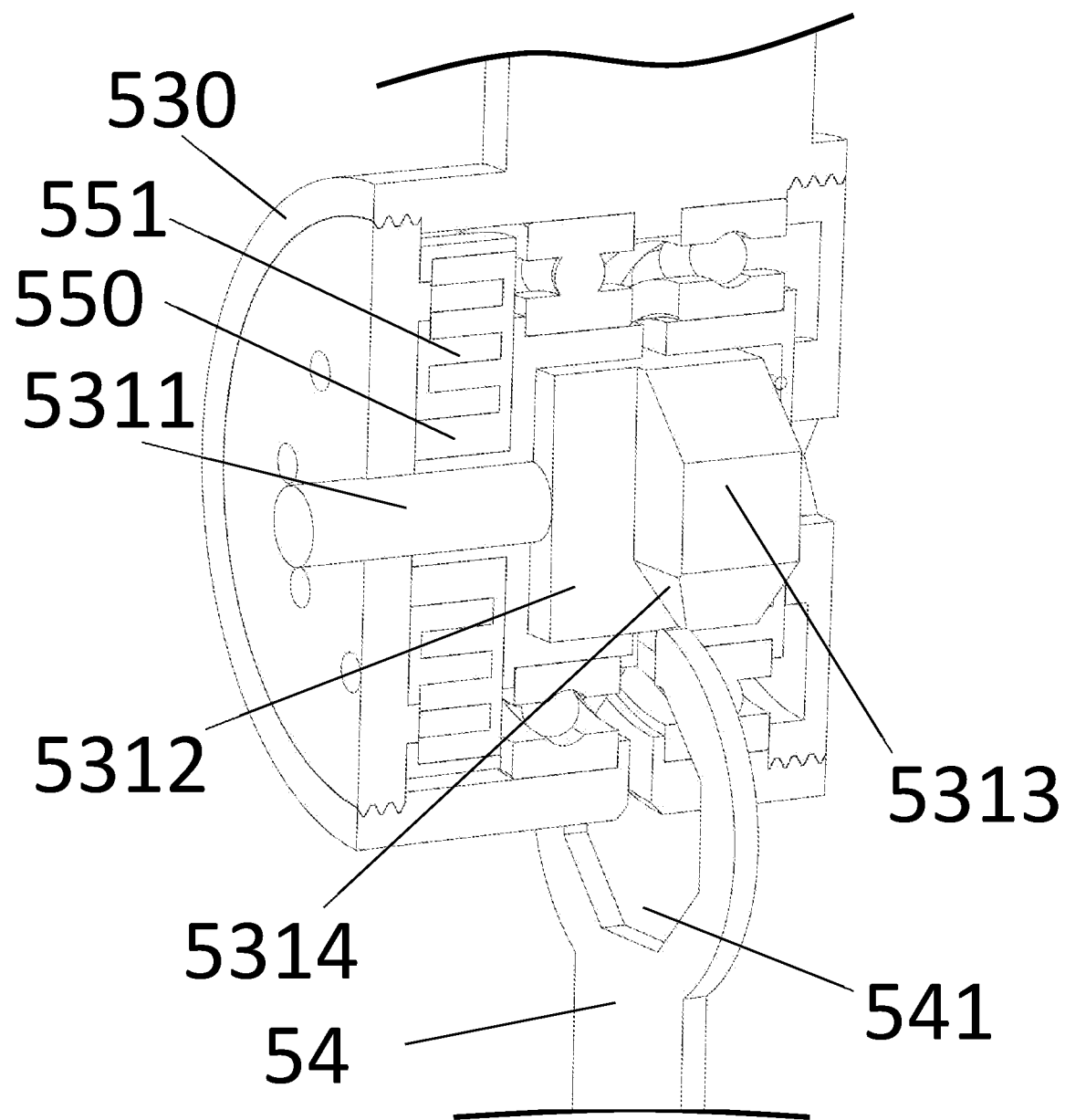
FIG. 10a is a schematic diagram that reflects an internal structure of a quick-release joint in FIG. 9.
Figure 10B:
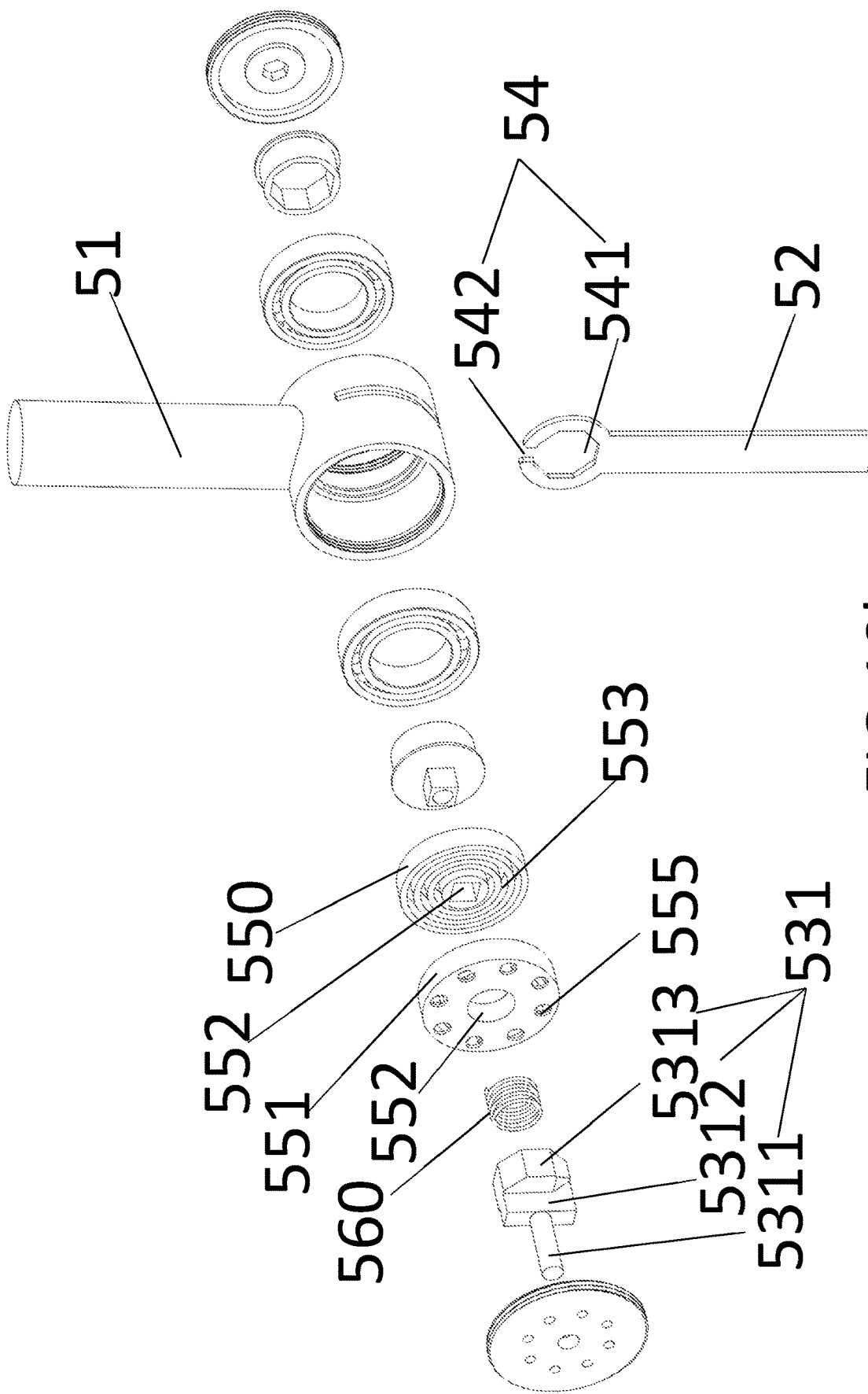
FIG. 10b and FIG. 10c are exploded drawings of a quick-release joint in FIG. 9.
Figure 10C:
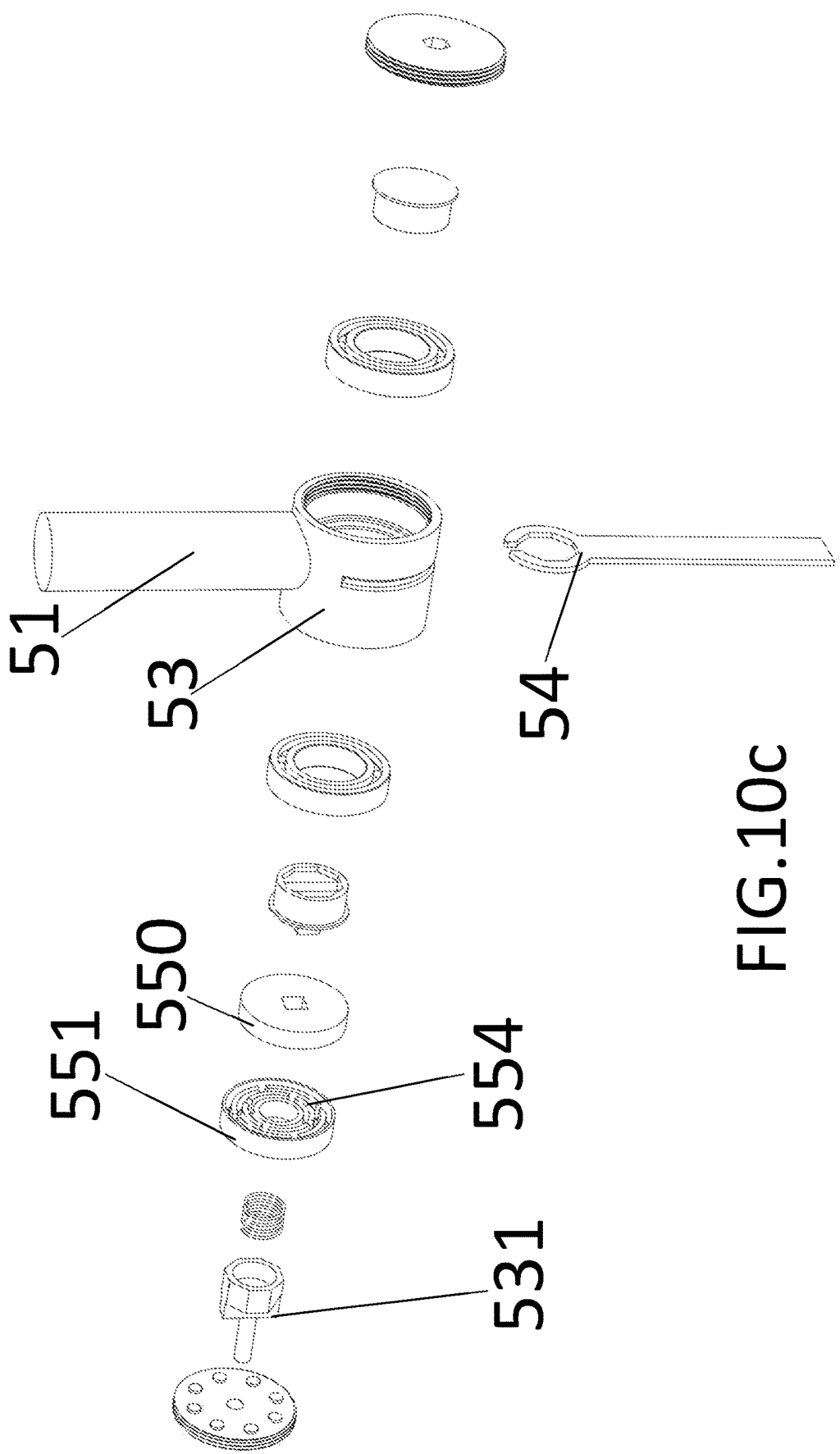

In a specific embodiment, with reference to FIG. 10*a*, FIG. 10*b* and FIG. 10*c*, the quick-release end 53 comprises a housing 530, and a quick-release button 531 which is installed in the housing 530 in a rotatable manner relative to the housing 530. The quick-release button 531 comprises a contact part 5311 for the wearer to press. One end of the contact part 5311 penetrates out of the housing, and the other end is sequentially connected with an unlocking part 5312 for unlocking the quick-release connector 54 from the quick-release end 53, and a locking part 5313 for positioning the quick-release connector 54 (the locking part is rotatably connected into the housing). Specifically, the unlocking part 5312 is a rectangular or square slider block. The locking part

5313 is in the shape of an octagon nut, and the width of the bottom thereof is gradually reduced, thereby forming a wedge surface 5314 at the bottom. Accordingly, the quick-release connector is provided with an inner octagon hole 541 matched with the locking part 5313, and a notch 542 is arranged on the top. When the quick-release connector 54 is inserted from a quick-release insertion hole on the housing 530, both sides of the top notch 542 gradually move upwards along the wedge surface 5314, thereby pushing the quick-release button 531 to entirely slide to the right. When both sides of the top notch 542 gradually transfer from the wedge surface to the top of the locking part 5313, the quick-release button 531 moves and resets to the left (under the action of a button resetting spring). At the same time, the inner octagon hole 541 of the quick-release connector 54 is fastened to the locking part 5313 so that the quick-release button 531 also rotates when the quick-release connector 54 rotates. When quick release is required, the contact part 5311 is directly pressed, so that the quick-release button 531 entirely moves to the right. That is, the locking part 5313 is removed from the inner octagon hole 541, so that the unlocking part moves into the inner octagon hole 541. At this point, the quick-release connector 54 slides off the surface of the unlocking part and then achieves quick release.

In another specific embodiment, with reference to FIG. 11a, FIG. 11b, FIG. 11c and FIG. 11d, a tenon quick-release hole 533 is arranged (on a quick-release bearing) inside the housing 530 of the quick-release end 53, and the inner octagon hole 541 and the top notch 542 are not arranged on the quick-release connector 54, but a tenon 544 is arranged on the quick-release connector 54. The quick-release button 531 is arranged in the tenon 544. A ball is arranged at the end of the tenon 544, and a ball groove 543 is also arranged at the end of the quick-release button 531. When the quick-release button 531 is pressed, the ball groove 543 moves to the lower part of the ball, so that the ball falls into the ball groove 543 and then the tenon can be inserted into or can slide out of the tenon quick-release hole 533. After the tenon is inserted, there is no need to press the quick-release button. Further, the end of the tenon quick-release hole 533 is provided with a ball locking groove 532, so that when the tenon 544 is inserted into the tenon quick-release hole 533, and the ball moves to the position of the ball locking groove 532, the tenon ejects the ball into the ball locking groove 532 under the action of the resetting spring of the quick-release button, so that the first connecting rod and the second connecting rod are locked upwards on the single-degree-of-freedom rotating shaft. When quick release is required, the quick-release button is pressed so that the ball falls into the tenon or the ball groove on the quick-release button, and then the tenon is pulled out. At this time, the tenon can be directly extracted without pressing the button.

Figure 12A:
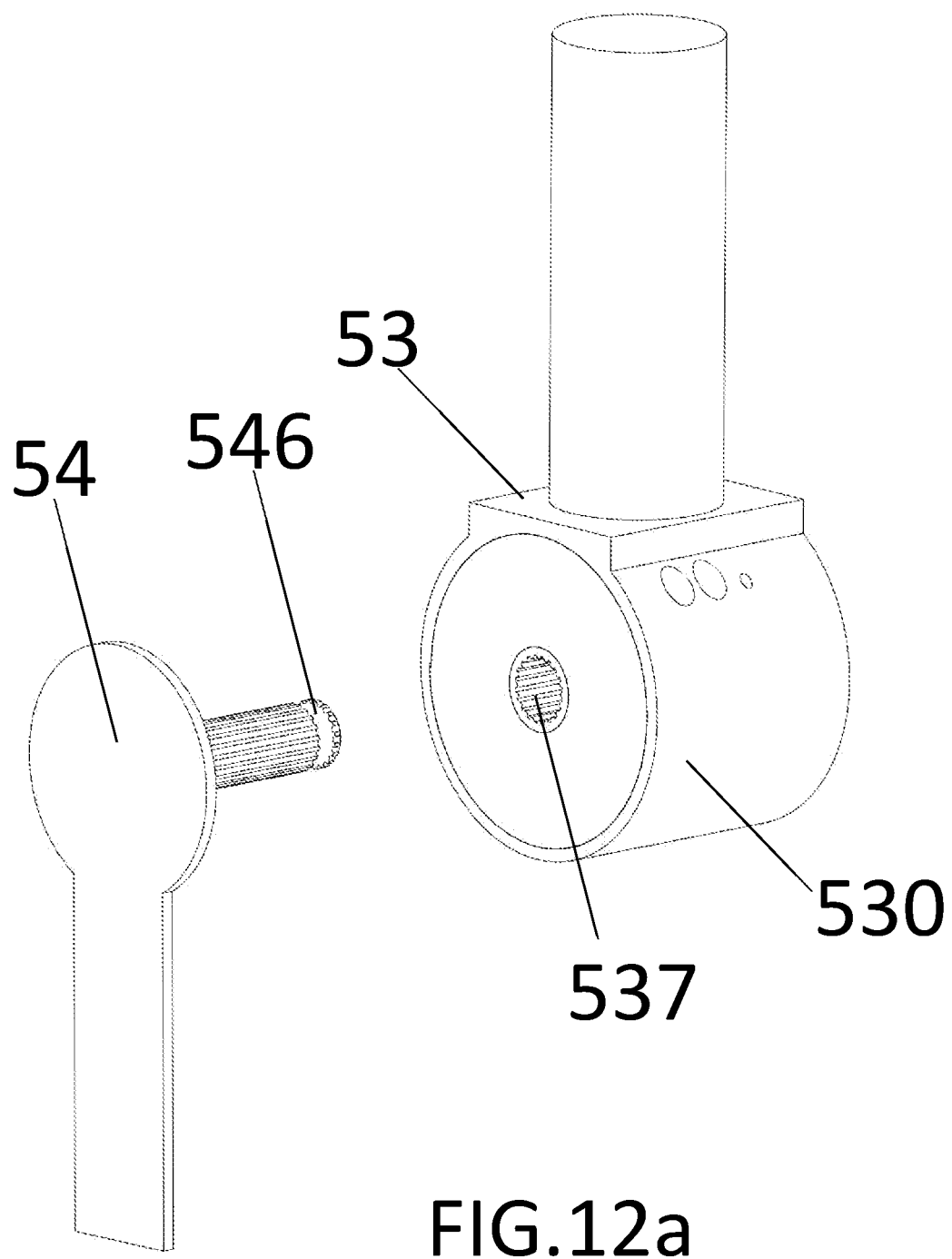
FIG. 12a is a structural schematic diagram of another embodiment of a quick-release joint of an exoskeleton in the present invention.
Figure 12B:
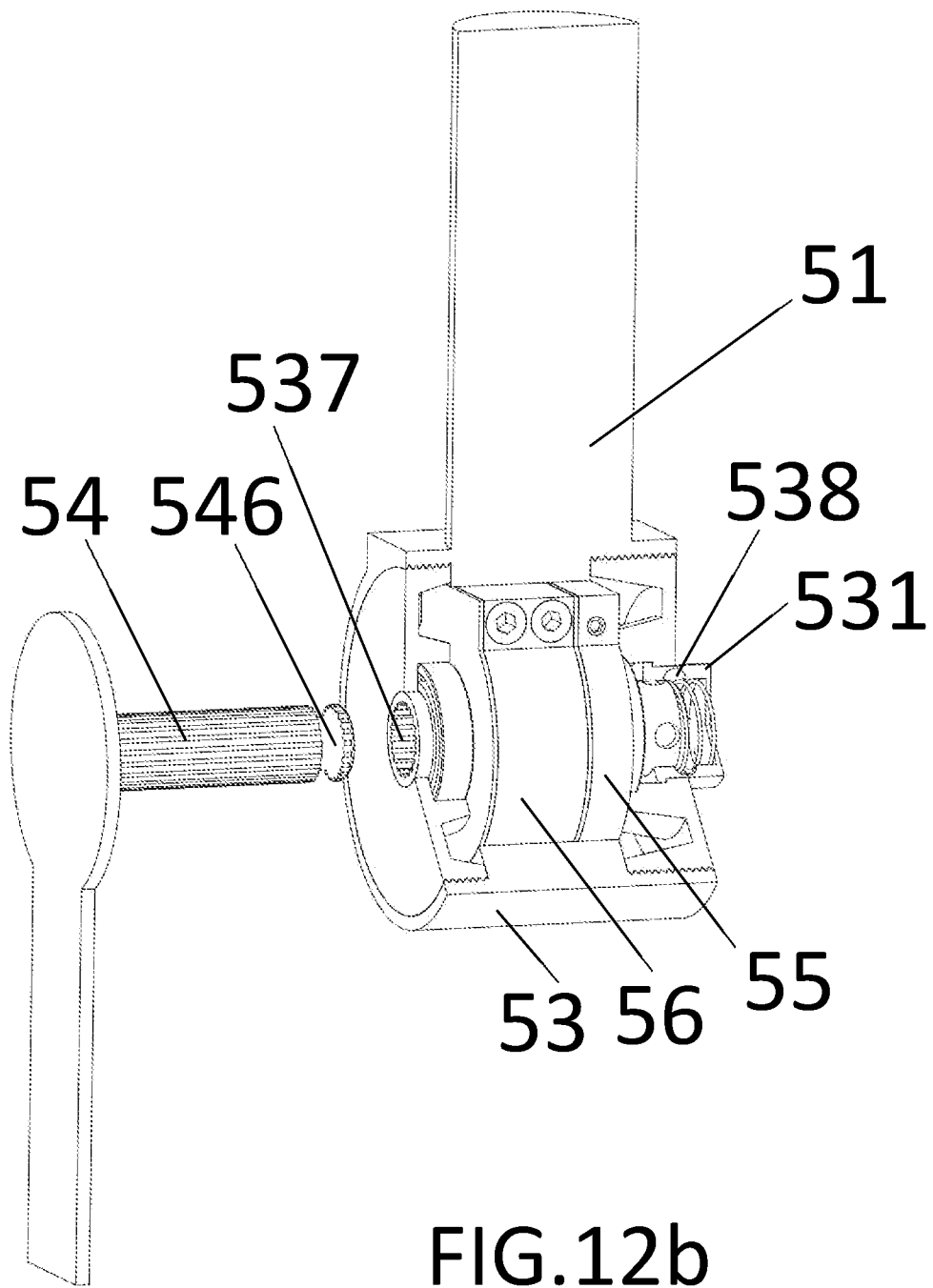
Figure 12C:
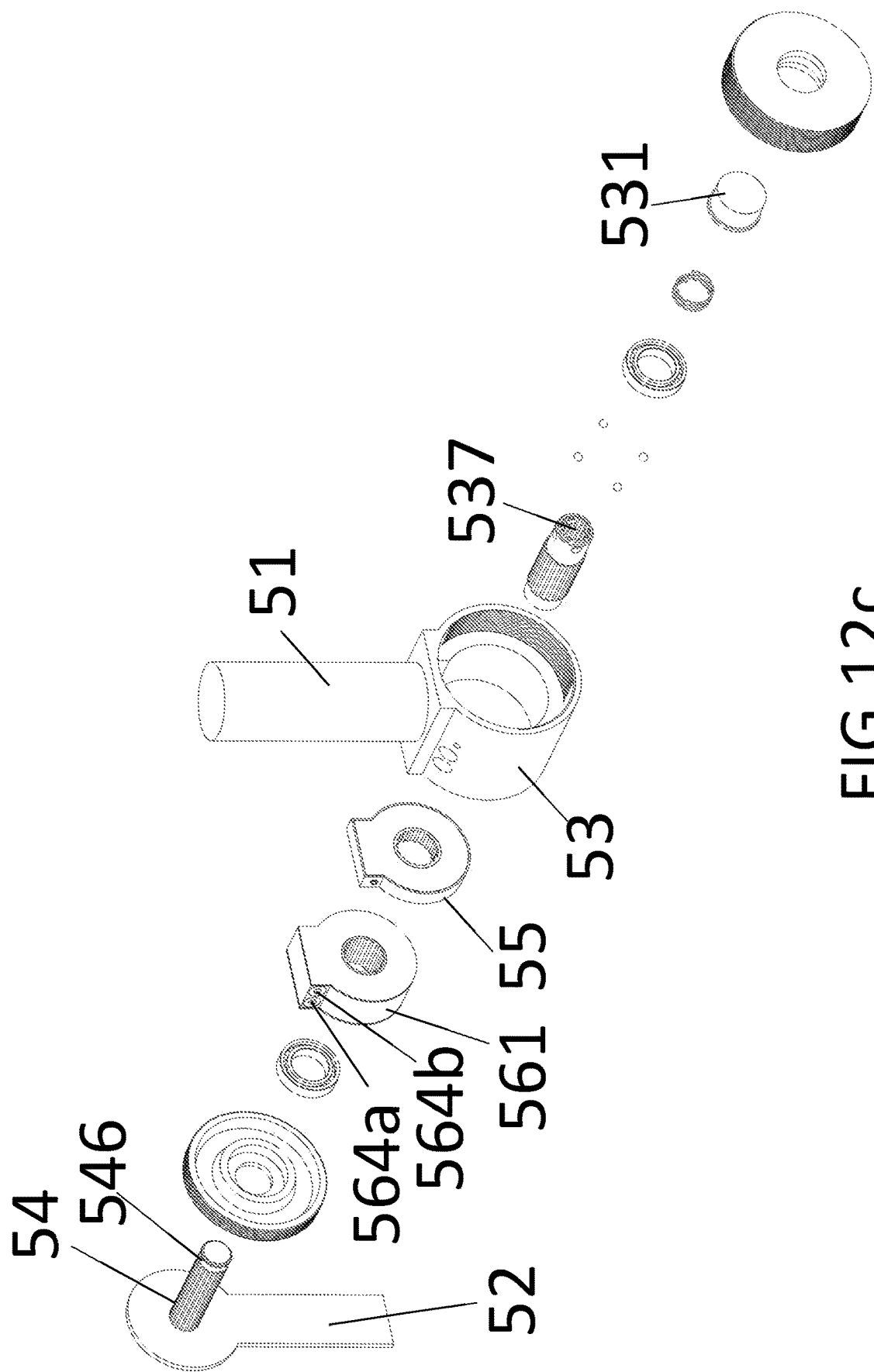

In another specific embodiment, with reference to FIG. 12a, FIG. 12b and FIG. 12c, the quick-detachable connector 54 is not a tenon but a spline quick-detachable end, and the end part is provided with a ball locking groove 546. Accordingly, a spline quick-detachable hole 537 and a quick-detachable button 531 are arranged in the housing/shell 530 of the quick-detachable end 53. A resetting spring is arranged in the quick-release button, and a ball groove 538 is arranged on the inner wall. When the spline quick-detachable end is inserted into the spline quick-detachable hole 537, the quick-detachable button 531 is pressed to compress the resetting spring, so that the ball groove 538 is exposed and the spline quick-detachable end ejects the ball into the ball groove 538. After the spline quick-detachablee end has been completely inserted into the spline quick-release hole 537, the quick-detachable button 531 is released to be ejected toward the outer side of the end cover under the action of the resetting spring. The ball groove 538 on the inner side of the quick-detachable button 531 slides out of the corresponding position of the ball, and the ball is forcedly ejected into the corresponding ball locking groove 546 on the spline quick-detachable end, thereby preventing the spline quick-detachable end from falling off. The technical advantage of using the spline quick-detachable end is that more angles can be set, but the cost of the spline is relatively high.

Further, the existing rotating joint adopts active drive or passive drive, damping and feedback force characteristics are hardly considered in the exoskeleton that adopts passive drive. For exoskeleton joints without damping and feedback force characteristics, the dynamic response characteristics are very sensitive. In actual use, the vibration and sloshing influences cannot be effectively reduced, and the locomotion position and bearing characteristics of the unit are prone to instability. In actual use, the exoskeleton without damping and resilience characteristics will enable the wearer to feel prone to large sloshing, and is prone to sudden flashing under load. Because the exoskeleton is supported by the dead point principle of the hinging of the connecting rod and the dead point principle is a critical stable state that is prone to instability, if the damping and resilience characteristics are not added, the device is prone to rapid destabilizing motion. Such motion in the user experience is that the device flashes rapidly from a stable position to another stable position. Such motion may make it difficult for the wearer to cope with, and even may bring an injury in serious cases.

In view of this, the quick-release joint in the present embodiment further comprises a damping unit 55 and/or a resilient unit 56.

In a specific embodiment, with reference to FIG. 10a, FIG. 10b, FIG. 10c, FIG. 11b, FIG. 11c and FIG. 11d, the damping unit 55 comprises a damping box inner cover 550 and a damping box outer cover 551 which are matched with each other. Quick-release button mounting holes 552 matched with the quick-release button 531 are arranged on the damping box outer cover 551 and the middle of the damping box inner cover 550. A damping fluid diversion groove 553 is arranged at one side of the damping box inner cover 550 that faces the quick-release button 531 along the circumferential direction of the quick-release button mounting holes 552. A damping fluid fluctuation block 554 is arranged at one side of the damping box outer cover 551 that backs to the quick-release button 531 in a direction corresponding to the damping fluid diversion groove 553. Damping fluid filling holes 555 are evenly arranged on the damping box outer cover 551/the damping box inner cover 550 along the circumferential direction of the quick-release button mounting holes 552.

Figure 13B:
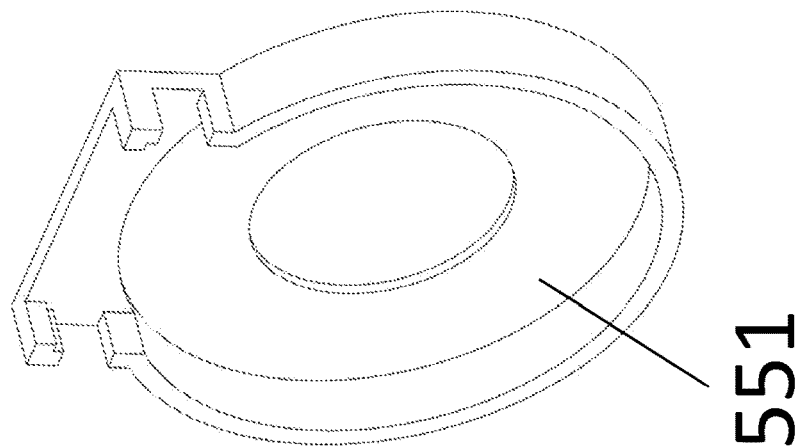
Figure 13B:
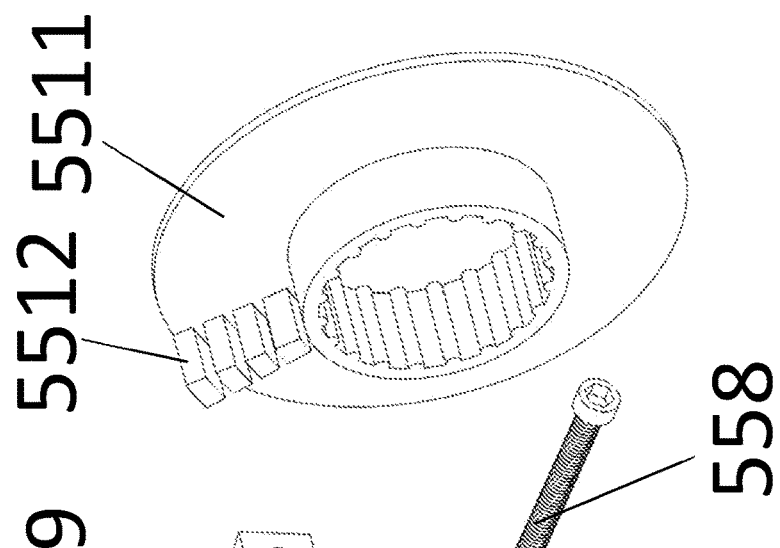
Figure 13B:
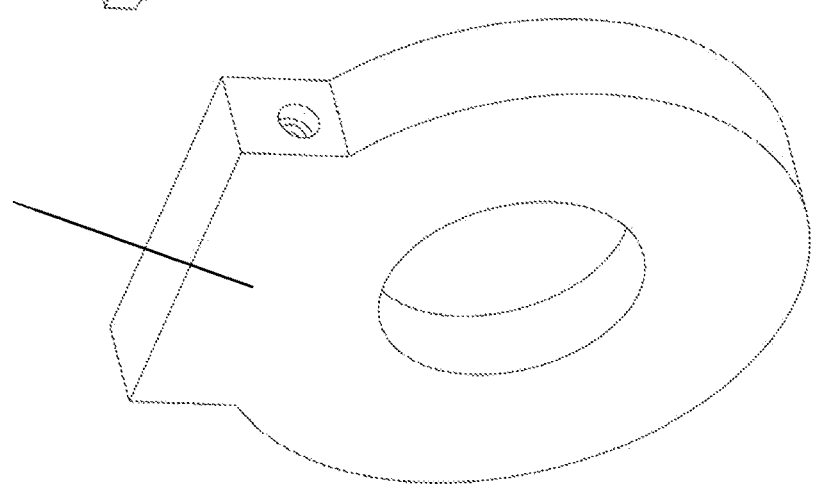
Figure 13C:
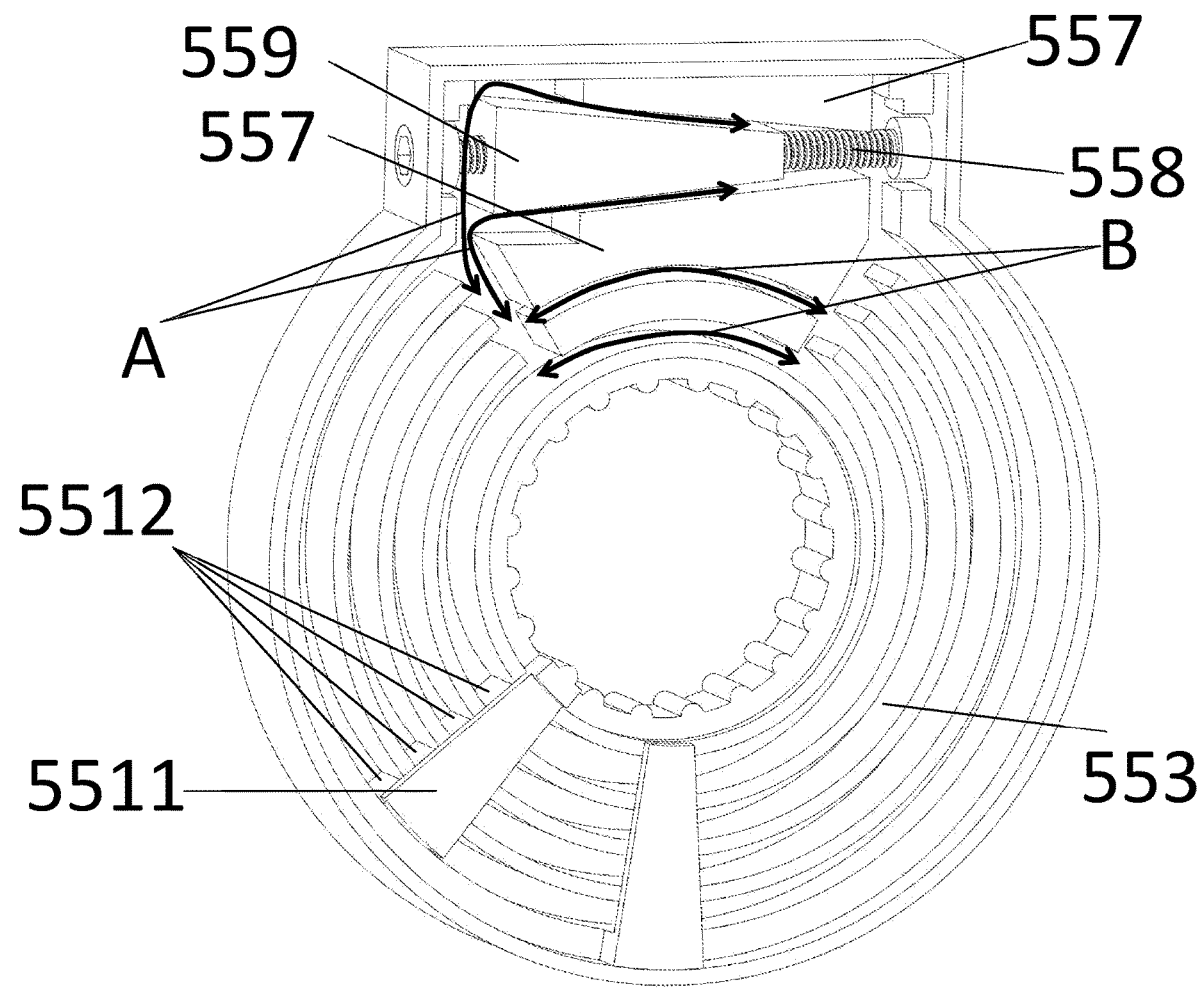
FIG. 13c is a schematic diagram that reflects a flow direction of damping fluid inside a damping unit in FIG. 13a or FIG. 13b.

In another specific embodiment, with reference to FIG. 13a, FIG. 13b and FIG. 13c, the damping unit is a damping unit with adjustable damping and also comprises a damping box inner cover 550 and a damping box outer cover 551 which are matched with each other. Quick-release button mounting holes 552 matched with the quick-release button are arranged on the damping box outer cover 551 and the middle of the damping box inner cover 550. A damping fluid diversion groove 553 is arranged in the damping box inner cover 550. The different is that, in the present embodiment, a damping fluid overflow groove 556 is arranged on the top of the damping fluid diversion groove 553. An upper and a lower fixed wedge ports 557 are arranged above the damping fluid overflow groove 556. A damping regulating knob 558 is arranged between the two fixed wedge ports 557. The damping regulating knob 558 is arranged on an adjustable wedge surface 559 of the damping regulating knob 558 in a manner of moving leftwards and rightwards relative to the regulating knob 558, so that a gap among the adjustable wedge surface 559 and the fixed wedge ports 557 forms a flow adjustable path A of the damping fluid, as shown in FIG. 13c. Thus, the distance that the adjustable wedge surface 559 moves left and right can be adjusted by rotating the regulating knob 558, so as to change the size of the adjustable flow path A. The damping fluid overflow groove 556 forms a fixed flow path B of damping fluid, as shown in FIG. 13c, i.e., the flow size of the circulating damping fluid is not adjustable. In addition, the damping unit 55 also comprises a damper dial 5510 arranged between the damping box inner cover 550 and the damping box outer cover 551. The damper dial 5510 comprises a dial plate 5511, and a damping fluid dialing block 5512 which is arranged on a winder 5511.

In some specific embodiments of the present invention, the used damping fluid is silicone oil (a linear polysiloxane product maintained in a liquid state at room temperature). In some specific embodiments of the present invention, when the joints of the exoskeleton are made, materials having damping characteristics (such as rubber, damping composite materials, damping paint, etc.) are used to enhance the damping characteristics of various joints of the exoskeleton.

Figure 11A:
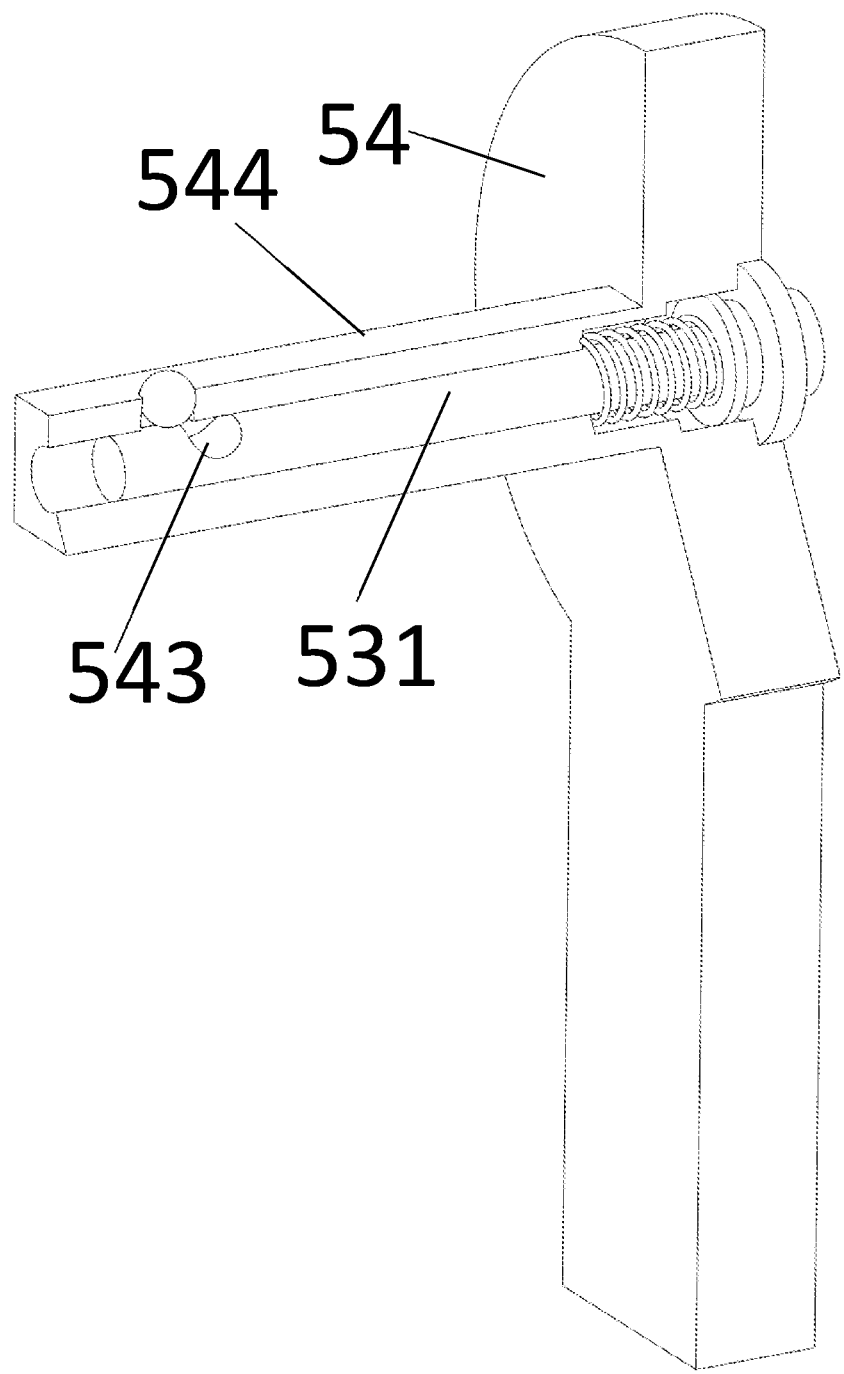
FIG. 11a is a structural schematic diagram of a tenon quick-release connector in another embodiment of a quick-release joint of an exoskeleton in the present invention.
Figure 11B:
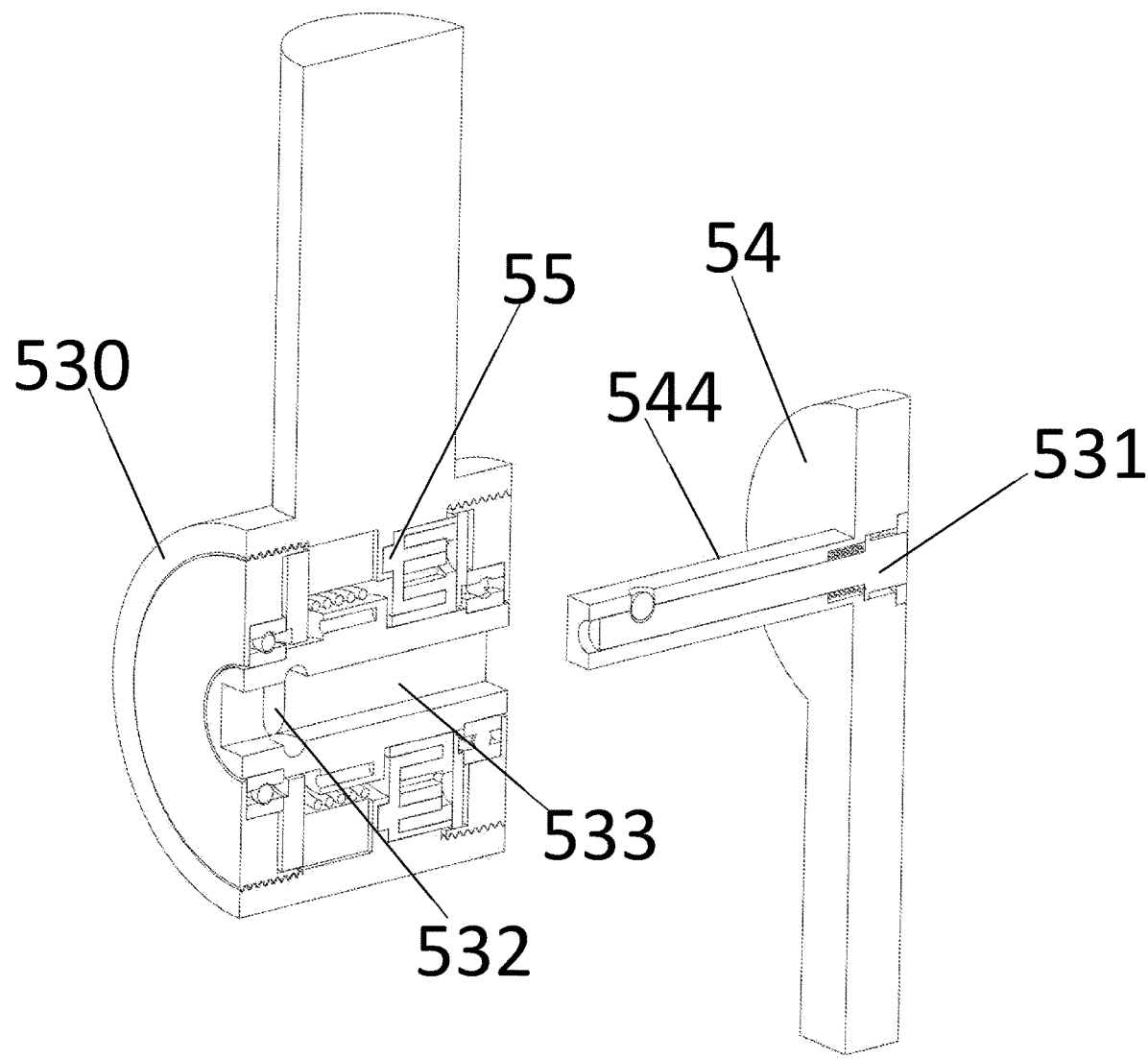
Figure 11D:
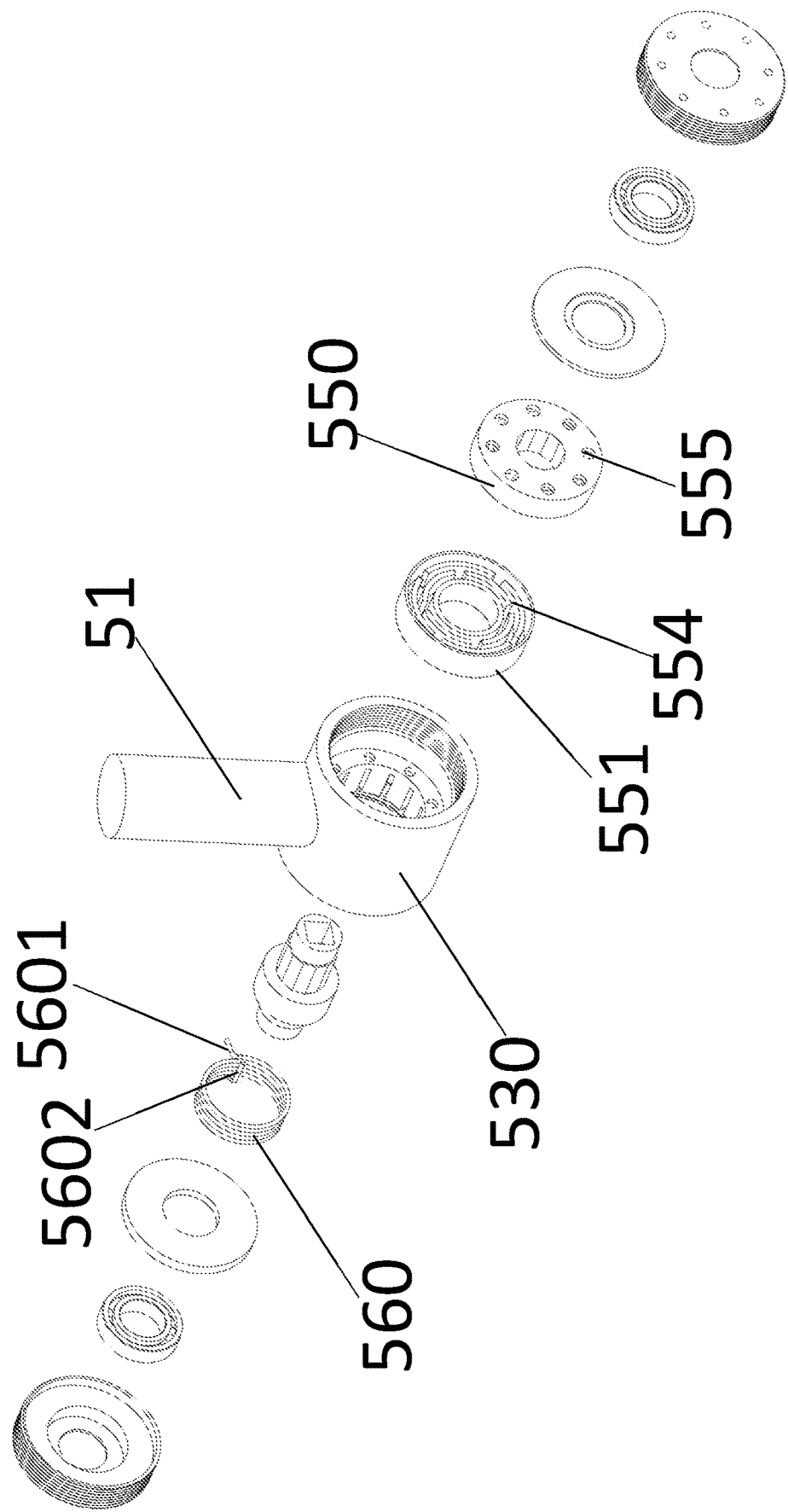

In a specific embodiment, with reference to FIG. 11c and FIG. 11d, the resilient unit 56 is a unidirectional resilient unit which comprises a torsion spring 560. A torsion spring outer ear groove 5301 for accommodating an outer ear 5601 of the torsion spring 560 is arranged in the housing 530 of the quick-release end, and a quick-release shaft sleeve 539 in the quick-release end is provided with a torsion spring inner ear hole 5302. An inner ear 5602 of the torsion spring 560 is located in the torsion spring inner ear hole 5302. The shaft sleeve is also provided with a quick-release hole matched with the quick-release connector such as a tenon.

Figure 14A:
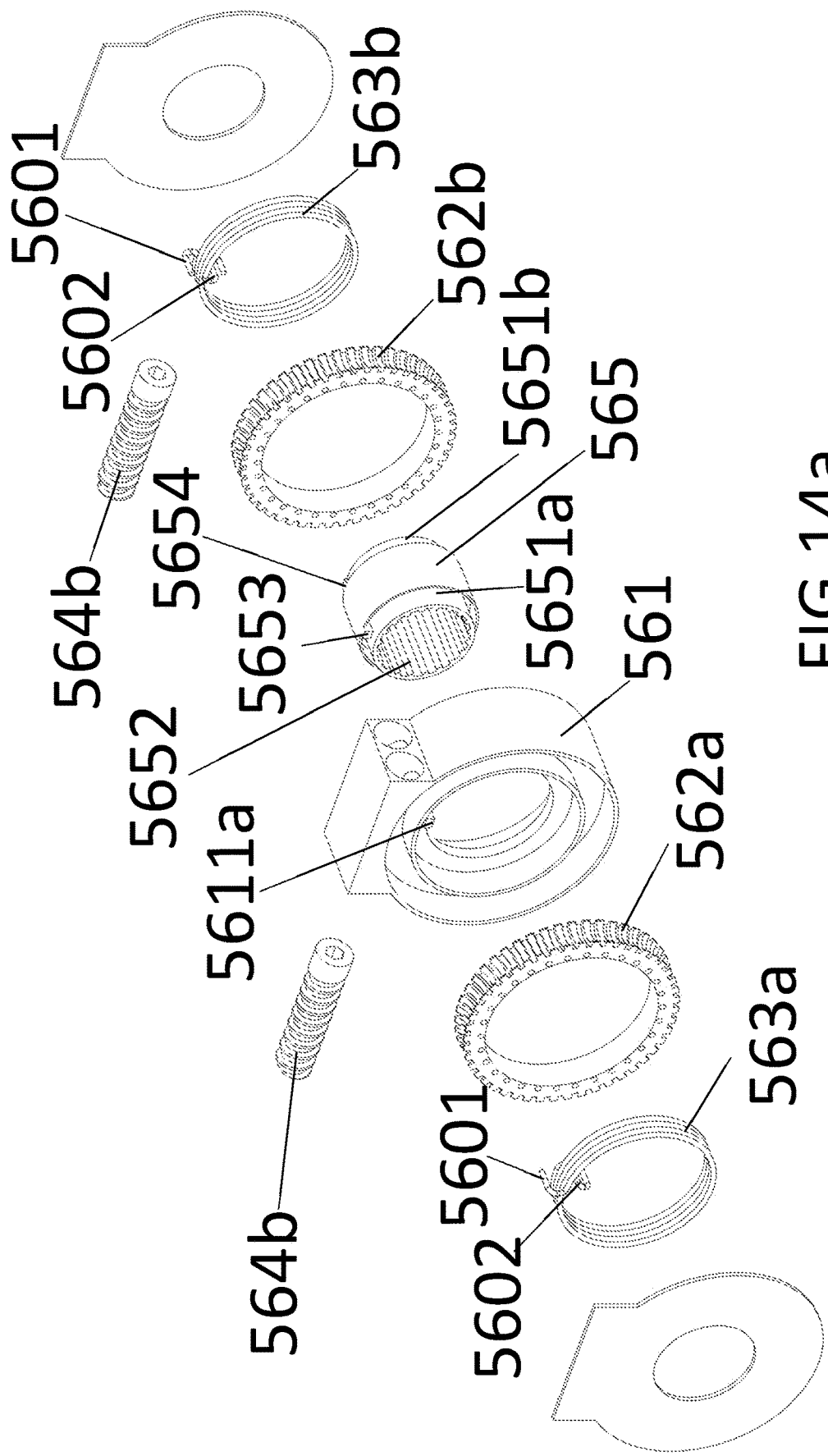
Figure 14C:
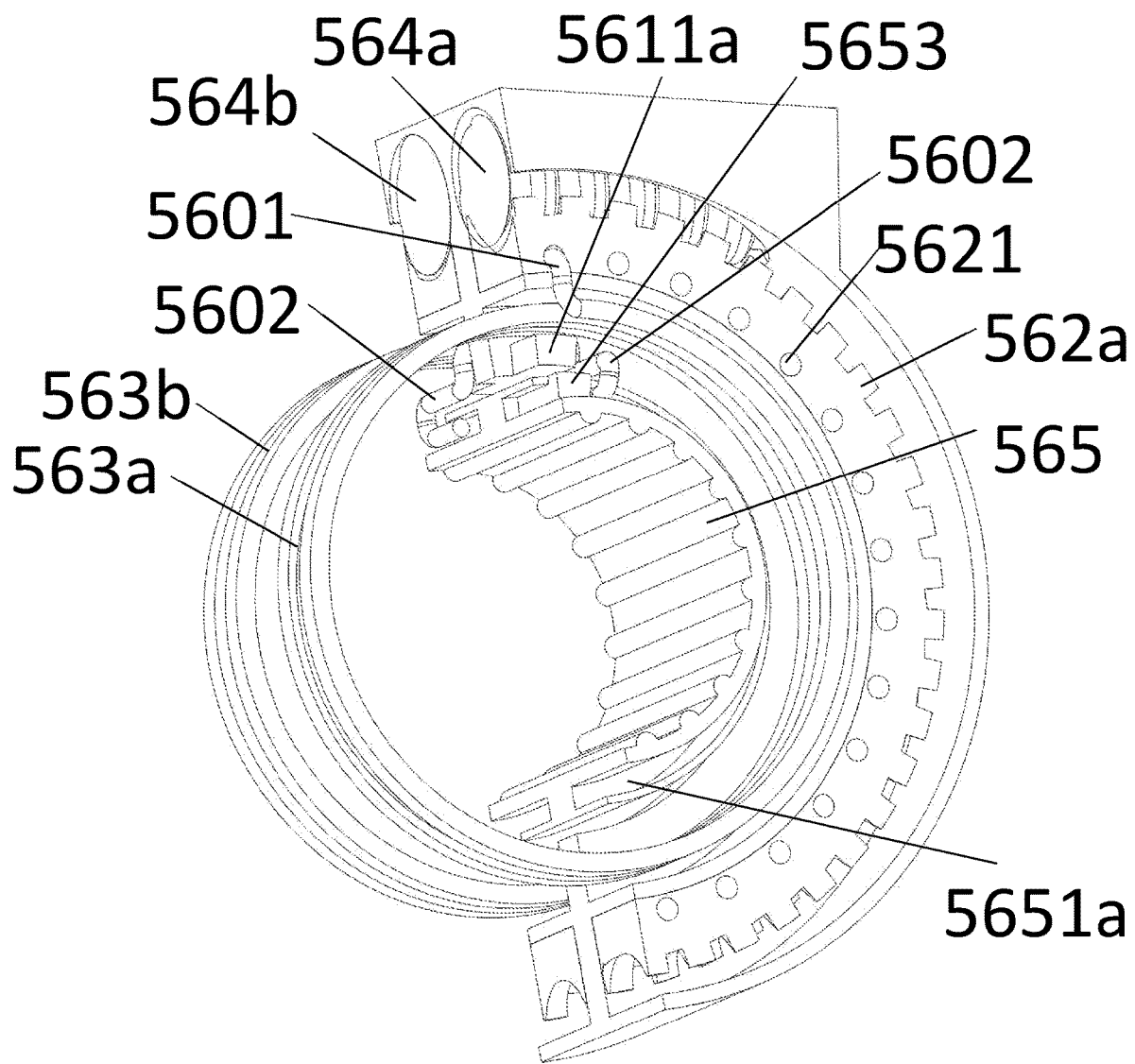
FIG. 14c is a schematic diagram that reflects cooperation of various components of a bidirectional resilient unit in FIG. 14a and FIG. 14b.

In a specific embodiment, with reference to FIG. 12b and FIG. 12c, the resilient unit 56 is a bidirectional resilient unit. Specifically, with reference to FIG. 14a, FIG. 14b and FIG. 14c, the bidirectional resilient unit comprises a bidirectional resilient mounting base 561 for mounting the resilient shaft sleeve 565. A clockwise resilient turbine 562a and an anticlockwise resilient turbine 562b are respectively mounted on the left side and the right side of the bidirectional resilient mounting base 561, and a clockwise resilient worm 564a and an anticlockwise resilient worm 564b which are matched with the clockwise resilient turbine 562a and the anticlockwise resilient turbine 562b are respectively mounted on the top. The bidirectional resilient unit also comprises a clockwise resilient torsion spring 563a and an anticlockwise resilient torsion spring 563b, wherein the clockwise resilient torsion spring 563a and the anticlockwise resilient torsion spring 563b are respectively installed in shaft holes of the clockwise resilient turbine 562a and the anticlockwise resilient turbine 562b, and outer ears 5601 of the clockwise resilient torsion spring 563a and the anticlockwise resilient torsion spring 563b are respectively inserted into outer ear holes 5621 on the clockwise resilient turbine 562a and the anticlockwise resilient turbine 562b (further, a plurality of outer ear holes 5621 used for regulating the pretightening force of the resilient torsion springs in advance as required are arranged on the clockwise resilient turbine 562a and the anticlockwise resilient turbine 562b along the circumferential direction). The inner ears 5602 of the clockwise resilient torsion spring 563a and the anticlockwise resilient torsion spring 563b are respectively located in inner ear chutes 5651a and 5651b on the left and right sides of the resilient shaft sleeve 565, and a clockwise resilient stopper block 5611a and an anticlockwise resilient stopper block 5611b are also respectively arranged in the resilient mounting base 561. A corresponding clockwise resilient shaft sleeve stopper block 5653 and an anticlockwise resilient shaft sleeve stopper block 5654 are respectively arranged in the inner ear chutes 5651a and 5651b on the left and right sides of the resilient shaft sleeve 565. When the quick-release connector (such as the spline quick-release connector) is installed in the resilient shaft sleeve 565 and the shaft sleeve 565 is driven to rotate clockwise, the clockwise resilient shaft sleeve stopper block 5653 on the resilient shaft sleeve 565 drives the inner ear 5602 of the clockwise resilient torsion spring 563a in the bidirectional resilient unit to rotate therewith, thereby generating reverse torque. The anticlockwise resilient torsion spring 563b is blocked by the anticlockwise resilient stopper block 5611b on the bidirectional resilient mounting base 561, and the reverse torque may not be transmitted to the quick-release connector shaft sleeve (such as a spline shaft sleeve) in the resilient shaft sleeve 565 through the resilient shaft sleeve 565. Similarly, when the quick-release connector (such as the spline quick-release connector) drives the quick-release connector shaft sleeve to rotate anticlockwise, the anticlockwise resilient stopper block 5611b pushes the anticlockwise resilient torsion spring 563b to rotate, thereby causing deformation of the anticlockwise resilient torsion spring 563b. On the contrary, the reverse torque generated to the shaft sleeve increases as the degree of rotation increases. At this moment, the inner ear 5602 of the clockwise resilient torsion spring 563a is blocked by the clockwise resilient stopper block 5611a. Therefore, the clockwise resilient worm 564a can rotate to enable the clockwise resilient turbine 562a to clockwise rotate, thereby increasing the initial stress of the resilient torsion spring. That is, in the present embodiment, the clockwise resilient turbine 562a, the anticlockwise resilient turbine 562b, the clockwise resilient worm 564a and the anticlockwise resilient worm 564b are arranged as initial stress regulating units of the bidirectional resilient unit so as to respectively regulate the initial stress of the clockwise resilient torsion spring and the anticlockwise resilient torsion spring, so that the bidirectional resilient unit has the effect of bidirectional different resilient characteristics.

Embodiment 6

Generally, the hip joint, the knee joint and the ankle joint of the exoskeleton are connected in series in structural design. Therefore, when the wearer wears the exoskeleton to bear the weight or exercise strongly, each part will bear a large impact force, thereby hurting the exoskeleton and even the skeleton of the wearer.

In view of this, to ensure that the exoskeleton is not completely compressed and keeps certain buffering capacity when the wearer bears the weight or exercises, and enhance impact resistance, the present invention also provides an exoskeleton which comprises a buffer device 43 which is matched with each corresponding joint of the exoskeleton to realize multi-degree of freedom motion of each joint and also absorb impact/vibration on each joint when the exoskeleton carries a load/moves. Specifically, the buffer device 43 may be an elastic deformation member or a porous elastic linear buffer that can be compressed or rebounded axially.

Figure 15:
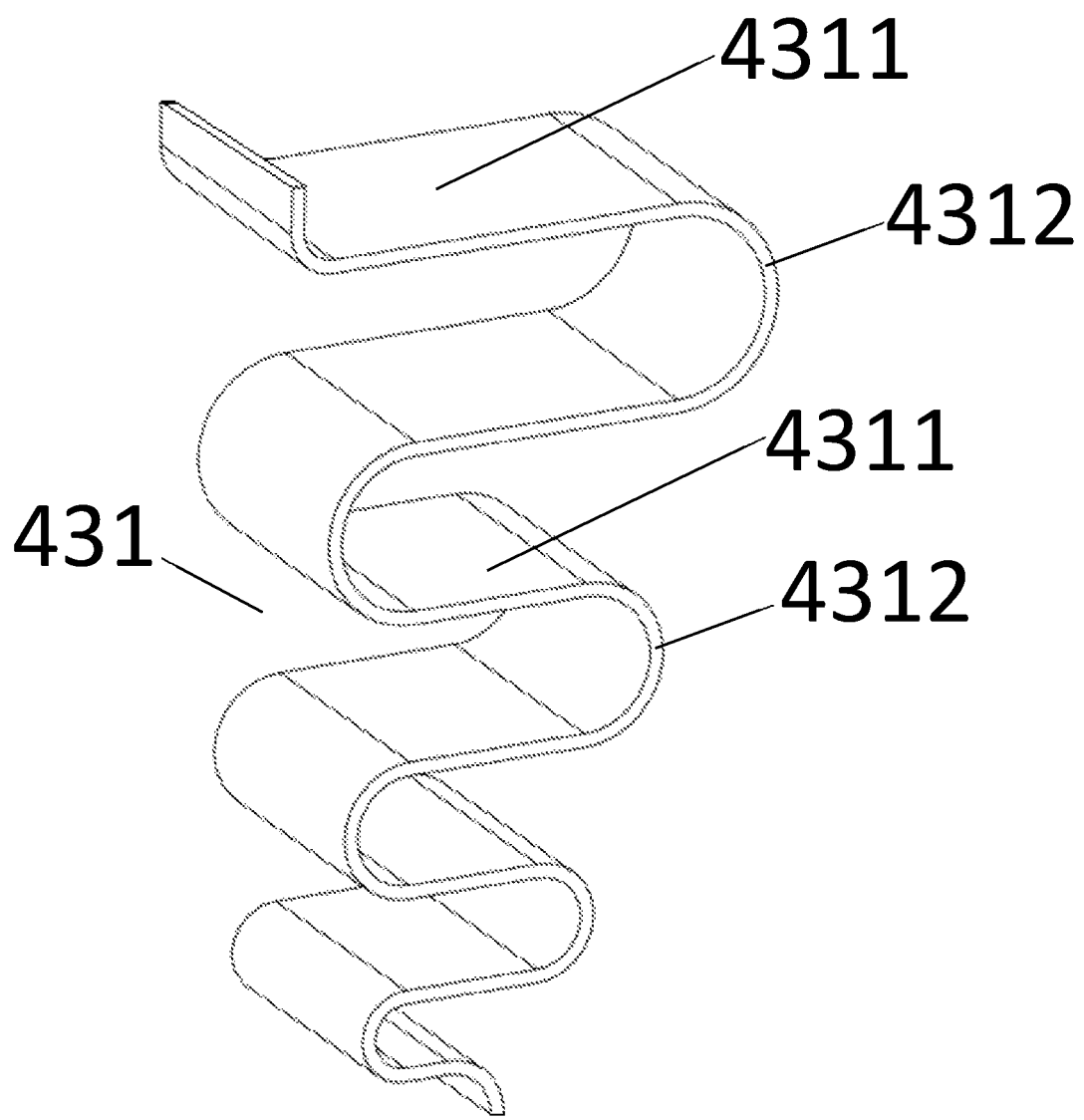
FIG. 15 is a structural schematic diagram of a first embodiment of a buffer device in an exoskeleton in the present invention.

In a specific embodiment, with reference to FIG. 15, the elastic deformation member is a serpentine spring 431. Specifically, the serpentine spring 431 is formed by connecting heads and tails of a plurality of horizontal leaf springs 4311 in sequence from top to bottom through bend end 4312, and the curvature of the bend end 4312 of each leaf spring 4311 is different. For example, the curvature of the bend end 4312 of each leaf spring 4311 is gradually reduced or gradually increased from top to bottom. In addition, the parameters, such as curvature, bending times and thickness, of the bend end of each leaf spring can be designed differently according to different actual conditions. In the present embodiment, the serpentine spring is arranged so that the rigidity of the leaf springs has nonlinear characteristics. As the load increases, equivalent rigidity also gradually increases, thereby ensuring that the buffer device is not completely compressed and keeps certain buffering capacity when the exoskeleton bears excessively large weight.

Figure 16A:
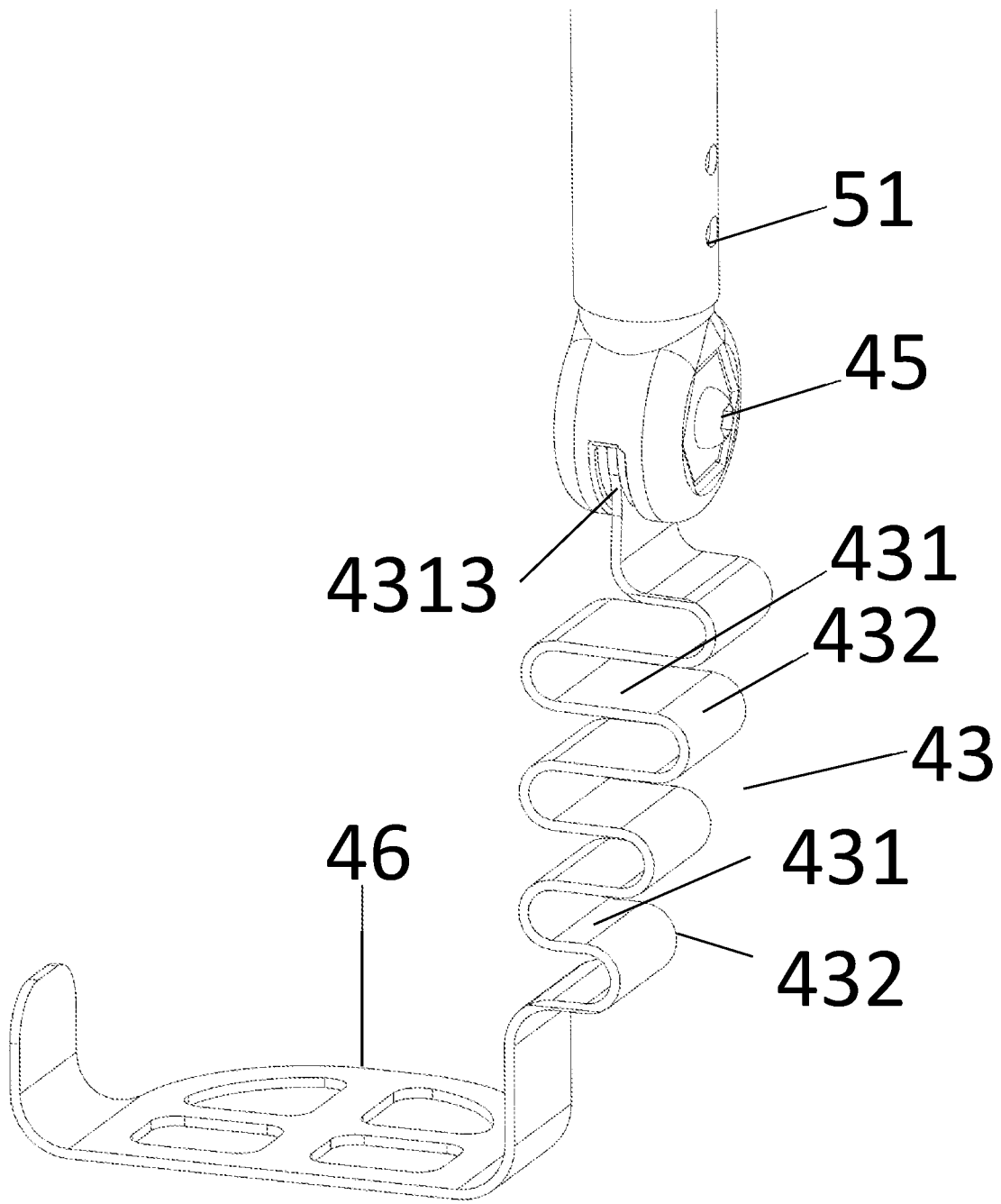
FIG. 16a and FIG. 16b are respectively structural schematic diagrams in which a buffer device in FIG. 15 is applied between an ankle joint and a sole supporting plate of an exoskeleton and between a hip joint and a thigh of an exoskeleton.
Figure 16B:
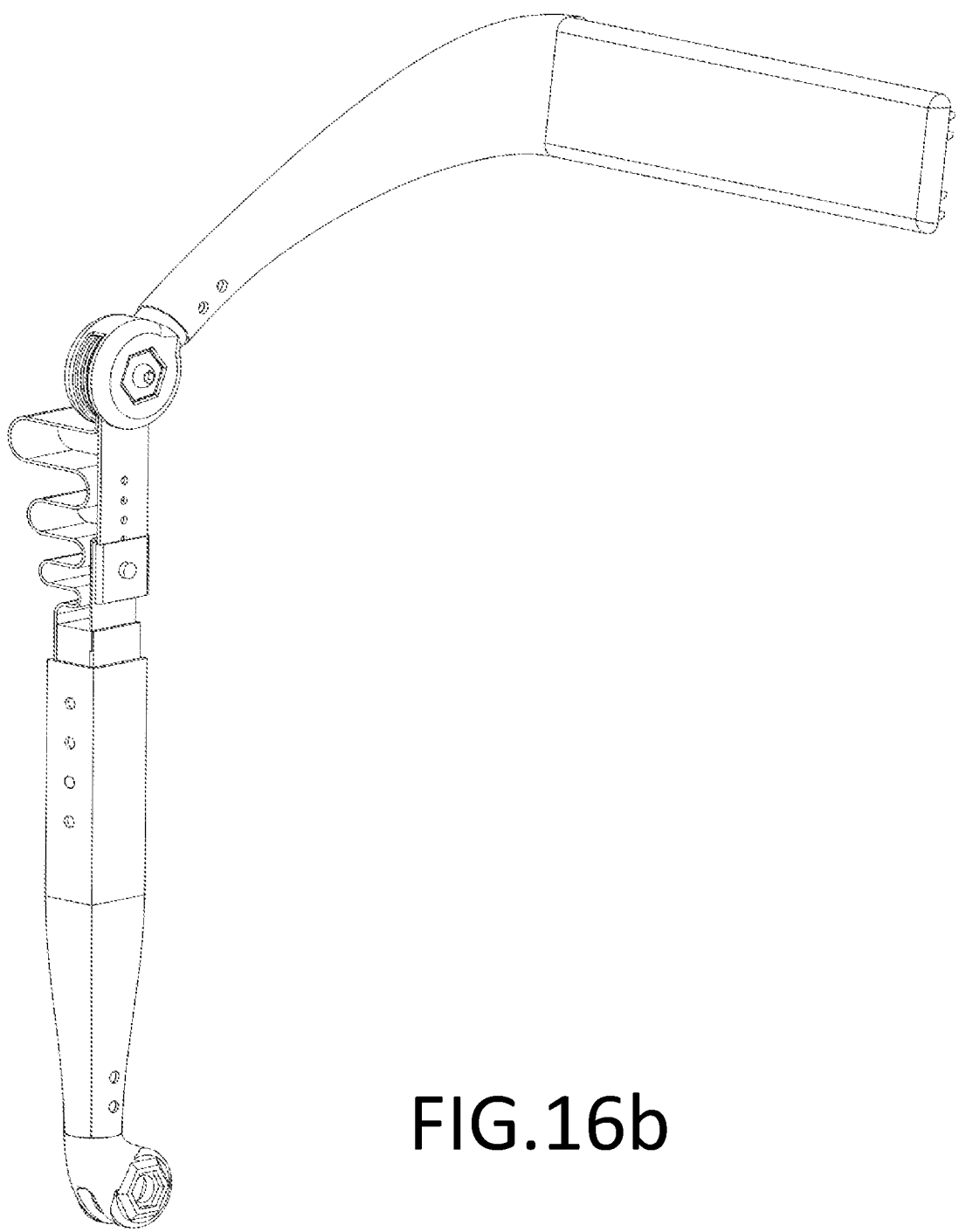

In practical application, with reference to FIG. 16a, the serpentine spring 431 can be arranged between the ankle joint 45 and a foot supporting plate 46 of the exoskeleton, and a joint connecting unit (such as a rotating key slot 4313) rotatably connected with the ankle joint 45 is arranged on the top of the serpentine spring 431 (further, a rotating damper can also be arranged between the rotating key slot and the ankle joint). The bottom is connected with the foot supporting plate 46 through a flexible transition curved surface, with central axes thereof being perpendicular to each other. Since the serpentine spring is arranged between the ankle joint and the foot supporting plate, not only the buffering effect is achieved, but also the ankle joint of the exoskeleton follows varus and valgus motion of the ankle of the human body. Moreover, during varus and valgus motion, as the deformation increases, the serpentine spring 431 provides a proper feedback force for the ankle of the human body, so as to provide an additional supporting force for the wearer when walking on uneven roads, thereby preventing motion injuries such as cripple caused to the exoskeleton and the human body system due to the uneven roads during motion.

It can be seen that when the serpentine spring 431 is applied between the ankle joint and the foot supporting plate, the serpentine spring 431 not only has the buffer function, but also considers three-degree-of-freedom motion of the ankle joint (such as varus and valgus motion following the ankle of the human body). Moreover, the serpentine spring 431 has damping characteristics in buckling/extension motion, and has restoring force during abduction/adduction motion and internal rotation/external rotation motion, to avoid motion loss of the ankle.

Figure 18A:
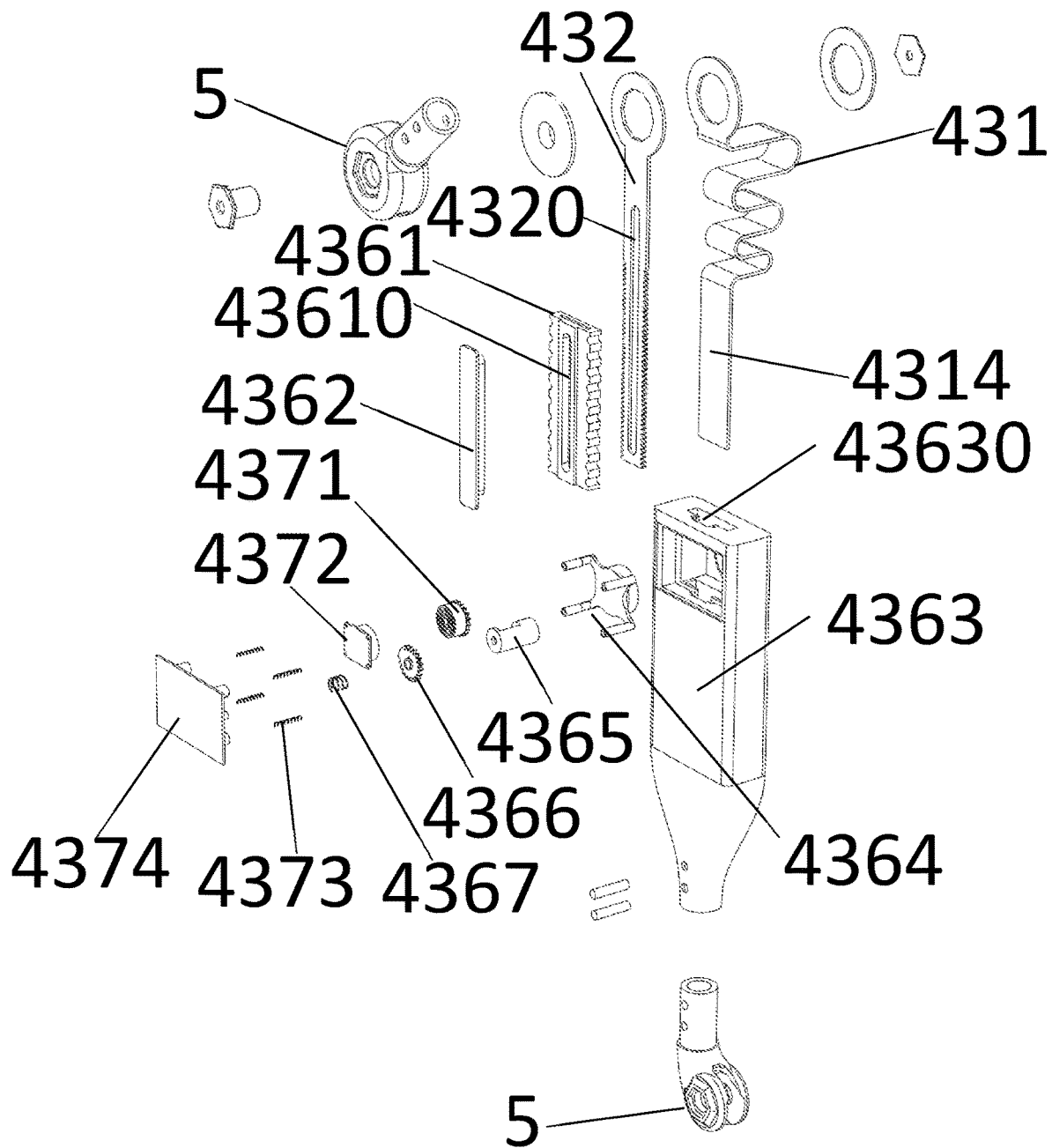
FIG. 18a is an exploded drawing of a third embodiment of a buffer device in an exoskeleton in the present invention.
Figure 18B:
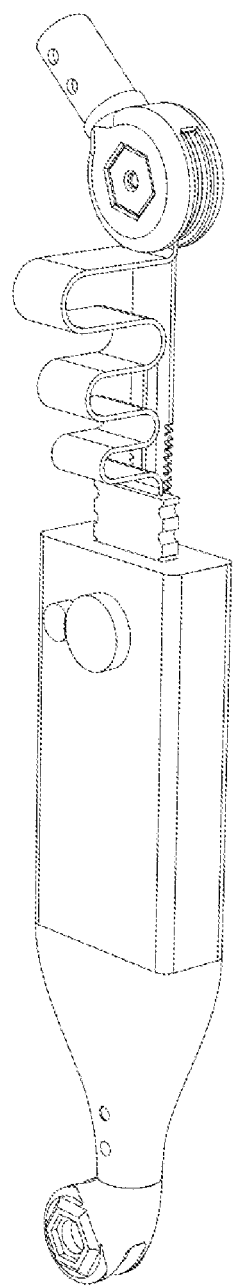
FIG. 18b is a structural schematic diagram in which a buffer device in FIG. 18a is applied between a knee joint and a shank.

In addition, the serpentine spring in the present embodiment can also be arranged on other parts of the exoskeleton, for example, between the knee joint and the shank as shown in FIG. 18b, or between the hip joint and the thigh as shown in FIG. 16c. The specific arrangement position and the connection relationship among various parts can be regulated by those skilled in the art according to actual conditions.

In addition, the elastic deformation member in the present embodiment may not employ the serpentine spring, and may employ a compression spring unit, an air spring unit, three-dimensional elastic hollow material, rubber material, and a passive magnetic suspension unit realized by the repulsive effect of the same pole magnet. It should be understood that corresponding replacement is made by those skilled in the art according to corresponding needs.

Although the elastic deformation member is provided to buffer the impact and vibration of the exoskeleton during weight bearing or motion, since there is no damping characteristic and the deformation stroke of the elastic deformation member is not limited, the buffer device may be strongly vibrated near the natural frequency. The impact load energy can be completely eliminated through several oscillation periods after reception of the impact load and various friction effects of the contact between the exoskeleton and the human body, thereby causing damage to the human body.

In view of this, further, the buffer device 43 in the present embodiment is also provided with a damping unit used for dissipating vibrational energy in the motion when the exoskeleton bears the weight/moves, for example, dissipating displacement or speed difference between the buffer device and the exoskeleton.

Figure 17A:
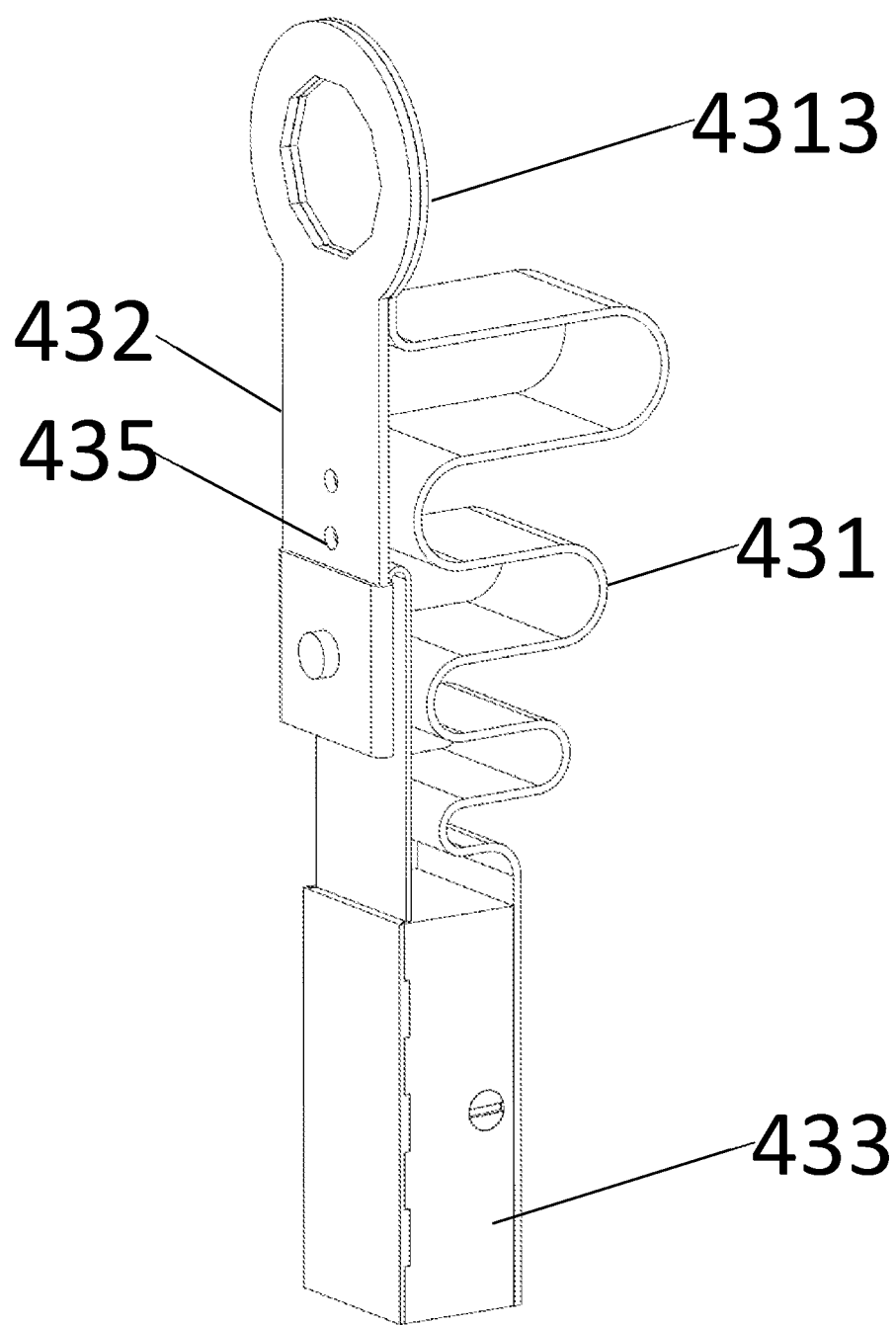
FIG. 17a is a structural schematic diagram of a second embodiment of a buffer device in an exoskeleton in the present invention.
Figure 17B:
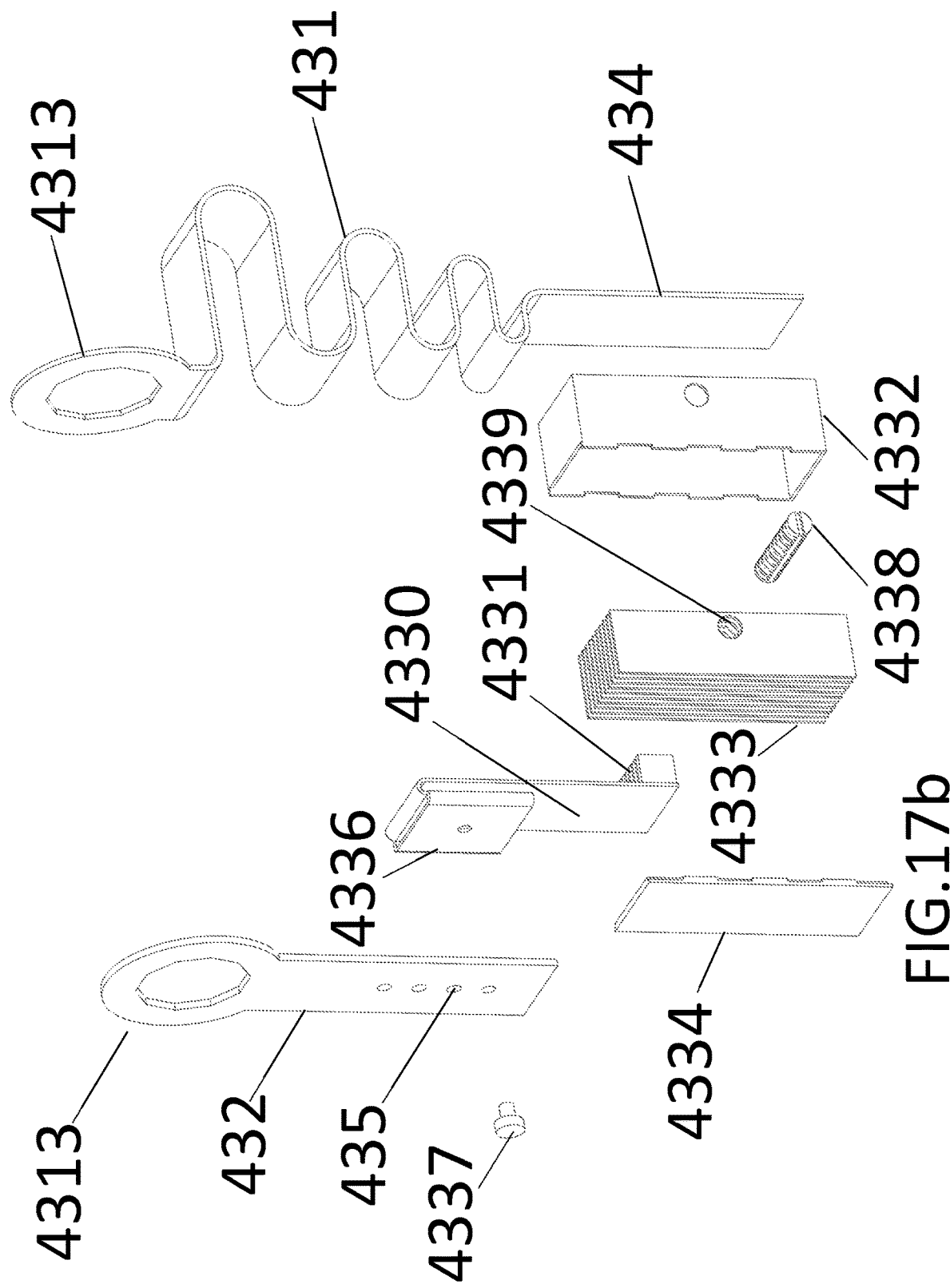

In a specific embodiment, with reference to FIG. 17a and FIG. 17b, the damping unit is a linear damping unit. Specifically, the linear damping unit comprises a vertical leaf spring 432, a linear damping box 433, and a damping box mounting block 434. The linear damping box 433 comprises a sheet-shaped push rod 4330, a damping fluid paddle 4331, a damping box body 4332 internally provided with a multilayer damping fluid diversion groove 4333, and a damping box body end cover 4334. The vertical leaf spring 432 is overlapped on one side of the above serpentine spring 431, and the bottom of the vertical leaf spring 432 is fixed to the top of the sheet-shaped push rod 4330. The bottom of the sheet-shaped push rod 4330 is fixedly connected with the damping fluid paddle 4331, and the damping fluid paddle 4331 and the vertical leaf spring 432 are respectively located on two opposite sides of the sheet-shaped push rod 4330. The damping fluid paddle 4331 is matched with the multilayer damping fluid diversion groove 4333 in the damping box body 4332 (i.e., the damping fluid paddle 4331 can slide up and down along the multilayer damping fluid diversion groove 4333 in the vertical direction), and is sealed by the damping box body end cover 4334. The damping box body 4332 of the linear damping box 433 is fixed to the bottom of the serpentine spring 431 (i.e., an end away from the joint) through the damping box mounting block 434, so that the bottom of the vertical leaf spring 432 can only slide along the vertical direction. Due to the action of the damping fluid, there are certain damping characteristics in the buffer process. Thus, during the motion, a larger restoring force can be provided for the wearer, thereby avoiding the situation of forward and backward shaking instability when the human body walks.

In practical application, the linear damping unit is arranged between the ankle joint and the foot supporting plate like the serpentine spring 431. Specifically, like the serpentine spring 431, the top of the vertical leaf spring 432 of the linear damping unit is rotatably connected with the ankle joint through a joint connecting unit such as a rotating key slot. The vertical leaf spring 432 is on a side close to the human body, and the bottom of the damping box mounting block 434 of the linear damping unit is connected with the foot supporting plate. Since the linear damping unit is arranged on one side of the serpentine spring 431, and the bottom of the vertical leaf spring can only slide along the vertical direction, the bending and stretching motion of the ankle joint in the sagittal plane can be satisfied. At the same time, when the ankle joint needs to conduct abduction/adduction motion, it can be realized by bending the vertical leaf spring 432 and the serpentine spring 431. When the ankle joint needs to conduct internal rotation/external rotation motion, it can be realized by twisting the vertical leaf spring and the serpentine spring. Moreover, during abduction/adduction motion or internal rotation/external rotation motion of the ankle joint, the linear damping unit and the snakelike spring can provide certain joint restoring force, thereby avoiding the instability of the exoskeleton during motion and then avoiding joint injury because the human body bears the abnormal acting force of the exoskeleton. At the same time, when the human body wears the exoskeleton to walking with load, the impact load caused by the foot supporting plate that touches the ground, and the system vibration caused by the fluctuation of the load potential energy during walking, can also be relieved and suppressed under the action of the linear damping unit and the serpentine spring. In this process, the bending stiffness of a plurality of horizontal leaf springs 4311 of the serpentine spring 431 is much lower than the stiffness of the vertical leaf spring 432 subjected to compression along the surface direction. Therefore, the serpentine spring 431 will rapidly compress or relax to respond to impact and vibration, and the vertical leaf spring 432 with higher vertical stiffness will transmit the motion trajectory of the ankle joint end to the lower end of the linear damping box. The displacement difference between both ends drives the damping fluid paddle inside the linear damping box to slide up and down, and pushes the damping fluid such as silicone oil to flow back and forth in the diversion groove in the linear damping, thereby dissipating the impact load or the energy inputted by the forced vibration to avoid apparent resonance of the buffer device.

In the present embodiment, the vertical leaf spring 4. 32 is arranged and forms, together with the linear damping box, a stroke limiting unit for limiting the compression stroke of the elastic deformation member. This is because the compression stroke of the elastic deformation member is large. If the compression stroke is not limited, when the exoskeleton is under the load, if the single leg alternately hangs and touches the ground (load and no-load cycles occur), the resilient stroke of the elastic deformation member is too large, thereby resulting in apparent change in the size of the exoskeleton and possibly causing damage to the human body.

In addition, in the present embodiment, the compression stroke limitation mode/the realizing form of the stroke limiting unit of the elastic deformation member is not limited to this, and can also be realized by adopting a slider block chute unit separately, or the linear motion is converted into rotation motion to realize through a rotation angle limiting unit.

In another specific embodiment, with reference to FIG. 18a and FIG. 18b, the damping unit that converts linear motion into rotation motion and limits the compression stroke of the elastic deformation member through the rotation angle also comprises a joint connecting unit (such as a rotating key slot 4313), a serpentine spring 431, a vertical leaf spring 432, a stroke limiting unit and a damping dissipation unit. The difference is that, the stroke limiting unit in the present embodiment comprises: a size regulating block 4361, a rack rail block 4362, a connecting rod 4363, a size regulating tenon 4364, a pretightening force regulating button 4365, a pretightening force regulating incomplete gear 4366 and a pretightening force regulating resetting spring 4367. The damping dissipation unit comprises a rotating damping gear 4371, a rotating damping base 4372, a size regulating spring 4373, and a connecting rod mounting cover 4374. The joint connecting units on the tops of the serpentine spring 431 and the vertical leaf spring 432 have polygonal docking holes with the same shape used for rotatable connection with joint rotating shafts (further, a rotation damping can also be arranged). The joint connecting units are overlapped perpendicularly so that the device is more compact, and can also be separated. The size connecting end 4314 on the bottom of the serpentine spring 431 is inserted into the corresponding wedge groove of the size regulating block 4361. The rack rail block 4362 penetrates through the slide rail 4320 on the vertical leaf spring 432 and is inserted into a rack rail fixing groove 43610 on the size regulating block 4361. The size connecting end 4314, the size regulating block 4361 and the rack rail block 4362 on the lower end of the serpentine spring 431 are fixedly connected by screws, screw holes or bonding. The vertical leaf spring 432 is clamped between the rack rail block 4362 and the size regulating block 4361, and can only slide vertically with respect to the size regulating block 4361. However, a part, which does not enter the rack rail block 4362, above the vertical leaf spring 432 can be bent and deformed under the action of an external force, and a corresponding restoring force is generated, thereby conforming to the abduction/adduction motion and the external rotation/internal rotation motion of the joint. Although the size rail connecting end 4314 at the bottom of the corresponding serpentine spring 431 cannot be bent or compressed and deformed due to fixed connection to the size regulating block 4361, an upper folded and bent region can produce obvious compression deformation or bent deformation, thereby simultaneously satisfying the joint motion and impact buffering motion. The top end of the connecting rod 4363 is provided with a wedge groove 43630 which has a section profile corresponding to a section profile of a combined leaf spring unit formed by a combination of the serpentine spring 431, the vertical leaf spring 432, and the rack rail block 4362 of the size regulating block 4361, so that the combined leaf spring unit can be smoothly inserted into the mounting groove and fixed in an appropriate position to adapt to body size differences of different wearers. Specifically, a spring tenon unit is adopted to fix the relative positions of the combined leaf spring unit and the connecting rod 4363, wherein clamping groove structures are evenly arranged at equal distances on both sides of the size regulating block 4361. In the present embodiment, the profiles of clamping grooves are semi-cylindrical. Apparently, clamping grooves having rectangular, trapezoidal and triangular section profiles can also be employed. The tenon unit with elastic restoring force is arranged in a tenon mounting groove provided on the connecting rod 4363. Specifically, the size regulating tenon 4364 in the present embodiment is provided with two cylindrical bayonet devices on both sides of the size regulating block 4361, thereby ensuring that the size regulating tenon 4364 unit can reliably bear the weight of the exoskeleton and the load transmitted from the upper part of the exoskeleton. At the same time, with the help that a slotted section profile is the same as the profile of the combined leaf spring unit, shaking in all directions when the buffer unit is fixed into a leg connecting rod is avoided.

However, the motion range of the stroke limiting unit is generally smaller than the maximum compression stroke of the elastic deformation body. Therefore, regardless of the extent to which the stroke limiting unit specifically limits the deformation of the elastic deformation body, the elastic deformation body can only adapt to a specific load range (excessively light load causes that the elastic deformation body hardly responds, and excessively heavy load causes that the elastic deformation body is always compressed to the lowest position of the stroke limiting unit, and in both cases, further buffering is impossible).

Therefore, further, to enable the buffer device to deform the elastic deformation member within the optimal stroke range under different weight-bearing conditions, a pretightening force regulating unit is added on the buffer device in the present embodiment.

In a specific embodiment, with reference to FIG. 17a and FIG. 17b, the pretightening force regulating unit is specifically provided with a plurality of pretightening force regulating holes 435 in sequence from top to bottom on the vertical leaf spring 432. Accordingly, a pretightening force regulating chute 4336 is arranged in the position of the top of a sheet-shaped push rod 4330 connected to the vertical leaf spring 432, and the pretightening force regulating chute 4336 is matched with a pretightening force regulating hole 435 through a pretightening force regulating bolt 4337.

When the exoskeleton load is obviously changed, the serpentine spring 431 of the buffer device is obviously compressed (when load is increased) or elongated (when the load is reduced) under static state relative to a state under an original load; and when the original load exceeds a certain degree and the load is removed or reduced, the elongation length of the serpentine spring will exceed the linear damping stroke range. Therefore, when a new load is statically pressed on the exoskeleton, the above pretightening force regulating bolt 4337 is removed, and the pretightening force regulating chute 4336 is fixed to an appropriate pretightening force regulating hole 435 so that the damping fluid paddle 4331 in a static state is always at the upper part of the sliding stroke of the entire linear damping box 433 (that is, large-stroke slip can be performed in the buffer compression direction), thereby regulating the pretightening force of the linear damping unit.

In fact, because the serpentine spring 431 with variable stiffness is used, the serpentine spring 431 can have an objective deformation range under different loads. However, the maximum compression stroke of the serpentine spring 431 may be greater than the working stroke of the linear damping unit (the sliding range of the linear damping box 433). Therefore, if the compression stroke of the serpentine spring 431 is not limited, when the load is removed, the length of the serpentine spring 431 may be greatly rebounded, thereby causing obvious change in the size of the exoskeleton and thus injuring the skeleton or muscle of the wearer. In view of this, to enable the exoskeleton to work normally under different loads, a stroke limiting unit is needed to control the compression and resilience range of the serpentine spring 431. Specifically, in the present embodiment, the pretightening force of the serpentine spring 431 is adjusted by the stroke limiting unit which is composed of the pretightening force regulating hole 435, the pretightening force regulating chute 4336 and the pretightening force regulating bolt 4337, thereby controlling the compression and resilience range of the serpentine spring 431. That is, the compression stroke of the serpentine spring 431, i.e., the pretightening force, is regulated by regulating the position of the damping fluid paddle 4331 in the linear damping box 433 with respect to the vertical leaf spring 432.

In a specific embodiment, the multilayer damping fluid diversion groove 4333 of the linear damping box 433 is divided into upper and lower layers of reflow structures. That is, the upper layer provides a complete sliding space for the damping fluid paddle, and the lower layer is a damping fluid reflow layer. A regulating valve mounting hole 4339 for mounting a rotation damping regulating valve 4338 is arranged in the middle of the reflow layer of the damping box body 4332. The rotation damping regulating valve 4338 is put into the multilayer damping fluid diversion groove 4333 through a damping housing mounting hole 43310 on the side surface of the damping box body 4332, and the rotation damping regulating valve 4338 inside the damping fluid diversion groove 4333 can be rotated by a tool such as a screwdriver. When the rotation damping regulating valve 4338 is rotated to be parallel to the flow direction of the multilayer damping fluid diversion groove 4333, the damping fluid can pass through the damping fluid reflow layer with a large cross-sectional area. When the damping regulating valve 4338 is rotated to be perpendicular to the flow direction of the multilayer damping fluid diversion groove 4333, the cross-sectional area of the damping fluid reflow layer is minimal. At this moment, the damping effect of the damping unit of the buffer device is obviously strongest.

Figure 19:
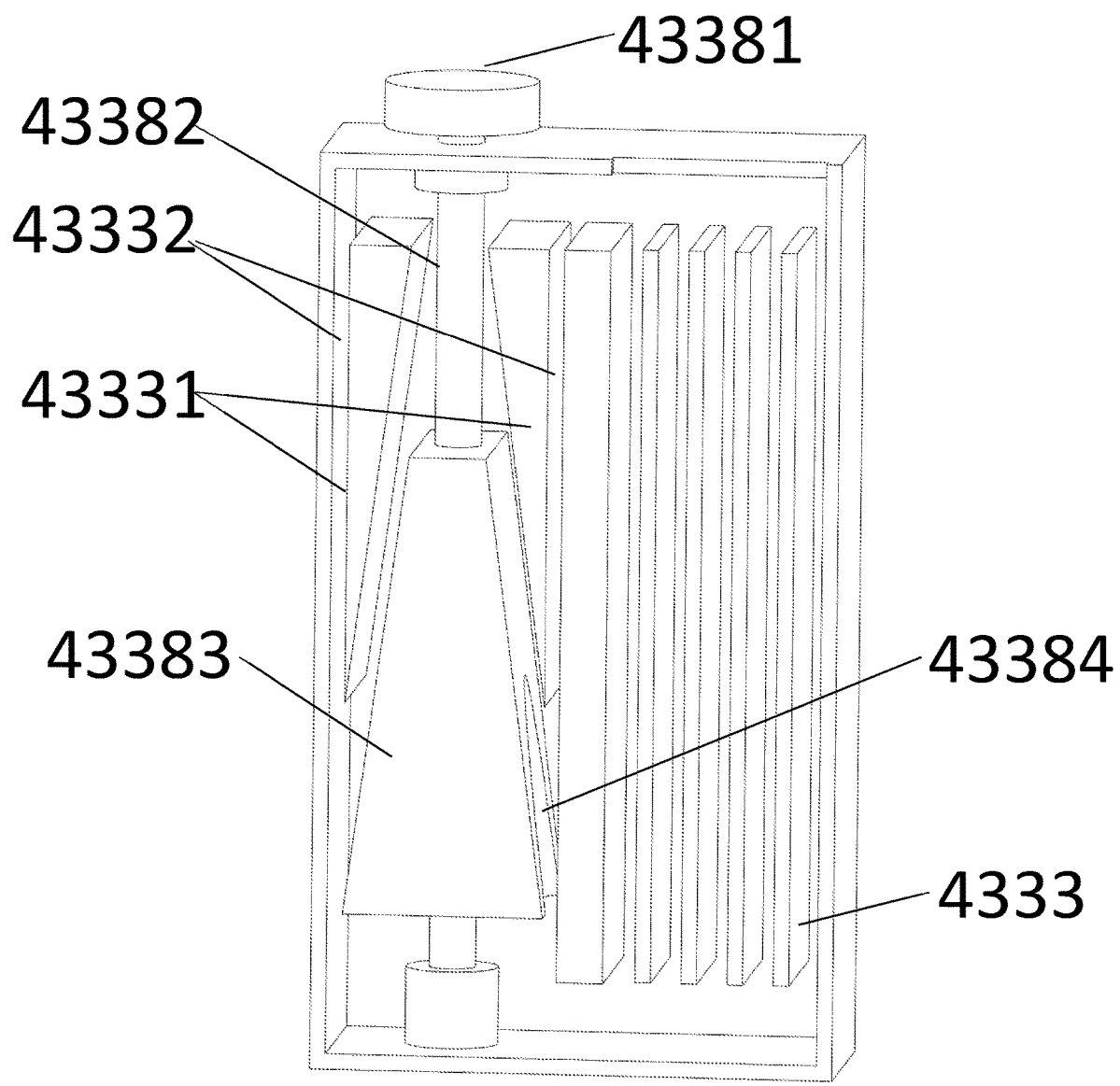
FIG. 19 is a structural schematic diagram of a fourth embodiment of a buffer device in an exoskeleton in the present invention.

In addition, the linear damping box 433 in the present embodiment may not adopt the multilayer damping fluid diversion groove 4333 having the upper and lower layers of reflow structures, and may adopt a form of left and right distribution. With reference to FIG. 19, in a specific embodiment, the linear damping box 433 is divided into a damping coefficient adjustable reflow region on the left side and a paddle diversion region on the right side. The upper part of the damping coefficient adjustable reflow region on the left side is provided with two semi-wedge-shaped stopper blocks 43331, and a plurality of damping fluid diversion grooves 4333 are arranged side by side in the paddle diversion region on the right side. An overflow groove 43332 is provided on the outer side of the left and the right semi-wedge-shaped (or directly triangular) stopper blocks 43331. In addition, to adapt to the linear damping box 433, the rotation damping regulating valve 4338 in the present embodiment comprises a damping regulating lead screw 43382, a damping regulating knob 43381 and an isosceles-trapezoidal/wedge-shaped damping regulating block 43383. The damping regulating knob 43381 is arranged at the top end of the damping regulating lead screw 43382, and the bottom end of the damping regulating lead screw 43382 is installed in the damping box body through the regulating valve mounting hole 4339 at the top left side of the damping box body 4332 (abutted against the bottom in the damping box body). The damping regulating block 43383 is arranged on the damping regulating lead screw 43382 by moving up and down relative to the damping regulating lead screw 43382, and is close to the bottom end side of the damping regulating lead screw 43382. Two semi-wedge-shaped stopper blocks 43331 are respectively located on both sides of the bottom side of the isosceles-trapezoid-shaped damping regulating block 43383 (specifically, the oblique sides of the two semi-wedge-shaped stopper blocks 43331 are respectively parallel to the oblique sides of both sides of the damping regulating block 43383). The bottom of the damping regulating block 43383 is provided with diversion ports from a lower bottom side to the waists/oblique sides of both sides, so that adjustable section reflow grooves 43384 are formed on the waists/oblique sides of both sides of the damping regulating block 43383. When the damping regulating knob 43381 rotates, the damping regulating knob 43381 drives the damping regulating lead screw 43382 to rotate, and the damping regulating block 43383 moves up and down along an axis of the damping regulating lead screw 43382, so that the adjustable section reflow grooves 43384 are gradually close to/away from the semi-wedge-shaped stopper blocks 43331, thereby regulating the flow cross section.

With reference to FIG. 19, when the adjustable section reflow groove 43383 is furthest from the semi-wedgeshaped stopper block 43331 (e.g., when the damping regulating block 43383 moves to the bottom of the damping regulating lead screw 43382), because the gap between the adjustable section reflow groove 43384 and the semi-wedge-shaped stopper block 43331 is largest, the adjustable section reflow groove 43384 allows the cross-sectional area of the damping fluid to be maximized. At this moment, the damping coefficient is minimal. When the adjustable section reflow groove 43383 is closest to the semi-wedge-shaped stopper block 43331 (for example, when the damping regulating block 43383 moves to the upper part of the damping regulating lead screw 43382), because the waists/oblique sides of both sides of the damping regulating block 43383 completely coincide with the oblique sides of the two semi-wedge-shaped stopper blocks 43331 on both sides of the top of the damping regulating lead screw 43382, i.e., the adjustable section reflow groove 43383 is sealed by the semi-wedge-shaped stopper blocks 43331, only a little damping fluid can flow through the overflow groove 43332 on the outer side of the two semi-wedge-shaped stopper blocks 43331. At this moment, the damping coefficient is maximal.

Embodiment 7

The exoskeleton in the present embodiment comprises various components in any embodiment above, and the same reference numerals indicate the same components. Differently, in the present embodiment, the exoskeleton is provided with the hip unit coupled with the above back-carrying assisting unit 1 and the lower limb unit 4, so that the load of the back-carrying assisting unit 1 (even the load transmitted by the front-carrying assisting unit 2 to the back-carrying assisting unit 1 through the force transmission unit 3) is transmitted to the lower limb unit 4.

Figure 20A:
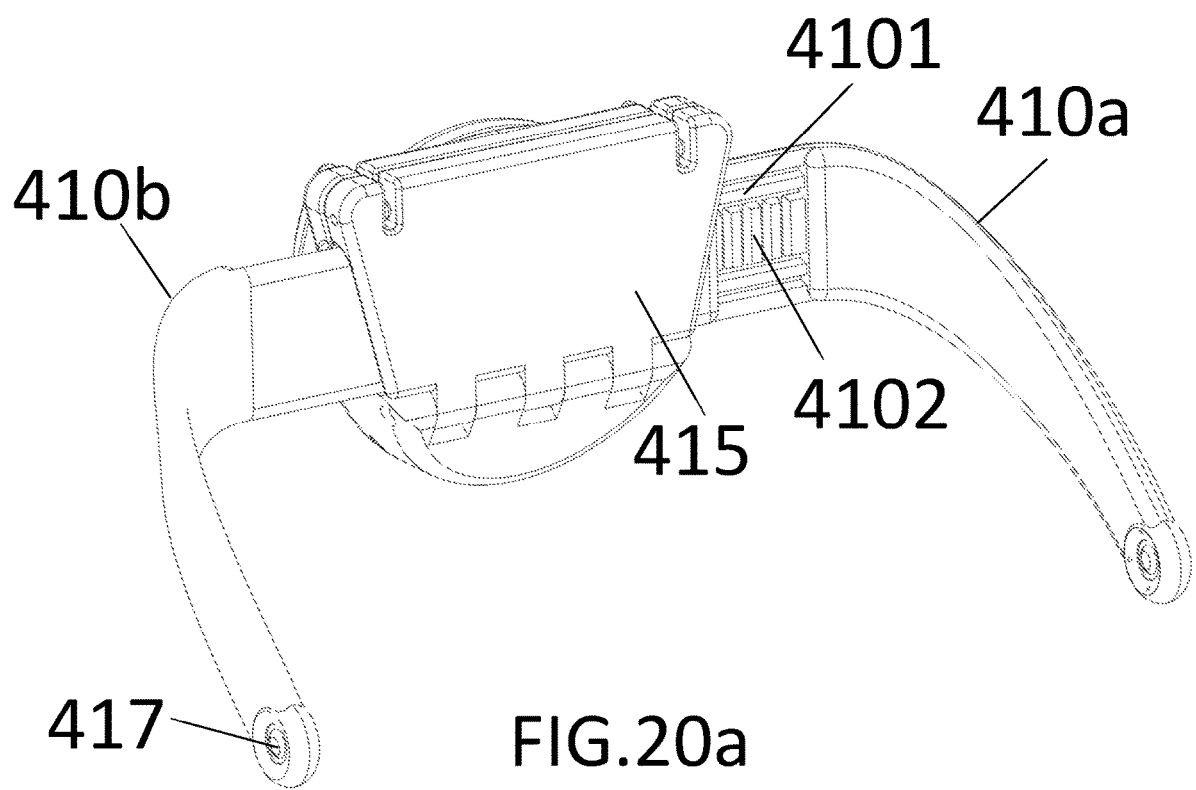
Figure 20B:
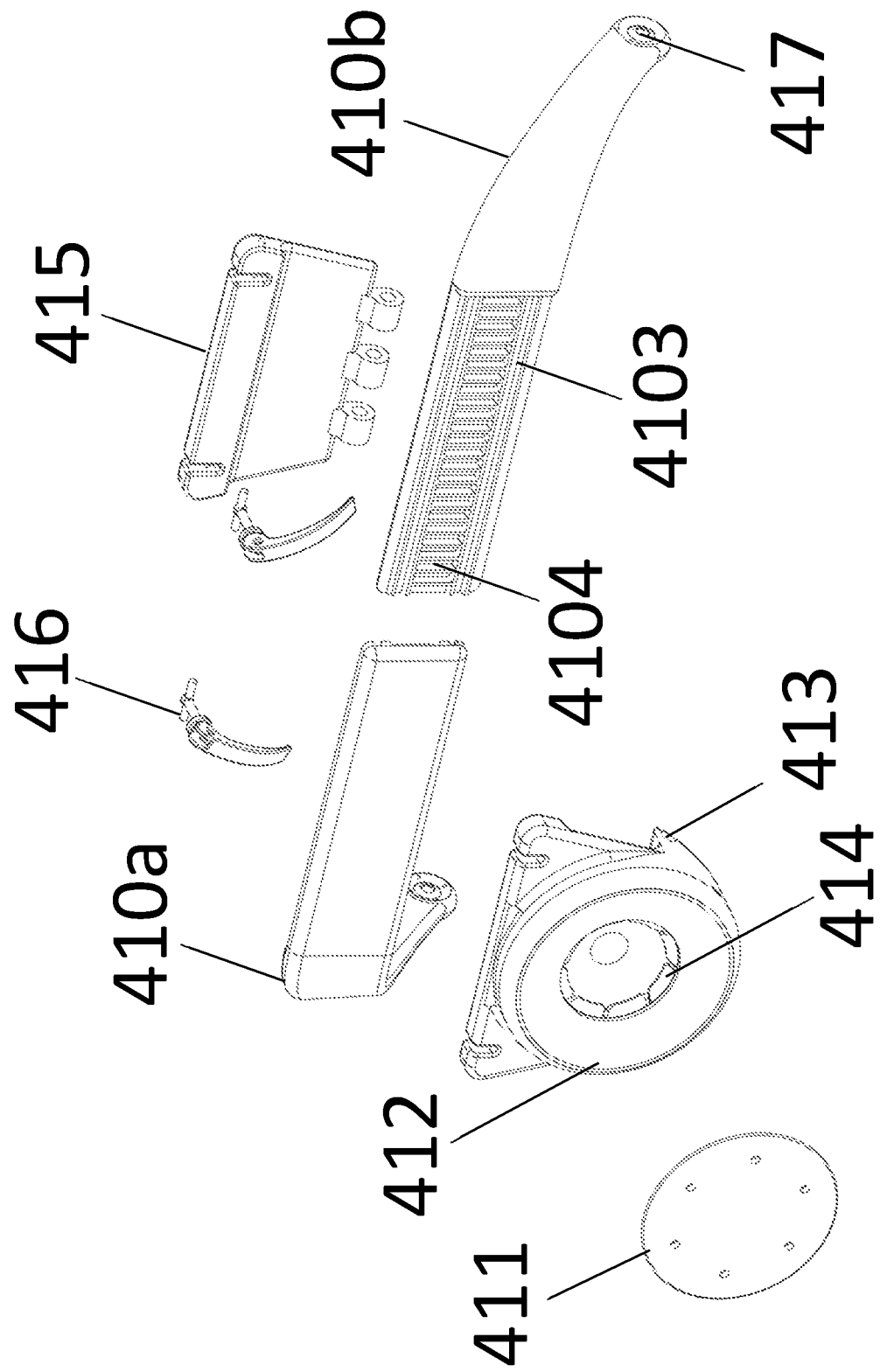

In a specific embodiment, with reference to FIG. 20*a* and FIG. 20*b*, the hip unit 41 comprises a left hip part 410*a*, a right hip part 410*b*, an elastic locking docking head 411, a tenon end cover 412, a tenon mounting seat 413, a locking tenon 414, a back connecting splint 415, a quick-release member 416 and a hip joint 417 (which can be implemented by the structure of the quick-release joint in the above embodiment).

The left hip 410*a* comprises two rails 4101 parallel to the horizontal plane, and a plurality of clamping teeth 4102 arranged between the two rails 4101 in the vertical plane, as shown in FIG. 20*a*. The right hip part 410*b* comprises two lug bosses 4103 parallel to the horizontal plane, and a plurality of clamping teeth 4104 arranged between the two lug bosses 4103 in the vertical plane. The working principle is: during use, a horizontal rail 4101 of the left hip part 410*a* and the horizontal lug boss 4103 of the right hip part 410*b* are fastened together, and clamped by the tenon mounting seat 413 and the back connecting splint 415, thereby distributing the gravity of the load (from the back-carrying assisting unit) received by the tenon mounting seat 413 to joint bearings of the hip joints 417 of the left hip part 410*a* and the right hip part 410*b*. The clamping teeth 4102 of the left hip part 410*a* and the clamping teeth 4104 of the right hip part 410*b* in the vertical plane are engaged with each other so that the hip unit 41 fits directly to the waist width of the human body. In addition, in the present embodiment, if the width of the hip unit 41 is not matched with the waist width of the wearer, the left hip part 410*a* and the right hip part 410*b* can horizontally slide by simply releasing the quick-release member 416 on the back connecting splint 415. The clamping teeth of the left hip part 410*a* and the right hip part 410*b* in different vertical planes are fastened together to achieve an ideal waist width.

The docking head 411 is connected with the above fixed seat 111 to ensure that the weight of the back-carrying assisting unit 1 and/or the front-carrying assisting unit 2 is transmitted to the hip unit 41. The back connecting splint 415 and the quick-release member 416 cooperate to quickly lock or unlock the hip unit 41 and the lower limb supporting unit 4, thereby transmitting the weight borne by the hip unit 41 to the lower limb supporting unit 4, as shown in FIG. 1*b*.

In a specific embodiment, the tenon end cover 412 and the tenon mounting seat 413 may be of an integral structure or may be designed as two separate components that can be locked or unlocked. The elastic locking docking head 411 and the locking tenon 414 can be locked or unlocked under cooperation. The back connecting splint 415 can be divided into two surfaces. The locking tenon 414 is fixedly installed on one surface of the back connecting splint 415. When the back connecting splint 415 is assembled, the two surfaces of the splint are fastened together, and the quick-release members 416 (in the embodiment shown in FIG. 20*a*, there are two quick-release members 416 which can be respectively inserted into the grooves on both sides of the upper end of the back connecting splint 415) are used to securely lock the two surfaces of the back connecting splint 415 together.

The present invention can be well realized in accordance with the above embodiments. It should be noted that, based on the above design principle, to solve the same technical problem, even if some insubstantial changes or improvements are made on the basis of the structure disclosed by the present invention, the adopted technical solution is substantially still the same as that of the present invention, and thus shall also be within the protection scope of the present invention.

The invention claimed is:
1. An exoskeleton, comprising a back-carrying assisting unit, wherein the back-carrying assisting unit comprises a spinal locomotion adaptation unit arranged to be adapted to locomotion of a back of a human body when the back-carrying assisting unit carries a load or spine of the human body bends forwards, backwards, leftwards or rightwards;
   wherein the spinal locomotion adaptation unit is a flexible body; and a plurality of groups of spinal locomotion adaptation structures are arranged on the flexible body evenly along a lengthwise direction from top to bottom, and are used to provide a deformation space in a corresponding direction for the flexible body when the human body bends forwards, backwards, leftwards or rightwards;
   wherein the flexible body is further provided with a rigidity regulating unit used for regulating a rigidity of the flexible body, and
   wherein the rigidity regulating unit comprises two pull lines; and
   wherein left and right sides of the flexible body are provided with a first pull line passage and a second pull line passage side by side along the lengthwise direction, wherein fixed ends of the pull lines are fixed to a bottom of the first pull line passage, and free ends of the pull lines penetrate through the first pull line passage and the second pull line passage in sequence and penetrate out of a bottom of the second pull line passage; and,
   when the free ends of the two pull lines are simultaneously pulled downwards, pulling force generated by the pull lines compresses the each group of spinal locomotion adaptation structure, so as to enhance the rigidity of the flexible body.

2. The exoskeleton according to claim 1, wherein each group of spinal locomotion adaptation structures comprises a left-tilting slot, a rear-tilting slot, a right-tilting slot, and a front-tilting slot that are staggered in sequence from top to bottom of each group of spinal adaption structures.

3. The exoskeleton according to claim 1, wherein a bottom of the flexible body is provided with a rotating adaptation structure so that the flexible body can rotate and deform in a horizontal plane.

4. The exoskeleton according to claim 1, wherein elastic components are connected at the fixed ends of the pull lines and are used to bear a pulling force of the pull lines, finally achieving force balance with the pulling force of the pull lines and simultaneously compressing the spinal locomotion adaptation structure.

5. The exoskeleton according to claim 1, the back-carrying assisting unit further comprises a back-carrying weight-bearing unit, wherein the back-carrying weight-bearing unit is associated with the rigidity regulating unit, is transmitted to the rigidity regulating unit when the back-carrying weight-bearing unit carries the load, to compress the spinal locomotion adaptation structure.

6. The exoskeleton according to claim 5, wherein the back-carrying weight-bearing unit comprises a fixed seat and a weight-bearing platform hinged on a fixed platform, wherein the fixed seat is arranged at a bottom of the flexible body by sliding up and down relative to the flexible body, and is connected with the free ends of the two pull lines; and
wherein in an initial state, the weight-bearing platform is attached to the fixed seat; and,
when the weight-bearing platform rotates to form an angle of 45° to 90° with one side of the fixed seat away from a back/hip, the weight-bearing platform and the fixed seat form a weight-bearing space for accommodating loads; and when the loads are put into the weight-bearing space, the fixed seat drives the free ends of the two pull lines to slide downwards, to compress the spinal locomotion adaptation structure.

7. The exoskeleton according to claim 1, wherein the back-carrying assisting unit and a front-carrying assisting unit are connected through a force transmission unit, wherein the front-carrying assisting unit transmits weight of the a force-carrying load to the back-carrying assisting unit through the force transmission unit; wherein the force transmission unit comprises a left and a right force transmission components and a left and a right contraction devices having self-locking units, and wherein one end of each of the left and the right force transmission components is respectively twined into the left and the right contraction devices; and when the self-locking units in the contraction devices are unlocked, the contraction devices release the force transmission components twined into the contraction devices; and
when the other end of each of the left and the right force transmission components is respectively fixedly connected with the left side and the right side of the front-carrying assisting unit, the left and the right contraction devices are respectively fixed to the left side and the right side of the back-carrying assisting unit; or when the other end of each of the left and the right force transmission components is respectively fixedly connected with the left side and the right side of the back-carrying assisting unit, the left and the right contraction devices are respectively fixed to the left side and the right side of the front-carrying assisting unit.

8. The exoskeleton according to claim 7, wherein the front-carrying assisting unit comprises a left contactor and a right contactor; each contactor comprises a palm supporting cushion, a finger supporting cushion and a wearable component, wherein one end of the palm supporting cushion is connected with a fixed end of the force transmission component, and an other end is hinged with the finger supporting cushion; and the wearable component is arranged on the palm supporting cushion;
wherein a back surface of the finger supporting cushion is also provided with a clamping part used for clamping between two fingers.

9. The exoskeleton according to claim 7, wherein the front-carrying assisting unit comprises a left contactor and a right contactor; each contactor comprises a palm supporting cushion, a finger supporting cushion and a finger connecting piece, wherein the palm supporting cushion and the finger supporting cushion are respectively hinged with the finger connecting piece, and the palm supporting cushion is also connected with a fixed end of the force transmission component;
wherein each of the contactors further comprises a fingertip protecting jacket arranged at an end of the finger supporting cushion.

10. The exoskeleton according to claim 7, wherein the front-carrying assisting unit comprises a left contactor and a right contactor; and wherein each contactor comprises a palm supporting cushion and a hooked weight-bearing part; and wherein one end of the hooked weight-bearing part is rotatably connected with the palm supporting cushion; and the palm supporting cushion is provided with an accommodating groove with an L-shaped cross section; and
in an initial state, the hooked weight-bearing part is located on the accommodating groove to form, with a load base, a surface contactor that can be attached to a side surface of a front-carrying load; and,
when the hooked weight-bearing part rotates to be perpendicular to a vertical plane, the hooked weight-bearing part and the palm supporting cushion form a weight-bearing unit with an L-shaped cross section used for front lifting of the load; or
when the hooked weight-bearing part rotates to be parallel to the vertical plane, the hooked weight-bearing part is used to lift the load.

11. The exoskeleton according to claim 7, wherein the back-carrying assisting unit further comprises a shoulder supporting piece and a back-carrying weight-bearing unit; the shoulder supporting piece, the spinal locomotion adaptation unit and the back-carrying weight-bearing unit are connected in sequence, wherein the shoulder supporting piece is connected with the force transmission unit.

* * * * *